(12) United States Patent
Smolke et al.

(10) Patent No.: US 8,772,464 B2
(45) Date of Patent: Jul. 8, 2014

(54) APTAMER REGULATED NUCLEIC ACIDS AND USES THEREOF

(75) Inventors: Christina D. Smolke, Pasadena, CA (US); Travis S. Bayer, San Francisco, CA (US)

(73) Assignee: California Institute of Technology, Pasadena, CA (US)

( * ) Notice: Subject to any disclaimer, the term of this patent is extended or adjusted under 35 U.S.C. 154(b) by 1535 days.

(21) Appl. No.: 11/884,110

(22) PCT Filed: Feb. 9, 2006

(86) PCT No.: PCT/US2006/004801
§ 371 (c)(1),
(2), (4) Date: Jul. 29, 2008

(87) PCT Pub. No.: WO2006/086669
PCT Pub. Date: Aug. 17, 2006

(65) Prior Publication Data
US 2012/0035065 A1    Feb. 9, 2012

(51) Int. Cl.
*C12N 15/115*    (2010.01)
*C12N 15/11*    (2006.01)
*C12Q 1/25*    (2006.01)
*C12Q 1/68*    (2006.01)
*C12N 15/00*    (2006.01)

(52) U.S. Cl.
USPC ......... 536/23.1; 536/24.1; 435/6.1; 435/91.1; 435/320.1

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,426,330 A | 1/1984 | Sears |
| 4,501,728 A | 2/1985 | Geho et al. |
| 4,534,899 A | 8/1985 | Sears |
| 4,737,323 A | 4/1988 | Martin et al. |
| 4,837,028 A | 6/1989 | Allen |
| 4,897,355 A | 1/1990 | Eppstein et al. |
| 5,013,556 A | 5/1991 | Woodle et al. |
| 5,013,830 A | 5/1991 | Ohtsuka et al. |
| 5,093,246 A | 3/1992 | Cech et al. |
| 5,108,921 A | 4/1992 | Low et al. |
| 5,176,996 A | 1/1993 | Hogan et al. |
| 5,213,804 A | 5/1993 | Martin et al. |

(Continued)

FOREIGN PATENT DOCUMENTS

| | | |
|---|---|---|
| AU | 2004206255 A1 | 8/2004 |
| WO | WO-88/04300 | 6/1988 |

(Continued)

OTHER PUBLICATIONS

Silverman, Rube Goldberg goes (ribo)nuclear? Molecular switches and sensors made from RNA, RNA 2003 9: 377-383.*

(Continued)

*Primary Examiner* — Jim Ketter
*Assistant Examiner* — Reza Ghafoorian
(74) *Attorney, Agent, or Firm* — McCarter & English, LLP; Elizabeth A. Hanley; Yu Lu

(57) ABSTRACT

The invention relates to aptamer-regulated, ligand-responsive nucleic acids, or "ampliSwitches," and uses thereof. Particular embodiments include a ligand-responsive nucleic acid that comprises a primer sequence domain and an aptamer domain that is responsive to a ligand.

18 Claims, 21 Drawing Sheets

(56) References Cited

U.S. PATENT DOCUMENTS

| | | |
|---|---|---|
| 5,214,135 A | 5/1993 | Srivastava et al. |
| 5,227,170 A | 7/1993 | Sullivan |
| 5,256,775 A | 10/1993 | Froehler |
| 5,264,221 A | 11/1993 | Tagawa et al. |
| 5,264,423 A | 11/1993 | Cohen et al. |
| 5,264,564 A | 11/1993 | Matteucci |
| 5,270,163 A | 12/1993 | Gold et al. |
| 5,276,019 A | 1/1994 | Cohen et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,500,357 A | 3/1996 | Taira et al. |
| 5,512,295 A | 4/1996 | Kornberg et al. |
| 5,521,291 A | 5/1996 | Curiel et al. |
| 5,525,719 A | 6/1996 | Srivastava et al. |
| 5,527,528 A | 6/1996 | Allen et al. |
| 5,534,259 A | 7/1996 | Zalipsky et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,580,575 A | 12/1996 | Unger et al. |
| 5,582,981 A | 12/1996 | Toole et al. |
| 5,583,020 A | 12/1996 | Sullivan |
| 5,591,721 A | 1/1997 | Agrawal et al. |
| 5,595,756 A | 1/1997 | Bally et al. |
| 5,736,392 A | 4/1998 | Hawley-Nelson et al. |
| 5,756,291 A | 5/1998 | Griffin et al. |
| 5,767,099 A | 6/1998 | Harris et al. |
| 5,777,153 A | 7/1998 | Lin et al. |
| 5,780,053 A | 7/1998 | Ashley et al. |
| 5,830,430 A | 11/1998 | Unger et al. |
| 5,830,653 A | 11/1998 | Froehler et al. |
| 5,851,548 A | 12/1998 | Dattagupta et al. |
| 5,855,910 A | 1/1999 | Ashley et al. |
| 6,458,559 B1 | 10/2002 | Shi et al. |
| 6,706,474 B1 | 3/2004 | Lu et al. |
| 1,000,289 A1 | 1/2011 | Galloway et al. |
| 2002/0106648 A1 | 8/2002 | Lizardi et al. |
| 2002/0150996 A1 | 10/2002 | Nilsen-Hamilton |
| 2002/0166132 A1 | 11/2002 | Scherman et al. |
| 2003/0105051 A1 | 6/2003 | McSwiggen |
| 2003/0124595 A1 | 7/2003 | Lizardi |
| 2003/0157030 A1 | 8/2003 | Davis et al. |
| 2004/0063654 A1 | 4/2004 | Davis et al. |
| 2004/0072785 A1 | 4/2004 | Wolff et al. |
| 2004/0086884 A1 | 5/2004 | Beach |
| 2004/0162235 A1 | 8/2004 | Trubetskoy et al. |
| 2004/0204377 A1 | 10/2004 | Rana |
| 2005/0003362 A1 | 1/2005 | Krylov et al. |
| 2005/0026286 A1 | 2/2005 | Chi et al. |
| 2005/0037496 A1 | 2/2005 | Rozema et al. |
| 2005/0042227 A1 | 2/2005 | Zankel et al. |
| 2005/0048647 A1 | 3/2005 | Taira et al. |
| 2005/0064595 A1 | 3/2005 | MacLachlan et al. |
| 2005/0256071 A1 | 11/2005 | Davis |
| 2005/0265957 A1 | 12/2005 | Monahan et al. |
| 2006/0008910 A1 | 1/2006 | MacLachlan et al. |
| 2006/0088864 A1 | 4/2006 | Smolke et al. |
| 2006/0105975 A1 | 5/2006 | Pendergrast et al. |
| 2006/0121510 A1 | 6/2006 | Breaker et al. |
| 2006/0172925 A1 | 8/2006 | Gorenstein et al. |
| 2006/0178327 A1 | 8/2006 | Yeung |
| 2006/0240093 A1 | 10/2006 | MacLachlan et al. |
| 2007/0077571 A1 | 4/2007 | Ellington et al. |
| 2007/0083947 A1 | 4/2007 | Huang et al. |
| 2007/0231392 A1 | 10/2007 | Wagner et al. |
| 2008/0038296 A1 | 2/2008 | Brahmbhatt et al. |
| 2008/0107694 A1 | 5/2008 | Trogden et al. |
| 2008/0112916 A1 | 5/2008 | Wagner et al. |
| 2008/0152661 A1 | 6/2008 | Rozema et al. |
| 2009/0082217 A1 | 3/2009 | Smolke et al. |
| 2009/0098561 A1 | 4/2009 | Smolke et al. |
| 2009/0143327 A1 | 6/2009 | Smolke et al. |
| 2009/0234109 A1 | 9/2009 | Han et al. |
| 2010/0226901 A1 | 9/2010 | Smolke et al. |
| 2010/0255545 A1 | 10/2010 | Smolke et al. |
| 2012/0165387 A1 | 6/2012 | Smolke et al. |

FOREIGN PATENT DOCUMENTS

| | | |
|---|---|---|
| WO | WO-88/09810 | 12/1988 |
| WO | WO-89/10134 | 11/1989 |
| WO | WO-90/11364 | 10/1990 |
| WO | WO-9014074 A1 | 11/1990 |
| WO | WO-9116024 A1 | 10/1991 |
| WO | WO-9117424 A1 | 11/1991 |
| WO | WO-9203568 A1 | 3/1992 |
| WO | WO-97/42317 | 11/1997 |
| WO | WO-9813526 A1 | 4/1998 |
| WO | WO-99/04800 | 2/1999 |
| WO | WO-99/27133 | 6/1999 |
| WO | WO-99/54506 | 10/1999 |
| WO | WO-00/20040 | 4/2000 |
| WO | WO-2004/033653 | 4/2004 |
| WO | WO-2004048545 A2 | 6/2004 |
| WO | WO-2004065601 A2 | 8/2004 |
| WO | WO-2005001039 A2 | 1/2005 |
| WO | WO-2005111238 A2 | 11/2005 |
| WO | WO-2006086669 A2 | 8/2006 |
| WO | WO-2007089607 A2 | 8/2007 |
| WO | WO-2008036825 A2 | 3/2008 |
| WO | WO-2008058291 A2 | 5/2008 |

OTHER PUBLICATIONS

Alberts et al., The molecular biology of the Cell, Chapter 6: DNA Replication, Repair, and Recombination, Preliminary Version 2003 Garland Sciences.*

Dellarole et al., Thermodynamics of Cooperative DNA Recognition at a Replication Origin and Transcription Regulatory Site, Biochemistry 2010, 49, 10277-10286.*

Tindall et al., Fidelity of DNA Synthesis by the Thermus aquaticus DNA Polymerase, the American Chemical Society vol. 27, No. 16, 1988.*

Snyder et al., Bent DNA at a yeast autonomously replicating sequence, Nature, vol. 324, Nov. 6, 1986.*

Soukup et al., Riboswitches exert genetic control through metabolite-induced conformational change, Current Opinion in Structural Biology 2004, 14:344-349.*

Schwalbe et al., Structures of RNA Switches: Insight into Molecular Recognition and Tertiary Structure, Angew. Chem. Int. Ed. 2007, 46, 1212-1219.*

Serganov et al., Ribozymes, riboswitches and beyond: regulation of gene expression without proteins, Nature, Oct. 2007, vol. 8, p. 776.*

Montange et al., Structure of the S-adenosylmethionine riboswitch regulatory mRNA element, Nature, vol. 441, Jun. 29, 2006, p. 1172.*

Hanson et al., Molecular analysis of a synthetic tetracycline-binding riboswitch, RNA (2005), 11:503-511.*

Agrawal et al., RNA Interference: Biology, Mechanism, and Applications. Microbiology and Molecular Biology Reviews. vol. 67, No. 4 pp. 657-685 (2003).

Soukup et al., Nucleic Acid Molecular Switches. Nanotechnology vol. 17 pp. 469-474 (1999).

Vuyisich et al. Controlling protein activity with ligand-RNA aptamers. Chemistry & Biology. vol. 9, pp. 907-913 (2002).

Al-Douahji et al., "The cyclin kinase inhibitor p21WAF1/CIP1 is required for glomerular hypertrophy in experimental diabetic nephropathy," Kidney Int 56:1691-1699 (1999).

Banerjee et al., "Control of developmental timing by small temporal RNAs: a paradigm for RNA-mediated regulation of gene expression," Bioessays 24:119-129 (2002).

Barrick et al., "New RNA motifs suggest an expanded scope for riboswitches in bacterial genetic control," Proc Natl Acad Sci USA 101:6421-6426 (2004).

(56) References Cited

OTHER PUBLICATIONS

Bartel, "MicroRNAs: genomics, biogenesis, mechanism, and function," Cell 116:281-297 (2004).
Batzer et al., "Enhanced evolutionary PCR using oligonucleotides with inosine at the 3'-terminus," Nucleic Acids Res 19:5081 (1991).
Bayer et al., "Programmable ligand-controlled riboregulators of eukaryotic gene expression," Nat Biotechnol 23:337-343 (2005).
Been and Cech, "One binding site determines sequence specificity of Tetrahymena pre-rRNA self-splicing, trans-splicing, and RNA enzyme activity," Cell 47:207-216 (1986).
Benoist et al., "In vivo sequence requirements of the SV40 early promotor region," Nature 290:304-310 (1981).
Berens et al., "A tetracycline-binding RNA aptamer," Bioorg Med Chem 9:2549-2556 (2001).
Blind et al., "Cytoplasmic RNA modulators of an inside-out signal-transduction cascade," Proc Natl Acad Sci USA 96:3606-3610 (1999).
Brennecke et al., "Towards a complete description of the microRNA complement of animal genomes," Genome Biol 4:228.1-228.3 (2003).
Brinster et al., "Regulation of metallothionein-thymidine kinase fusion plasmids injected into mouse eggs," Nature 296:39-42 (1982).
Brummelkamp et al., "A system for stable expression of short interfering RNAs in mammalian cells," Science 296:550-553 (2002).
Buskirk et al., "Engineering a ligand-dependent RNA transcriptional activator," Chem Biol 11:1157-1163 (2004).
Buskirk et al., "In Vivo Evolution of an RNA-Based Transcriptional Activator," *Chemistry & Biology* 10:533-540 (2003).
Caplen et al., "Specific inhibition of gene expression by small double-stranded RNAs in invertebrate and vertebrate systems," Proc Natl Acad Sci USA 98:9742-9747 (2001).
Caponigro et al., "A small segment of the MAT?1 transcript promotes mRNA decay in *Saccharomyces cerevisiae*: a stimulatory role for rare codons," Mol Cell Biol 13:5141-5148 (1993).
Chen et al., "Synthesis of oligodeoxyribonucleotide N3' P5' phosphoramidates," Nucleic Acids Res 23:2661-2668 (1995).
Cox et al., "Automated selection of aptamers against protein targets translated in vitro: from gene to aptamer," Nucleic Acids Res 30:e108 (2002).
Dragun et al., "ICAM-1 antisense oligodesoxynucleotides prevent reperfusion injury and enhance immediate graft function in renal transplantation," Kidney Int 54:590-602 (1998).
Dragun et al., "Inhibition of intercellular adhesion molecule-1 with antisense deoxynucleotides prolongs renal isograft survival in the rat," Kidney Int 54:2113-2122 (1998).
Egholm et al., "PNA hybridizes to complementary oligonucleotides obeying the Watson-Crick hydrogen-bonding rules," Nature 365:566-568 (1993).
Elbashir et al., "Duplexes of 21-nucleotide RNAs mediate RNA interference in cultured mammalian cells," Nature 411:494-498 (2001).
Ellington et al., "In vitro selection of RNA molecules that bind specific ligands," Nature 346:818-822 (1990).
Famulok "Bringing Picomolar Protein Detection Into Proximity," Nature *Biotechnology* 20:448-449 (2002).
Famulok, "Oligonucleotide aptamers that recognize small molecules," Curr Opin Struct Biol 9:324-329 (1999).
Fredriksoon et al., "Protein Detection Using Proximity-Dependent DNA Litagation Assays," *Nature Biotechnology* 20:473-477 (2002).
Gardner et al., "Inferring genetic networks and identifying compound mode of action via expression profiling," Science 301:102-105 (2003).
Gautier et al., "?-DNA. IV: ?-anomeric and ?-anomeric tetrathymidylates covalently linked to intercalating oxazolopyridocarbazole. Synthesis, physicochemical properties and poly (rA) binding," Nucleic Acids Res 15:6625-6641 (1987).
Gil et al., "Induction of apoptosis by the dsRNA-dependent protein kinase (PKR): mechanism of action," Apoptosis 5:107-114 (2000).
Good, "Diverse antisense mechanisms and applications," Cell Mol Life Sci 60:823-824 (2003).

Good, "Translation repression by antisense sequences," Cell Mol Life Sci 60:854-861 (2003).
Gouda et al., "Free energy calculations for theophylline binding to an RNA aptamer: Comparison of MM-PBSA and thermodynamic integration methods," Biopolymers 68:16-34 (2003).
Haller et al., "Antisense oligonucleotides for ICAM-1 attenuate reperfusion injury and renal failure in the rat," Kidney Int 50:473-480 (1996).
Hamm et al., "Anti-idiotype RNA selected with an anti-nuclear export signal antibody is actively transported in oocytes and inhibits Rev- and cap-dependent RNA export," Proc Natl Acad Sci USA 94:12839-12844 (1997).
Haseloff et al., "Simple RNA enzymes with new and highly specific endoribonuclease activities," Nature 334:585-591 (1988).
Heidenreich et al., "RNase H-independent antisense activity of oligonucleotide N3' P5' phosphoramidates," Nucleic Acids Res 25:776-780 (1997).
Hermann et al., "Adaptive recognition by nucleic acid aptamers," Science 287:820-825 (2000).
Hesselberth et al., "Simultaneous detection of diverse analytes with an aptazyme ligase array," Anal Biochem 312:106-112 (2003).
Hirschbein et al., "31P NMR spectroscopy in oligonucleotide research and development," Antisense Nucleic Acid Drug Dev 7:55-61 (1997).
Huizenga et al., "A DNA aptamer that binds adenosine and ATP," Biochemistry 34:656-665 (1995).
Inoue et al., "Sequence-dependent hydrolysis of RNA using modified oligonucleotide splints and RNase H," FEBS Lett 215:327-330 (1987).
Inoue et al., "Synthesis and hybridization studies on two complementary nona(2'-O-methyl)ribonucleotides," Nucleic Acids Res 15:6131-6148 (1987).
Isaacs et al., "Engineered riboregulators enable post-transcriptional control of gene expression," Nat Biotechnol 22:841-847 (2004).
Jhaveri et al., "In vitro selection of signaling aptamers," Nat Biotechnol 18:1293-1297 (2000).
Jose et al., "Cooperative binding of effectors by an allosteric ribozyme," Nucleic Acids Res 29:1631-1637 (2001).
Kertsburg et al., "A versatile communication module for controlling RNA folding and catalysis," Nucleic Acids Res 30:4599-4606 (2002).
Khosla et al., "Metabolic engineering for drug discovery and development," Nat Rev Drug Discov 2:1019-1025 (2003).
Kim, "Small RNAs: classification, biogenesis, and function," Mol Cells 19:1-15 (2005).
Kipshidze et al., "Intramural coronary delivery of advanced antisense oligonucleotides reduces neointimal formation in the porcine stent restenosis model," J Am Coll Cardiol 39:1686-1691 (2002).
Kipshidze et al., "Local delivery of c-myc neutrally charged antisense oligonucleotides with transport catheter inhibits myointimal hyperplasia and positively affects vascular remodeling in the rabbit balloon injury model," Catheter Cardiovasc Intery 54:247-256 (2001).
Kobayashi et al., "Programmable cells: interfacing natural and engineered gene networks," Proc Natl Acad Sci USA 101:8414-8419 (2004).
Koch, "The metabolism of methylpurines by *Escherichia coli*. I. Tracer studies," J Biol Chem 219:181-188 (1956).
Koizumi et al., "Allosteric selection of ribozymes that respond to the second messengers cGMP and cAMP," Nat Struct Biol 6:1062-1071 (1999).
Kramer et al., "Role for antisense RNA in regulating circadian clock function in *Neurospora crassa*," Nature 421:948-952 (2003).
Kutryk et al., "Local intracoronary administration of antisense oligonucleotide against c-myc for the prevention of in-stent restenosis: results of the randomized investigation by the Thoraxcenter of antisense DNA using local delivery and IVUS after coronary stenting (ITALICS) trial," J Am Coll Cardiol 39:281-287 (2002).
Kuwabara et al., "Allosterically controllable maxizyme-mediated suppression of progression of leukemia in mice," Biomacromolecules 2:1220-1228 (2001).

(56) References Cited

OTHER PUBLICATIONS

Kuwabara et al., "Allosterically controllable ribozymes with biosensor functions," Curr Opin Chem Biol 4:669-677 (2000).
Kuwabara et al., "Allosterically controlled single-chained maxizymes with extremely high and specific activity," Biomacromolecules 2:788-799 (2001).
Lavorgna et al., "In search of antisense," Trends Biochem Sci 29:88-94 (2004).
Lemaitre et al., "Specific antiviral activity of a poly(L-lysine)-conjugated oligodeoxyribonucleotide sequence complementary to vesicular stomatitis virus N protein mRNA initiation site," Proc Natl Acad Sci USA 84:648-652 (1987).
Letsinger et al., "Cholesteryl-conjugated oligonucleotides: synthesis, properties, and activity as inhibitors of replication of human immunodeficiency virus in cell culture," Proc Natl Acad Sci USA 86:6553-6556 (1989).
Lilley, "The origins of RNA catalysis in ribozymes," Trends Biochem Sci 28:495-501 (2003).
Lorsch et al., "In vitro selection of RNA aptamers specific for cyanocobalamin," Biochemistry 33:973-982 (1994).
Luzi et al., "New Trends in Affinity Sensing: Aptamers for Ligand Binding," *Trends in Analytical Chemistry* 22(11):810-818 (2003).
Mandal et al., "Adenine riboswitches and gene activation by disruption of a transcription terminator," Nat Struct Mol Biol 11:29-35 (2004).
Mannironi et al., "In vitro selection of dopamine RNA ligands," Biochemistry 36:9726-9734 (1997).
Mateus et al., "Destabilized green fluorescent protein for monitoring dynamic changes in yeast gene expression with flow cytometry," Yeast 16:1313-1323 (2000).
Mathews et al., "Incorporating chemical modification constraints into a dynamic programming algorithm for prediction of RNA secondary structure," Proc Natl Acad Sci USA 101:7287-7292 (2004).
McCaffrey et al., "RNA interference in adult mice," Nature 418:38-39 (2002).
McManus et al., "Gene silencing using micro-RNA designed hairpins," RNA 8:842-850 (2002).
Nagai et al., "A variant of yellow fluorescent protein with fast and efficient maturation for cell-biological applications," Nat Biotechnol 20:87-90 (2002).
Nutiu et al., "Structure-Swinging Signaling Aptamers: Transducing Molecular Recognition Into Fluorescence Signaling," *Chem. Eur. J.* 10:1868-1876 (2004).
Nutiu et al., "Structure-switching signaling aptamers," J Am Chem Soc 125:4771-4778 (2003).
Ohtsuka et al., "An alternative approach to deoxyoligonucleotides as hybridization probes by insertion of deoxyinosine at ambiguous codon positions," J Biol Chem 260:2605-2608 (1985).
Paddison et al., "Short hairpin RNAs (shRNAs) induce sequence-specific silencing in mammalian cells," Genes Dev 16:948-958 (2002).
Paddison et al., "Stable suppression of gene expression by RNAi in mammalian cells," Proc Natl Acad Sci USA 99:1443-1448 (2002).
Perry-O'Keefe et al., "Peptide nucleic acid pre-gel hybridization: an alternative to Southern hybridization," Proc Natl Acad Sci USA 93:14670-14675 (1996).
Piganeau et al., "In vitro selection of allosteric ribozymes: theory and experimental validation," J Mol Biol 312:1177-1190 (2001).
Robertson et al., "Design and optimization of effector-activated ribozyme ligases," Nucleic Acids Res 28:1751-1759 (2000).
Rossolini et al., "Use of deoxyinosine-containing primers vs degenerate primers for polymerase chain reaction based on ambiguous sequence information," Moll Cell Probes 8:91-98 (1994).
Roth et al., "Selection in vitro of allosteric ribozymes," Methods Mol Biol 252:145-164 (2004).
Samarsky et al., "A small nucleolar RNA:ribozyme hybrid cleaves a nucleolar RNA target in vivo with near-perfect efficiency," Proc Natl Acad Sci USA 96:6609-6614 (1999).
Sarver et al., "Ribozymes as potential anti-HIV-1 therapeutic agents," Science 247:1222-1225 (1990).

Scherer et al., "Approaches for the sequence-specific knockdown of mRNA," Nat Biotechnol 21:1457-1465 (2003).
Scherer et al., "Recent applications of RNAi in mammalian systems," Curr Pharm Biotechnol 5:355-360 (2004).
Silverman et al., "Rube Goldberg Goes (RIBO)Nuclear? Molecular Switches and Sensors Made From RNA," *RNA* 9:377-383 (2003).
Smolke et al., "Coordinated, differential expression of two genes through directed mRNA cleavage and stabilization by secondary structures," Appl Environ Microbiol 66:5399-5405 (2000).
Soukup et al., "Altering molecular recognition of RNA aptamers by allosteric selection," J Mol Biol 298:623-632 (2000).
Soukup et al., "Design of allosteric hammerhead ribozymes activated by ligand-induced structure stabilization," Structure 7:783-791 (1999).
Soukup et al., "Generating new ligand-binding RNAs by affinity maturation and disintegration of allosteric ribozymes," RNA 7:524-536 (2001).
Stein et al., "Oligodeoxynucleotides as inhibitors of gene expression: a review," Cancer Res 48:2659-2668 (1988).
Sui et al., "A DNA vector-based RNAi technology to suppress gene expression in mammalian cells," Proc Natl Acad Sci USA 99:5515-5520 (2002).
Taira et al., "Construction of a novel RNA-transcript-trimming plasmid which can be used both in vitro in place of run-off and (G)-free transcriptions and in vivo as multi-sequences transcription vectors," Nucleic Acids Res 19:5125-5130 (1991).
Tang et al., "Rational design of allosteric ribozymes," Chem Biol 4:453-459 (1997).
Tuerk et al., "Systematic evolution of ligands by exponential enrichment: RNA ligands to bacteriophage T4 DNA polymerase," Science 249:505-510 (1990).
Vacek et al., "Antisense-mediated redirection of mRNA splicing," Cell Mol Life Sci 60:825-833 (2003).
van der Krol et al., "Modulation of eukaryotic gene expression by complementary RNA or DNA sequences," Biotechniques 6:958-976 (1988).
Wagner et al., "Nucleotide sequence of the thymidine kinase gene of herpes simplex virus type 1," Proc Natl Acad Sci USA 78:1441-1445 (1981).
Wagner, "Gene inhibition using antisense oligodeoxynucleotides," Nature 372:333-335 (1994).
Wang et al., "A general approach for the use of oligonucleotide effectors to regulate the catalysis of RNA-cleaving ribozymes and DNAzymes," Nucleic Acids Res 30:1735-1742 (2002).
Wang et al., "A general strategy for effector-mediated control of RNA-cleaving ribozymes and DNA enzymes," J Mol Biol 318:33-43 (2002).
Watkins et al., "Metabolomics and biochemical profiling in drug discovery and development," Curr Opin Mol Ther 4:224-228 (2002).
Weiss et al., "Antisense RNA gene therapy for studying and modulating biological processes," Cell Mol Life Sci 55:334-358 (1999).
Werstuck et al., "Controlling gene expression in living cells through small molecule-RNA interactions," Science 282:296-298 (1998).
Wilda et al., "Killing of leukemic cells with a BCR/ABL fusion gene by RNA interference (RNAi)," Oncogene 21:5716-5724 (2002).
Wilson et al., "The interaction of intercalators and groove-binding agents with DNA triple-helical structures: the influence of ligand structure, DNA backbone modifications and sequence," J Mol Recognit 7:89-98 (1994).
Winkler et al., "An MRNA Structure That Controls Gene Expression by Binding FMN," *PNAS* 99(25)15908-15913 (2002).
Winkler et al., "Control of gene expression by a natural metabolite-responsive ribozyme," Nature 428:281-286 (2004).
Winkler et al., "Genetic Control by Metabolite-Binding Riboswitches," *ChemBioChem* 4:1024-1032 (2003).
Winkler et al., "Thiamine derivatives bind messenger RNAs directly to regulate bacterial gene expression," Nature 419:952-956 (2002).
Yamamoto et al., "Identification of a functional promoter in the long terminal repeat of Rous sarcoma virus," Cell 22:787-797 (1980).
Yelin et al., "Widespread occurrence of antisense transcription in the human genome," Nat Biotechnol 21:379-386 (2003).

(56) References Cited

OTHER PUBLICATIONS

Yen et al., "Exogenous control of mammalian gene expression through modulation of RNA self-cleavage," Nature 431:471-476 (2004).
Yu et al., "RNA interference by expression of short-interfering RNAs and hairpin RNAs in mammalian cells," Proc Natl Aced Sci USA 99:6047-6052 (2002).
Zaug et al., "A labile phosphodiester bond at the ligation junction in a circular intervening sequence RNA," Science 224:574-578 (1984).
Zaug et al., "The intervening sequence RNA of Tetrahymena is an enzyme," Science 231:470-475 (1986).
Zaug et al., "The Tetrahymena ribozyme acts like an RNA restriction endonuclease," Nature 324:429-433 (1986).
Zimmermann et al., "Interlocking structural motifs mediate molecular discrimination by a theophylline-binding RNA," Nat Struct Biol 4:644-649 (1997).
Zimmermann et al., "Molecular interactions and metal binding in the theophylline-binding core of an RNA aptamer," RNA 6:659-667 (2000).
Zon, "Oligonucleotide analogues as potential chemotherapeutic agents," Pharm Res 5:539-549 (1988).
Aagaard et al., "Engineering and optimization of the miR-1 06b cluster for ectopic expression of multiplexed anti-HIV RNAs," *Gene Ther.*, 15:1536-1549 (2008).
Aagard and Rossi, "RNAi Therapeutics: Principles, Prospects and Challenges," *Adv Drug Deliv Rev* 59(2- 3):75-86 (2007).
Abbas-Terki et al., "Lentiviral-mediated RNA interference," *Hum. Gene Ther.*, 13:2197-2201 (2002).
Amarzguioui et. al., "Tolerance for mutations and chemical modifications in a siRNA," *Nucleic Acid Research*, 31:589-595 (2003).
An et al., "Artificial control of gene expression in mammalian cells by modulating RNA interference through aptamer-small molecule interaction," *RNA*, 12(5):710-716 (2006).
Anderson et al., "Environmental signal integration by a modular AND gate," *Mol. Syst. Biol.*, 3:133 (2007).
Araki et al., "Allosteric regulation of a ribozyme activity through ligand-induced conformational change," *Nucleic Acids Research* 26(14): 3379-3384 (1998).
Baker et al., "Engineering life: building a Fab for biology," *Scientific American*, 294:44-51 (2006).
Bartlett and Davis, "Insights into the kinetics of siRNA-mediated gene silencing from live-cell and live-animal bioluminescent imaging," *Nucleic Acids Res.*, 34:322-333 (2006).
Basu et al., "Spatiotemporal control of gene expression with pulse-generating networks," *Proc. Natl. Acad. Sci. USA*, 101:6355-6360 (2004).
Bauer et al., "Engineered riboswitches as novel tools in molecular biology," *J. Biotechnology*, 124(1):4-11 (2006).
Bauer et al., "Prevention of interferon-stimulated gene expression using microRNA-designed hairpins," *Gene Ther.*, 16:142-147 (2009).
Baulcombe, "Diced defence," *Nature*, 409(6818):295-296 (2001).
Bayer et al., "Synthetic control of a fitness tradeoff in yeast nitrogen metabolism," *J. Biol. Eng.*, 3:1 (2009).
Beisel et al., "Design principles for riboswitch function," *PLoS Comp. Biol.*, 5:e1000363 (2009).
Beisel et al., "Model-guided design of ligand-regulated RNAi for programmable control of gene expression," *Molecular Systems Biology*, 4:224 (2008).
Benenson et al., "An autonomous molecular computer for logical control of gene expression," *Nature*, 429:423-429 (2004).
Benenson, "Small hairpin RNA as a small molecule sensor," *Mol. Sys. Biol.*, 4:227 (2008).
Berens et al., "Synthetic riboregulators—an alternative means to control gene expression," *Gene Therapy and Molecular Biology*, 9:417-422 (2005).
Berezovski et al., "Nonequilibrium Capillary Electropho esis of Equilibrium Mixtures: A Universal Tool for Development of Aptamers," *J. Am. Chem. Soc.*, 127:3165-3171 (2005).
Berge et al., "Pharmaceutical Salts," *J. of Pharm Sci.*, 66:1-19 (1977).

Biesecker et al, "Derivation of RNA aptamer inhibitors of human complement C5," *Immunopharmacology*, 42(1-3):219-230 (1999).
Birikh et al., "The structure, function and application of the hammerhead ribozyme," *Eur J Biochem* 245:1-16 (1997).
Blount and Uhlenbeck, "The structure-function dilemma of the hammerhead ribozyme," *Annu Rev Biophys Biomol Struct*, 34:415-440 (2005).
Boiziau et al. "DNA Aptamers Selected Against the HIV-1 trans-Activation-responsive RNA Element Form RNA-DNA Kissing Complexes," *J. Biol. Chem.*, 274(18):12730-12737 (1999).
Boiziau et al., "Identification of Aptamers Against the DNA Template for in Vitro Transcription of the HIV-1 TAR Element," *Antisense Nucleic Acid Drug Dev.*, 7(4):369-380 (1997).
Boudreau et al., "Artificial microRNAs as siRNA shuttles: Improved Safety as Compared to shRNAs In vitro and In vivo," *Mol. Ther.*, 17(1):169-175 (2009).
Breaker, "Complex riboswitches," *Science*, 319:1795-1797 (2008).
Breaker, "Engineered allosteric ribozymes as biosensor components," *Curr. Opin. Biotechnol.*, 13:31-39 (2002).
Brockstedt et al., "In vitro evolution of RNA aptamers recognizing carcinogenic aromatic amines," *Biochem. Biophys. Res. Commun.*, 313(4):1004-1008 (2004).
Brown et al., "Endogenous microRNA can be broadly exploited to regulate transgene expression according to tissue, lineage and differentiation state," *Nat. Biotechnol.*, 25:1457-1467 (2007).
Bunka and Stockley, "Aptamers come of age—at last," *Nat Rev Microbiol* 4:588-596 (2006).
Burke and Greathouse, "Low-magnesium, trans-cleavage activity by type III, tertiary stabilized hammerhead ribozymes with stem 1 discontinuities," *BMC Biochem* 6:14 (2005).
Burke et al., "RNA aptamers to the adenosine moiety of S-adenosyl methionine: structural inferences from variations on a theme and the reproducibility of SELEX," *Nucleic Acids Research*, 2510):2020-2024 (1997).
Buskirk et al., "Engineering a ligand-dependent RNA transcriptional activator," *Chem. Biol.*, 11:1157-1163 (2004).
Cai et al., "Human microRNAs are processed from capped, polyadenylated transcripts that can also function as mRNAs," *RNA*,10:1957-1966 (2004).
Calin et al., "MiR-15a and miR-16-1 cluster functions in human leukemia," *Proc. Natl. Acad. Sci. USA*,105:5166-5171 (2008).
Canny et al., "Fast cleavage kinetics of a natural hammerhead ribozyme," *J Am Chem Soc* 126(35):10848-10849 (2004).
Carmell et al., "RNase III enzymes and the initiation of gene silencing," *Nature Structural & Molecular Biology*, 11:214-218 (2004).
Chen et al., "Genetic control of mammalian T-cell proliferation with synthetic RNA regulatory systems," *Proc. Natl. Acad. Sci. USA*. 107: 8531-8536 (2010).
Chiu and Rana, "RNAi in Human Cells: Basic Structural and Functional Features of Small Interfering RNA," *Mol. Cell* 10:549-561 (2002).
Chiu and Rana, "siRNA function in RNAi: A chemical modification analysis," *RNA* 9:1034-1048 (2003).
Cox et al., "Programming gene expression with combinatorial promoters," *Mol. Syst. Biol.* 3:145 (2007).
Croft et al., "Is prokaryotic complexity limited by accelerated growth in regulatory overhead?" *Genome Biology* 5:P2 (2003).
Culler et al., "Functional selection and systematic analysis of intronic splicing elements identifies active sequence motifs and associated splicing factors," *Nuc. Acids Res.* 38:5152-5165 (2010).
Dambach, "Potential adverse effects associated with inhibition of p38a/β MAP kinases," *Curr. Top. Med. Chem.*, 5(10):929-939 (2005).
Daniels, "A tenascin-C aptamer identified by tumor cell SELEX: Systematic evolution of ligands by exponential enrichment," *PNAS*, 100(26):15416-15421 (2003).
Danilova et al., "RNAKinetics: a web server that models secondary structure kinetics of an elongating RNA," *J. Bioinform. Comput. Biol.*, 4:589-596 (2006).
Davidson et al., "Synthetic RNA circuits," *Nature Chemical Biology*, 31):23-28 (2007).

(56) References Cited

OTHER PUBLICATIONS

De La Pena et al., "Peripheral regions of natural hammerhead ribozymes greatly increase their self-cleavage activity," *Embo J.*, 22(20):5561-5570 (2003).
Deans et al., "A Tunable Genetic Switch Based on RNAi and Repressor Proteins for Regulating Gene Expression in Mammalian Cells," *Cell*, 130:363-372 (2007).
Desai et al., "Genetic screens and selections for small molecules based on a synthetic riboswitch that activates protein translation," *J. Am. Chem. Soc.*, 126:13247-13254 (2004).
Dirks et al., "Triggered amplification by hybridization chain reaction," *Proc. Natl. Acad. Sci. USA* 101:15275-15278 (2004).
Drabovich et al., "Selection of Smart Aptamers by Equilibrium Capillary Electrophoresis of Equilibrium Mixtures (ECEEM)," *J. Am. Chem. Soc.*, 127:11224-11225 (2005).
Duconge and Toulme, "In vitro selection identifies key determinants for loop-loop interactions: RNA aptamers selective for the TAR RNA element of HIV-1," *RNA*, 5:1605-1614 (1999).
Dueber et al., "Engineering synthetic signaling proteins with ultrasensitive input-output control," *Nat. Biotechnol.*, 25:660-662 (2007).
Elion, "The Ste5p scaffold," *J Cell Sci*, 114(22):3967-3978 (2001).
Elowitz and Leibler, "A synthetic oscillatory network of transcriptional regulators," *Nature*, 403:335-338 (2000).
Endy, "Foundations for engineering biology," *Nature* 438:449-453 (2005).
Eulberg et al., "Development of an automated in vitro selection protocol to obtain RNA-based aptamers: identification of a biostable substance P antagonist," *Nucleic Acids Res.*, 33(4):e45 (2005).
Fedor et al., "The catalytic diversity of RNAs," *Nat. Rev. Mol. Cell Biol.*, 6:399-412 (2005).
Flinders et al., "Recognition of planar and nonplanar ligands in the malachite green-RNA aptamer complex," *Chem. Biochem.*, 5(I):62-72 (2004).
Flotte, "Size does matter: overcoming the adeno-associated virus packaging limit," *Respiratory Research*, 1:16-18 (2000).
Friedman et al., "Most mammalian mRNAs are conserved targets of microRNAs," *Genome Res.* 19:92-105 (2009).
Fukusaki et al., "DNA aptamers that bind to chitin," *Bioorg. Med. Chem. Lett.*, 10(5):423-425 (2000).
Gardner et al., "Construction of a genetic toggle switch in *Escherichia coli*," *Nature*, 403:339-342 (2000).
Gebhardt, "RNA aptamers to s-adenosylhomocysteine: kinetic properties, divalent cation dependency, and comparison with anti-s-adenosyl homocysteine antibody," *Biochemistry*, 39(24):7255-7265 (2000).
Geiger et al., "RNA aptamers that bind L-arginine with sub-micromolar dissociation constants and high enantioselectivity," *Nucleic Acids Research*, 24(6):1029-1036 (2000).
Gilbert et al., "RNA aptamers that specifically bind to a K Ras-derived farnesylated peptide," *Bioorg. Med. Chem.*, 5(6):1115-1122 (1997).
Gopinath et al., "An efficient RNA aptamer against human influenza B virus hemagglutinin," *J. Biochem.* (Tokyo), 139(5):837-846 (2006).
Gossen and Bujard, "Tight control of gene expression in mammalian cells by tetracycline-responsive promoters," *Proc Natl Acad Sci USA* 89:5547-5551 (1992).
Grassi et al., "Cleavage of collagen RNA transcripts by hammerhead ribozymes in vitro is mutation-specific and shows competitive binding effects," *Nucleic Acids Res* 25(17):3451-3458 (1997).
Grate and Wilson, "Inducible regulation of the *S. cerevisiae* cell cycle mediated by an RNA aptamer-ligand complex," *Bioorg. Med. Chem.*, 9:2565-2570 (2001).
Gregory et al., "The Microprocessor complex mediates the genesis of microRNAs," *Nature*, 432:235-240 (2004).
Gregory et al., "Human RISC couples microRNA biogenesis and posttranscriptional gene silencing," *Cell*, 123:631-640 (2005).
Grieger and Samulski, "Packaging capacity of adeno-associated virus serotypes: impact of larger genomes on infectivity and postentry steps," *J. Virol.*, 79:9933-9944 (2005).
Griffiths-Jones et al., "miRBase: microRNA sequences, targets and gene nomenclature," *Nucleic Acids Res.*, 34:D140-144 (2006).
Griffiths-Jones, "The microRNA Registry," *Nucleic Acids Res.*, 32:D109-111 (2004).
Grimm et al., "Fatality in mice due to oversaturation of cellular microRNA/short hairpin RNA pathways," *Nature*, 441:537-541 (2006).
Grundy and Henkin, "From ribosome to riboswitch: control of gene expression in bacteria by RNA structural rearrangements," *Crit. Rev. Biochem. Mol. Biol.*, 41:329-338 (2006).
Guet et al., "Combinatorial synthesis of genetic networks," *Science*, 296:1466-1470 (2002).
Guil et al., "The multifunctional RNA-binding protein hnRNP A1 is required for processing of miR-18a," *Nat. Struct. Mol. Biol.*, 14:591-596 (2007).
Hall et al., "Computational selection of nucleic acid biosensors via a slip structure model," *Biosens. Bioelectron.*, 22:1939-1947 (2007).
Haller et al., "In vitro selection of a 7-methyl-guanosine binding RNA that inhibits translation of capped mRNA molecules," *PNAS*, 94:8521-8526 (1997).
Hamada et al., "Effects on RNA Interference in Gene Expression (RNAi) in Cultured Mammalian Cells of Mismatches and the Introduction of Chemical Modifications at the 3'-Ends of siRNAs," *Antisense Nucleic Acid Drug Dev.*, 12(5):301-309 (2002).
Hammann et al., "Dissection of the ion-induced folding of the hammerhead ribozyme using 19F NMR," *Proc Natl Acad Sci USA* 98(10):5503-5508 (2001).
Hammond et al., "Argonaute2, a Link Between Genetic and Biochemical Analyses of RNAi," *Science*, 293(5532):1146-1150 (2001).
Han et al., "Molecular basis for the recognition of primary microRNAs by the Drosha-DGCR8 complex," *Cell*, 125:887-901 (2006).
Han et al., "Posttranscriptional crossregulation between Drosha and DGCR8," *Cell*, 136:75-84 (2009).
Han et al., "The Drosha-DGCR8 complex in primary microRNA processing," *Genes Dev.*, 18:3016-3027 (2004).
Hanahan and Weinberg, "The Hallmarks of Cancer," *Cell*, 100(1):57-70 (2000).
Hanson et al., "Tetracycline-aptamer-mediated translational regulation in yeast," *Mol Microbiol* 49(6):1627-1637 (2003).
Harborth et al., "Sequence, Chemical, and Structural Variation of Small Interfering RNAs and Short Hairpin RNAs and the Effect on Mammalian Gene Silencing,"*Antisense Nucleic Acid Drug Dev.*, 13(2):83-105 (2003).
Hawkins et al., "Production of benzylisoquinoline alkaloids in *Saccharomyces cerevisiae*," *Nat. Chem. Biol.*, 4:564-573 (2008).
Hawkins et al., "The regulatory roles of the galactose permease and kinase in the induction response of the GAL network in *Saccharomyces cerevisiae*," *J. Biol. Chem.*, 281:13485-13492 (2006).
Hebert et al., "Loss of microRNA cluster miR-29a-b-1 in sporadic Alzheimer's disease correlates with increased BACE1-13-secretase expression," *Proc. Natl. Acad. Sci. USA*, 105:6415-6420 (2008).
Hesselberth et al., "In Vitro Selection of RNA Molecules That Inhibit the Activity of Ricin A-chain," *J. Biol. Chem.*, 275(7):4937-4942 (2000).
Hicke et al., "Tenascin-C Aptamers Are Generated Using Tumor Cells and Purified Protein," *J. Biol. Chem.*, 276(52):48644-4854 (2001).
Hirao et al., "RNA Aptamers That Bind to and Inhibit the Ribosome-inactivating Protein, Pepocin," *J. Biol. Chem.*, 275(7): 4943-4948 (2000).
Hoff et al., "Fluorescence detection of a protein-bound 2Fe2S cluster," *ChemBioChem*, 10:667-670 (2009).
Hoff et al., "In vivo fluorescent detection of Fe-S clusters coordinated by human GRX2," *Chem. Biol.*, 16:1299-1308 (2009).
Hooshangi et al., "Ultrasensitivity and noise propagation in a synthetic transcriptional cascade," *Proc. Natl. Acad. Sci. USA*, 102:3581-3586 (2005).
Hornung et al., "In vitro selected RNA molecules that bind to elongation factor Tu," *Biochemistry*, 37:7260-7267 (1998).

(56) References Cited

OTHER PUBLICATIONS

Huang and Ferrell, "Ultrasensitivity in the mitogen-activated protein kinase cascade," *Proc. Natl. Acad. Sci. USA*, 93:10078-10083 (1996).
Hutvagner et al., "Sequence-specific inhibition of small RNA function," *PLoS Biol.*, 2:E98 (2004).
Hwang et al., "A Hexanucleotide Element Directs MicroRNA Nuclear Import," *Science*, 315:97-100 (2007).
International Search Report in International Application No. PCT/US07/84364 (Aug. 19, 2008).
Isaacs et al., "RNA synthetic biology," *Nature Biotechnology*, 24(5):545-554 (2006).
Isaacs et al., "Plug and play with RNA," *Nat. Biotech.*, 23:306-307 (2005).
Javaherian et al., "Selection of aptamers for a protein target in cell lysate and their application to protein purification," *Nucleic Acids Research*, 37( 8):e62:1-10 (2009).
Jenison et al., "High-resolution molecular discrimination by RNA," *Science* (1994) 263:1425-1429.
Jeong et al., "In vitro selection of the RNA aptamer against the Sialyl Lewis X and its inhibition of the cell adhesion," *Biochem. Biophys. Res. Comm.*, 281(I):237-243 (2001).
Kato et al., "In vitro selection of DNA aptamers which bind to cholic acid," *Biochim. Biophys. Acta*, 1493(1-2):12-8 (2000).
Keasling, "From yeast to alkaloids," *Nat. Chem. Biol.*, 4:524-525 (2008).
Kedde et al., "RNA-binding protein DND1 inhibits microRNA access to target mRNA," *Cell*, 131:1273-1286 (2007).
Ketting et al., "Dicer functions in RNA interference and in synthesis of small RNA involved in developmental timing in *C. elegans*," *Genes Dev.*, 15:2654-2659 (2001).
Khvorova et al., "Sequence elements outside the hammerhead ribozyme catalytic core enable intracellular activity," *Nat. Struct. Biol.*, 10:708-872 (2003).
Kiga et al., "An RNA aptamer to the xanthine-guanine base with a distinctive mode of purine recognition," *Nucleic Acids Res.*, 26:1755-1760 (1998).
Kim et al., "An artificial riboswitch for controlling pre-mRNA splicing," *RNA*, 11:1667-1677 (2005).
Kim et al., "Synthetic dsRNA Dicer substrates enhance RNAi potency and efficacy," *Nature Biotech.*, 23:222-226 (2008).
Kimoto et al., "Anti-(Raf-1) RNA aptamers that inhibit Ras-induced Raf-1 activation," *Eur. J. Biochem.*, 269(2):697-704 (2002).
Kimoto et al., "RNA aptamers that specifically bind to the Ras-binding domain of Raf-1," *FEBS Lett.*, 441(2): 322-326 (1998).
Koizumi et al., "Molecular recognition of cAMP by an RNA aptamer," *Biochemistry*, 39(30):8983-8992 (2000).
Kok et al., "Human TRBP and PACT directly interact with each other and associate with dicer to facilitate the production of small interfering RNA," *J. Biol. Chem.*, 282:17649-17657 (2007).
Kramer et al., "BioLogic gates enable logical transcription control in mammalian cells," *Biotechnol. Bioeng.*, 87:478-484 (2004).
Kraus et al., "Cutting Edge: Novel RNA Ligands Able to Bind CD4 Antigen and Inhibit CD4+ T Lymphocyte Function," *J. Immunol.*, 160(II):5209-5212 (1998).
Lee et al., "In vitro and in vivo assays for the activity of Drosha complex," *Methods Enzymol.*, 427:89-106 (2007).
Lee et al., "MicroRNA maturation: stepwise processing and subcellular localization," *EMBO J.*, 21(17):4663-4670 (2002).
Lee et al., "The nuclear RNase III Drosha initiates microRNA processing," *Nature*, 425:415-419 (2003).
Lee et al., "Aptamer database," *Nucl. Acids Res.*, 32:D95-D100 (2004).
Lee et al., "The role of PACT in the RNA silencing pathway," *EMBO J.*, 25:522-532 (2006).
Legiewicz et al., "A More Complex Isoleucine Aptamer with a Cognate Triplet," *J. Biol. Chem.*, 280(20):19815-19822 (2005).
Lescoute and Westhof, Topology of three-way junctions in folded RNAs, *RNA* 12: 83-93, 2006.
Levine et al., "Quantitative Characteristics of Gene Regulation by Small RNA," *PLoS Biol.*, 5(e229):1998-2010 (2007).
Li and Breaker, "Kinetics of RNA Degradation by Specific Base Catalysis of Transesterification Involving the 2'-Hydroxyl Group," *J. Am. Chem. Soc.*, 121: =5364-5372 (1999).
Liu et al., "Soafenib blocks the RAF/MEK/ERK pathway, inhibits tumor angiogenesis, and induces tumor cell apoptosis in hepatocellular carcinoma model PLC/PRF/5," *Cancer Res* 66(24):11851-11858 (2006).
Liu et al., "RNA aptamers specific for bovine thrombin," *J. Mol. Recog.*, 16(I):23-27 (2003).
Long and Uhlenbeck, "Self-cleaving catalytic RNA," *Faseb J* 7(1):25-30 (1993).
Lozupone et al., "Selection of the simplest RNA that binds isoleucine," *RNA*, 9(II):1315-1322 (2003).
Lutz and Bujard, "Independent and tight regulation of transcriptional units in *Escherichia coli* via the LacR/O, the TetR/O and AraC/$I_1$-$I_2$ regulatory elements," *Nucleic Acids Res* 25(6):1203-1210 (1997).
Lynch et al., "A high-throughput screen for synthetic riboswitches reveals mechanistic insights into their function," *Chem. Biol.*, 14(2):173-184 (2007).
MacRae et al., "Structural Basis for Double-Stranded RNA Processing by Dicer," *Science*, 311( 5758):195-198 (2006).
Malphettes and Fussenegger, "Impact of RNA interference on gene networks," *Metab. Eng.*, 8:672-683 (2006).
Mandal et al., "A glycine-dependent riboswitch that uses cooperative binding to control gene expression," *Science*, 306:275-279 (2004).
Mandal and Breaker, "Gene regulation by riboswitches," *Natl Rev Mol Cell Biol* 5:451-463 (2004).
Marschall et al., "Inhibition of gene expression with ribozymes," *Cell Mol Neurobiol* 14(5):523-538 (1994).
Martin et al., "Redesigning cells for the production of complex organic molecules," *ASM News*, 68:336-343 (2002).
Mathews et al., "Prediction of RNA secondary structure by free energy minimization," *Curr. Opin. Struct. Biol.*, 16:270-278 (2006).
Matranga et al., "Passenger-strand cleavage facilitates assembly of siRNA into Ag02-containing RNAi enzyme complexes," *Cell*, 123:607-620 (2005).
McBride et al., "Artificial miRNAs mitigate shRNA-mediated toxicity in the brain: Implications for the therapeutic development of RNAi," *PNAS*, 105:5868 (2008).
McCormick, F., "Signalling Networks that Cause Cancer," *Trends Cell Biol*, 9(12):M53-M56 (1999).
Meister, "Sequence-specific inhibition of microRNA- and siRNA-induced RNA silencing," *RNA*, 10:544-550 (2004).
Mendonsa and Bowser., "In Vitro Evolution of Functional DNA Using Capillary Electrophoresis," *J. Am. Chem. Soc.*, 126:20-21 (2004).
Mendonsa and Bowser, "In Vitro Selection of Aptamers with Affinity for Neuropeptide Y Using D Capillary Electrophoresis," J. Am. Chem. Soc., 127:9382-9383 (2005).
Mendonsa and Bowser, "In Vitro Selection of High-Affinity DNA Ligands for Human IgE Using Capillary Electrophoresis," *Anal. Chem.*, 76:5387-5392 (2004).
Misono et al., "Selection of RNA aptamers against human influenza virus hemagglutinin using surface plasmon resonance," *Anal. Biochem.*, 342(2):312-317 (2005).
Muller et al., "Thermodynamic characterization of an engineered tetracycline-binding riboswitch," *Nucleic Acids Res.*, 34(9):2607-2617 (2006).
Ng and Abelson, "Isolation and sequence of the gene for actin in *Saccharomyces cerevisiae*," *Proc Natl Acad Sci USA* 77(7):3912-3916 (1980).
Nickols et al., "Suppression of androgen receptor-mediated gene expression by a sequence-specific DNA-binding polyamide," *Proc. Natl. Acad. Sci. USA*, 104:10418-10423 (2007).
Nishiwaki et al., "Structure of the yeast HIS5 gene responsive to general control of amino acid biosynthesis," Mol Gen Genet 208:159-167 (1987).
Novina et al., "The RNAi revolution," *Nature*, 430(6996):161-164 (2004).
Ogawa and Maeda, "An artificial aptazyme-based riboswitch and its cascading system in *E. coli*," *Chembiochem.*, 9:206-209 (2008).

(56) References Cited

OTHER PUBLICATIONS

Ogawa et al., "Purification, Characterization, and Gene Cloning of Purine Nucleosidase from *Ochrobactrum anthropi*," *Appl Environ Microbiol* 67(1):1783-1787 (2001).
Ohrt et al., "Fluorescence correlation spectroscopy and fluorescence cross-correlation spectroscopy reveal the cytoplasmic origination of loaded nuclear RISC in vivo in human cells," *Nucleic Acids Res.*, 36(20):6439-6449 (2008).
Osborne et al., "Nucleic Acid Selection and the Challenge of Combinatorial Chemistry," *Chem. Rev.*, 97:349-370 (1997).
Pan et al., "A self-processing ribozyme cassette: utility against human papillomavirus 11 E6/E7 mRNA and hepatitis B virus," *Mol Ther* 9(4):596-606 (2004).
Parisien et al., "The MC-Fold and MC-Sym pipeline infers RNA structure from sequence data," *Nature*, 452:51-55 (2008).
Park et al., "Rewiring MAP kinase pathways using alternative scaffold assembly mechanisms," *Science* 299:1061-1064 (2003).
Pelletier and Sonenberg, "Insertion mutagenesis to increase secondary structure within the 5' noncoding region of a eukaryotic mRNA reduces translational efficiency," *Cell* 40:515-526 (1985).
Penchovsky et al., "Computational design and experimental validation of oligonucleotide-sensing allosteric ribozymes," *Nat. Biotechnol.*, 23:1424-1433 (2005).
Penedo et al., "Folding of the natural hammerhead ribozyme is enhanced by interaction of auxiliary elements," *RNA* 10(5):880-888 (2004).
Pfleger et al., "Combinatorial engineering of intergenic regions in operons tunes expression of multiple genes," *Nat. Biotech.*, 24:1027-1032 (2006).
Pley et al, "Three-dimensional structure of a hammerhead ribozyme," *Nature* 372:68-74 (1994).
Qi and Elion, "MAP Kinase Pathways," *J Cell Sci*, 118(16):3569-3571 (2005).
Raab and Stephanopoulos, "Dynamics of gene silencing by RNA interference," *Biotechnol. Bioeng.*, 88:121-132 (2004).
Rand et al., "Argonaute2 cleaves the anti-guide strand of siRNA during RISC activation," *Cell*, 123:621-629 (2005).
Rinaudo et al., "A universal RNAi-based logic evaluator that operates in mammalian cells," *Nat. Biotechnol.*, 25:795-801 (2007).
Robertson et al., "In vitro selection of an allosteric ribozyme that transduces analytes to amplicons," *Nat. Biotechnol.*, 17:62-66 (1999).
Rodionov et al., "Reconstruction of regulatory and metabolic pathways in metal-reducing-proteobacteria," *Genome Biol.*, 5:R90.1-R90.27 (2004).
Rossi, "Targeted cleavage: Tuneable cis-cleaving ribozymes," *PNAS*, 104(38):14881-14882 (2007).
Roychowdhury-Saha et al., "Flavin recognition by an RNA aptamer targeted toward FAD," *Biochemistry*, 41(8):2492-2499 (2002).
Ruckman et al., "2'-Fluoropyrimidine RNA-based Aptamers to the 165-Amino Acid Form of Vascular Endothelial Growth Factor (VEGF165)," *J. Biol. Chem.*, 273(32):20556-20567 (1998).
Rusconi et al., "Blocking the initiation of coagulation by RNA aptamers to factor VIIa," *Thromb. Haemost.*, 84(5):841-848 (2000).
Saksmerprome et al., "Artificial tertiary motifs stabilizing trans-cleaving hammerhead ribozymes under conditions of submillimolar divalent ions and high temperatures," *RNA* 10(12):1916-1924 (2004).
Salehi-Ashtiani and Szostak, "In vitro evolution suggests multiple origins for the hammerhead ribozyme," *Nature* 414:82-84 (2001).
Saran et al., "The tyranny of adenosine recognition among RNA aptamers to coenzyme A," *BMC Evol. Biol.*, 3(I):26 (2003).
Sarin et al., "Inhibition of acquired immunodeficiency syndrome virus by oligodeoxynucleoside methylphosphonates," *Proc. Natl. Acad. Sci. USA*, 85:7448-7451 (1988).
Scherr et al., "Specific hammerhead ribozyme-mediated cleavage of mutant N-ras mRNA in vitro and ex vivo," *J Biol Chem* 272(22):14304-14313 (1997).
Schneider et al., "Selective enrichment of RNA species for tight binding to *Escherichia coli* rho factor," *FASEB J.*, 7(I):201-207 (1993).

Schwarz et. al., Evidence that siRNAs Function as Guides, Not Primers, in the *Drosophila* and Human RNAi Pathways, Mol. Cell 10: 537-548, 2002.
Seelig et al, Enzyme-Free Nucleic Acid Logic Circuits, *Science* 314: 1585-1588, 2006.
Shalgi et al., "Global and Local Architecture of the Mammalian microRNA-Transcription Factor Regulatory Network," *PLoS Comput. Biol.*, 3(7):e131 (2007).
Shapiro et al., "RNA computing in a living cell," *Science*, 322:387-388 (2008).
Shapiro, "Discovering New MPA Kinase Inhibitors," *Chem Biol* 13(8):807-809 (2006).
Smolke et al., "Molecular Switches for Cellular Sensors," *Engineering & Science*, 67(4):28-37 (2005).
Smolke et al., "Controlling the metabolic flux through the carotenoid pathway using directed mRNA processing and stabilization," *Met. Eng.*, 3: 313-321 (2001).
Smolke et al., "Effect of copy number and mRNA processing and stabilization on transcript and protein levels from an engineered dual-gene operon," *Biotech. Bioeng.*, 78: 412-424 (2002).
Smolke et al., "Effect of gene location, mRNA secondary structures, and RNase sites on expression of two genes in an engineered operon," *Biotech. Bioeng.*, 80:762-776 (2002).
Smolke et al., "Effects of transcription induction homogeneity and transcript stability on expression of two genes in a constructed operon," *Appl. Micro. Biotech.*, 57:689-696 (2001).
Smolke, "Building outside of the box: iGEM and the BioBricks Foundation," *Nat. Biotech.*, 27:1099-1102 (2009).
Smolke, "It's the DNA that counts," *Science*, 324:1156-1157 (2009).
Sontheimer, "Assembly and Function of RNA Silencing Complexes," *Nat. Rev. Mol. Cell. Biol.*, 6(2):127-138 (2005).
Soukup and Breaker, "Engineering precision RNA molecular switches," *Proc Natl Acad Sci USA* 96:3584-3589 (1999).
Soukup and Breaker, "Relationship between internucleotide linkage geometry and the stability of RNA," *RNA*, 5:1308-1325 (1999).
Soukup and Soukup, "Riboswitches exert genetic control through metabolite-induced conformational change," *Current Opinions in Structural Biology*, 14:344 (2004).
Stein et al., "Physicochemical properties of phosphorothioate oligodeoxynucleotides," *Nucl. Acids Res.*, 16:3209-3221 (1988).
Stern et al., "A system for Cre regulated RNA interference in vivo," *Proc. Natl. Acad. Sci. USA*, 105:13895-13900 (2008).
Stojanovic et al., "Modular aptameric sensors," *J Am Chem Soc* 126:9266-9270 (2004).
Stojanovic et al., "A deoxyribozyme-based molecular automaton," *Nat. Biotechnol.*, 21:1069-1074 (2003).
Sudarsan et al., "Tandem riboswitch architectures exhibit complex gene control functions," *Science*, 314(5797):300-304 (2006).
Sudarsan et al., "Metabolite-binding RNA domains are present in the genes of eukaryotes," *RNA*, 9:644-647 (2003).
Suel et al., "Tunability and noise dependence in differentiation dynamics," *Science*, 315:1716-1719 (2007).
Suess et al., "A theophylline responsive riboswitch based on helix slipping controls gene expression in vivo," *Nucleic Acids Research*, 32(4):1610-1614 (2004).
Suess et al., "Conditional gene expression by controlling translation with tetracycline-binding aptamers," *Nucleic Acids Res.*, 31:1853-1858 (2003).
Suess et al., "Engineered riboswitches: overview, problems and trends," *RNA Biol.*, 5(1):1-6 (2008).
Sun et al., "Multi-miRNA hairpin method that improves gene knockdown efficiency and provides linked multi-gene knockdown," *Biotechniques*, 41:59-63 (2006).
Tahiri-Alaoui et al., "High affinity nucleic acid aptamers for streptavidin incorporated into bi-specific capture ligands," *Nucleic Acids Res.*, 30(10):e45 (2002).
Takeno et al., "Selection of an RNA Molecule that Specifically Inhibits the Protease Activity of Subtilisin," *J. Biochem.*, 125(6):1115-1119 (1999).
Tao et al., "Arginine-binding RNAs resembling tar identified by in vitro selection," *Biochemistry*, 35(7):2229-2238 (1996).
Thompson et al., "Group I aptazymes as genetic regulatory switches," *BMC Biotechnol.*, 2:21 (2002).

(56) References Cited

OTHER PUBLICATIONS

Tuerk et al., "RNA pseudoknots that inhibit human immunodeficiency virus type 1 reverse transcriptase," *Proc. Natl. Acad. Sci. USA*, 89:6988-6992 (1992).

Tuleuova et al., "Modulating endogenous gene expression of mammalian cells via RNA-small molecule interaction," *Biochem. Biophys. Res. Commun.*, 376:169-173 (2008).

Ulrich et al., "In vitro selection of RNA molecules that displace cocaine from the membrane-bound nicotinic acetylcholine receptor," *Proc. Natl. Acad. Sci. USA*, 95(24):14051-14056 (1998).

Urvil et al., "Selection of RNA aptamers that bind specifically to the NS3 protease of hepatitis C virus," *Eur. J. Biochem.*, 248(I):130-138 (1997).

Vaish et al., "A novel, modification-dependent ATP-binding aptamer selected from an RNA library incorporating a cationic functionality," *Biochemistry*, 42(29):8842-8851 (2003).

Ventura et al., "Targeted Deletion Reveals Essential and Overlapping Functions of the miR-17~92 Family of miRNA Clusters," *Cell*, 132:875-886 (2008).

Villemaire et al., "Reprogramming Alternative Pre-messenger RNA Splicing through the Use of Protein-binding Antisense Oligonucleotides," *Biol. Chem.*, 278(50):50031-50039 (2003).

Voigt, "Genetic parts to program bacteria," *Curr Opin Biotechnol* 17:548-557 (2006).

Wallace et al., "In vitro selection and characterization of streptomycin-binding RNAs: Recognition discrimination between antibiotics," *RNA*, 4(I):112-123 (1998).

Wang et al., "MicroRNA-based therapeutics for cancer," *BioDrugs*, 23:15-23 (2009).

Wang et al., "Recent patents on the identification and clinical application of microRNAs and target genes," *Recent Pat. DNA Gene Seq.*, 1:116-124 (2007).

Wang et al., "General and Specific Functions of Exonic Splicing Silencers in Splicing Control," *Molecular Cell*, 23:61-70 (2006).

Wang et al., "RNA molecules that specifically and stoichiometrically bind aminoglycoside antibiotics with high affinities," *Biochemistry*, 35(38):12338-12346 (1996).

Weigand and Suess, "Tetracycline aptamer-controlled regulation of pre-mRNA splicing in yeast," *Nucleic Acids Res.*, 35:4179-4185 (2007).

Weigand et al., "Screening for engineered neomycin riboswitches that control translation initiation," *RNA*, 14:89-97 (2008).

Weinberg and Rossi, "Comparative single-turnover kinetic analyses of trans-cleaving hammerhead ribozymes with naturally derived non-conserved sequence motifs," *FEBS Lett* 579(7):1619-1624 (2005).

Weinberg et al., "Effective anti-hepatitis B virus hammerhead ribozymes derived from multimeric precursors," *Oligonucleotides* 17(1):104-112 (2007).

Welz et al., "Ligand binding and gene control characteristics of tandem riboswitches in Bacillus anthracis," *RNA*, 13:573 (2007).

Westerhout and Berkhout, "A systematic analysis of the effect of target RNA structure on RNA interference," *Nucleic Acids Res.*, 35(13)4322-4330 (2007).

Wieland and Hartig, "Improved aptazyme design and in vivo screening enable riboswitching in bacteria," *Angew. Chem. Int. Ed. Eng.*, 147:2604-2607 (2008).

Wieland et al., "Artificial ribozyme switches containing natural riboswitch aptamer domains," *Angew. Chem. Int. Ed. Eng.*, 148:2715-2718 (2009).

Wieland M., et al., "Artificial riboswitches: synthetic mRNA-based regulators of gene expression." Chembiochem. 2008; 9:1873-1878.

Wilson et al., "In vitro selection of functional nucleic acids," *Annu. Rev. Biochem.*, 68:611-647 (1999).

Wilson et al., "Functional requirements for specific ligand recognition by a biotin-binding RNA pseudoknot," *Biochemistry*, 37:14410-14419 (1998).

Win et al., "A modular and extensible RNA-based gene-regulartory platform for engineering cellular function," *PNAS*, 104(36):14283-14288 (2007).

Win et al., "RNA as a Versatile and Powerful Platform for Engineering Genetic Regulatory Tools," *Biotechnol. Gen. Eng. Rev.*, 24:311-346 (2007).

Win et al., "Codeine-binding RNA aptamers and rapid determination of their binding constants using a direct coupling surface plasmon resonance assay," *Nuc. Acids Res.*, 34: 5670-5682 (2006).

Win et al., "Frameworks for programming biological function through RNA parts and devices," *Chem. Biol.*, 16:298-310 (2009).

Win et al., "Higher-order cellular information processing with synthetic RNA devices," *Science*, 322:456-460 (2008).

Woodside et al., "Nanomechanical measurements of the sequence-dependent folding landscapes of single nucleic acid hairpins," *Proc. Natl. Acad. Sci. USA*, 103:6190-6195 (2006).

Xia et al., "Multiple shRNAs expressed by an inducible pol II promoter can knock down the expression of multiple target genes," *Biotechniques*, 41:64-68 (2006).

Yang et al., "DNA ligands that bind tightly and selectively to cellobiose," *PNAS*, 95(10):5462-5467 (1998).

Yeom et al., "Characterization of DGCR8/Pasha, the essential cofactor for Drosha in primary miRNA processing," *Nucleic Acids Res.*, 34(16):4622-4629, (2006).

Yi et al., "Exportin-5 mediates the nuclear export of pre-microRNAs and short hairpin RNAs," *Genes Dev.*, 17:3011-3016 (2003).

Yi et al., "Overexpression of exportin 5 enhances RNA interference mediated by short hairpin RNAs and microRNAs," *RNA*, 11:220-226 (2005).

Yokobayashi et al., "Directed evolution of a genetic circuit," *Proc. Natl. Acad. Sci. USA*, 99:16587-16591 (2002).

Yunusov et al., "Kinetic capillary electrophoresis-based affinity screening of aptamer clones," *Anal. Chim. Acta.*, 631(1):102-107 (2009).

Zeng and Cullen, "Structural requirements for pre-microRNA binding and nuclear export by Exportin 5," *Nucleic Acids Res.*, 32(16):4776-4785 (2004).

Zeng et al., "Both natural and designed micro RNAs can inhibit the expression of cognate mRNAs when expressed in human cells," *Mol. Cell*, 9:1327-1333 (2002).

Zeng et al., "Efficient processing of primary microRNA hairpins by Drosha requires flanking nonstructured RNA sequences," *J. Biol. Chem.*, 280:27595-27603 (2005).

Zeng et al., "Recognition and cleavage of primary microRNA precursors by the nuclear processing enzyme Drosha," *EMBO J.*, 24:138-148 (2005).

Zeng et al., "Sequence requirements for micro RNA processing and function in human cells," *RNA*, 9:112-123 (2003).

Zhou et al., "Novel Dual Inhibitory Function Aptamer-sRNA Delivery System for HIV-1 Therapy," *Molecular Therapy*, 16:1481-1489 (2008).

\* cited by examiner

MULTIPLEX DETECTION AND QUANTIFICATION

CHIP - BASED OUTPUT vs.

GEL - BASED OUTPUT

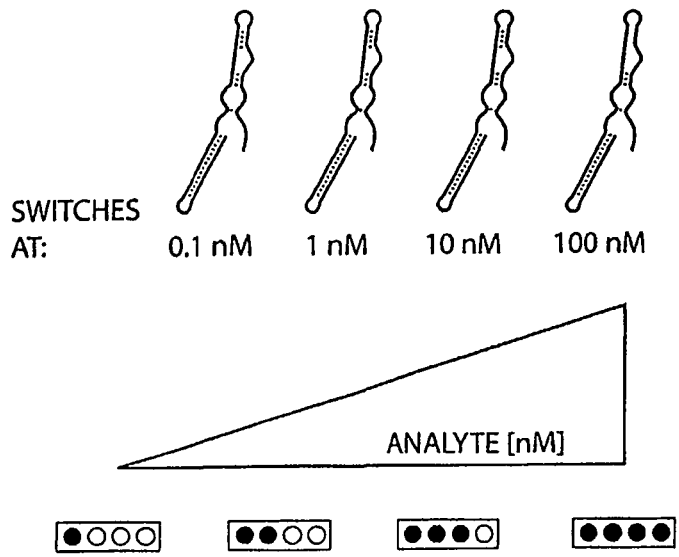
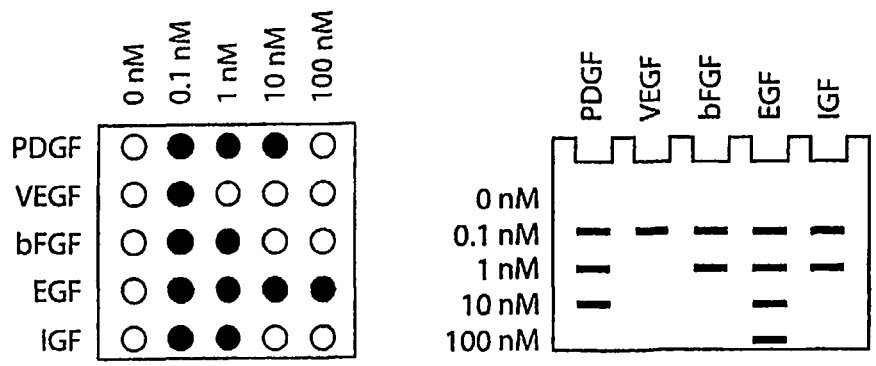
Fig. 10

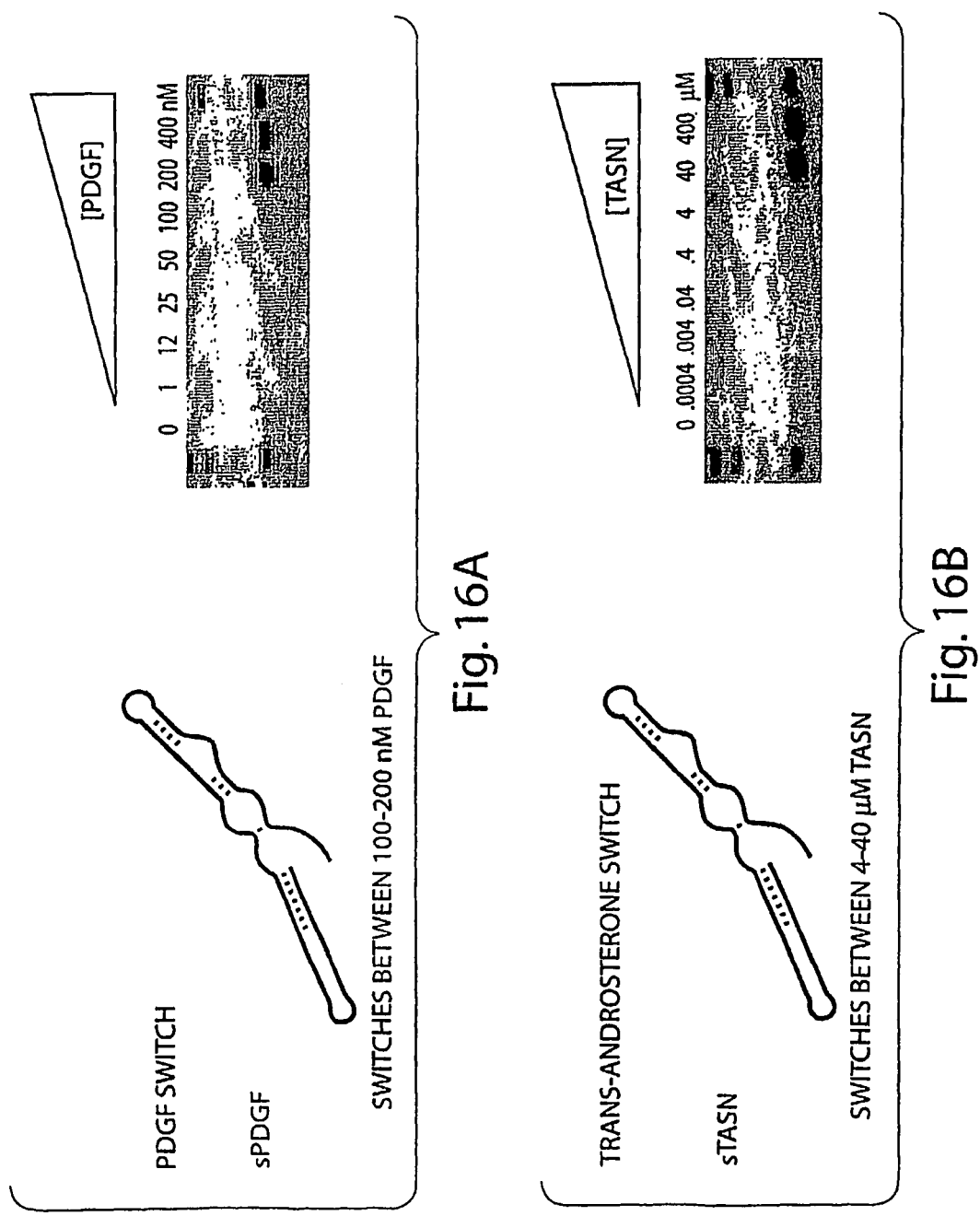

APTAMER REGULATED NUCLEIC ACIDS AND USES THEREOF

CROSS-REFERENCE TO RELATED APPLICATIONS

This application is a U.S. national stage filing under 35 U.S.C. §371 of International Application No. PCT/US2006/004801, filed on Feb. 9, 2006, which claims the benefit of the filing date under 35 U.S.C. §119(e) to U.S. Provisional Application No. 60/651,424, filed on Feb. 9, 2005; International Application No. PCT/US2006/004801 is also a continuation-in-part application of U.S. patent application Ser. No. 11/243,889, filed on Oct. 5, 2005, and a continuation-in-part application of International Application No. PCT/US2005/036161, which designates the U.S. and was filed on Oct. 5, 2005. Both U.S. Ser. No. 11/243,889 and International Application No. PCT/US2005/036161 claim the benefit of the filing date under 35 U.S.C. §119(e) to U.S. Provisional Application No. 60/641,658, filed on Jan. 6, 2005, and U.S. Provisional Application No. 60/615,977, filed on Oct. 5, 2004. International Application No. PCT/US2005/036161 and International Application No. PCT/US2006/004801 were both was published under PCT Article 21(2) in English. The contents of the above-referenced applications are incorporated herein by reference in their entirety.

BACKGROUND OF THE INVENTION

The detection of various target analytes or molecules is an important tool for a variety of applications including diagnostic medicine, molecular biology research and detection of contaminants or pathogens, to name a few. The detection methods differ according to the physical characteristics of each target molecule. For example, protein detection methods typically involve antibody-based immunoassays or mass spectrometry, whereas PCR-based assays may be more appropriate for nucleic acid detection.

The development of immunoassays and advances in methods of nucleic acid amplification have significantly advanced the art of the detection of biological analytes. In spite of these advances, nonspecific binding of the analyte to be detected and general assay noise has remained a problem that has limited the application and sensitivity of such assays.

Furthermore, while several methods for detecting different analytes have evolved, the ability to detect numerous target analytes simultaneously has proven difficult. Detection of multiple proteins, for example, has been limited to conventional electrophoresis assays or immunoassays. There has not been a significant multiplexed protein detection assay or method. Accordingly, there is a great need for analyte detection methods that are sensitive, specific, and readily amenable to multiplex detection.

Synthetic nucleic acid ligands, or aptamers, are versatile molecules useful in disease therapy and molecular medicine. Researchers have taken advantage of the relative ease with which RNA libraries can be generated and searched to create synthetic RNA-based molecules with novel functional properties. Aptamers are nucleic acid binding species that interact with high affinity and specificity to selected ligands. These molecules are generated through iterative cycles of selection and amplification known as in vitro selection or SELEX (Systematic Evolution of Ligands by EXponential enrichment) (Ellington et al., Nature 346, 818-22 (1990); and Tuerk et al., Science 249, 505-10 (1990)). Aptamers have been selected to bind diverse targets such as dyes, proteins, peptides, aromatic small molecules, antibiotics, and other biomolecules (Hermann et al., Science 287, 820-5 (2000)). High-throughput methods and laboratory automation have been developed to 10" generate aptamers in a rapid and parallel manner (Cox et al., Nucleic Acids Res 30, e108 (2002)). Researchers have demonstrated that aptamers can impart allosteric control properties onto other functional RNA molecules. Such allosteric control strategies have been employed to construct and select in vitro signaling aptamers, in vitro sensors, and in vitro allosterically controlled ribozymes (Jhaveri et al., Nat Biotechnol 18, 1293-7 (2000); Roth et al., Methods Mol Biol 252, 145-64 (2004); and Stojanovic et al., J Am Chem Soc 126, 9266-70 (2004)).

Aptamers present powerful tools for detecting analytes. However, there is a need to couple the capacity of aptamers to bind diverse target ligands with practical signal output methods that are typically associated with PCR, gel electrophoresis, or microarray assays.

SUMMARY OF THE INVENTION

The present invention provides aptamer-regulated nucleic acid sensors, or "ampliSwitches" herein. The subject ampliSwitches are a versatile class of nucleic acids that can be readily engineered to be responsive to a variety of ligands or analytes of interest, and are useful in many applications such as diagnostic applications. For example, ampliSwitches can be designed for use in hybridization-dependent detection assays in a ligand or analyte-dependent manner, and are therefore useful as sensors for detecting the presence, absence, or amount of a ligand or analyte of interest.

The aptamer-regulated nucleic acid sensor, or ampliSwitch, of the invention generally comprises a priming sequence domain that hybridizes to a nucleic acid target template in a sequence dependent manner, and an aptamer domain that binds to a ligand molecule (e.g., an analyte of interest) and induces an allosteric or conformational change in the ampliSwitch molecule so as to affect an activity or function of the primer sequence domain. For instance, binding of the ligand to the aptamer domain can cause a conformational change in the nucleic acid that alters the ability of the priming sequence to hybridize to a target template. The priming sequence domain can have at least two conformational states or configurations, an "off" state and an "on" state, defined by the priming sequence domain's ability or availability to interact with a target template. For example, the priming sequence domain can adopt a hairpin loop conformation in which the priming sequence is rendered unavailable to interact with its target template, and therefore, the hairpin loop conformation can be considered as at an "off" state and the corresponding ampliSwitch is "off." In this embodiment, an ampliSwitch that is "on" may have the priming sequence domain in an "on" configuration that allows it to interact with a target template, i.e., by being free to hybridize through intermolecular basepairing with a sequence in the target template; the ampliSwitch may switch from "off" to "on" in response to the presence of a ligand or analyte of interest that interacts with an aptamer domain of the ampliSwitch molecule, thereby causing a conformational change of one or more components of the ampliSwitch molecule that leads to the "on" configuration of the priming sequence domain.

A priming sequence domain of the invention can be switched between its "on" and "off" conformational states in response to interaction between a ligand or analyte and an aptamer domain. Aptamer-regulated nucleic acids, therefore, act as a switch whose activity is turned "on" and "off" in response to ligand or analyte binding. In certain embodiments, the priming sequence domain's activity is dependent on the presence or absence of the ligand or analyte of interest, and/or the amount or concentration of the ligand or analyte available to interact with the aptamer domain. In certain embodiments, an ampliSwitch operates in a binary fashion, alternating between "on" and "off" states depending on the presence or absence of a ligand or analyte of interest. In certain embodiments, an ampliSwitch operates in a tunable fashion, ranging between "on" and "off" states depending on the amount or concentration of a ligand or analyte of interest available to interact with an aptamer domain of the ampliSwitch molecule.

In certain embodiments, a subject ampliSwitch nucleic acid includes: (i) a priming sequence that hybridizes to a target template to form a primer:template pair, and (ii) an aptamer that binds to a ligand. Binding of the ligand to the aptamer causes a conformational change in the nucleic acid that alters the ability of the priming sequence to hybridize to the target template. In certain embodiments, the primer:template pair forms only in the presence of the ligand, and the priming sequence is a "ligand activated primer sequence." In other embodiments, the primer:template pair forms only in the absence of the ligand, and the priming sequence is a "ligand inactivated primer sequence." In certain embodiments, the primer:template pair forms only in the presence of the ligand at an amount or concentration greater than a threshold level, and the priming sequence is a "ligand activated primer sequence." In certain embodiments, the primer:template pair forms when the amount or concentration of the ligand is below a threshold level, and the priming sequence is a "ligand inactivated primer sequence."

To further exemplify, the ampliSwitch can be designed so that ligand binding to the aptamer causes a conformational change that renders the priming sequence available for hybridization to the target template, or can be designed so that ligand binding causes a conformational change that renders the primer sequence unavailable for hybridization to the target template. In certain embodiments, binding of the ligand to the aptamer causes a conformational change in the nucleic acid that alters the stability of the duplex formed by the primer sequence stem, which renders the primer sequence available or unavailable for hybridization to the target template.

To further illustrate, a conformational change can be one that produces or removes an intramolecular double-stranded feature (which includes the primer sequence), where the double-stranded feature alters the availability of the priming sequence to hybridize to its target template. In another illustration, a conformational change can be one that alters the ability of the priming sequence to form an intermolecular double-stranded feature with its target template.

In certain embodiments, hybridization of the priming sequence to its target template forms a primer:template pair that can be a substrate for an extrinsic enzymatic activity. For example, the primer:template pair may be a substrate for a DNA polymerase (e.g., taq polymerase or phi29) in a primer extension reaction. The primer extension reaction generates an extension product that is complementary to the target template. In certain embodiments, the primer:template pair is a substrate in a primer extension reaction such as in polymerase chain reaction (PCR), strand displacement amplification (SDA), rolling circle amplification (RCA), ligase chain reaction, nucleic acid sequence-based amplification (NASBA), or transcription-mediated amplification. In certain other embodiments, the primer:template pair acts as a substrate for a DNA ligase.

A nucleic acid ampliSwitch molecule of the invention may comprise deoxyribonucleic acid (DNA), or a ribonucleic acid (RNA), or both. Likewise, the invention also provides for expression constructs useful for producing a subject ampliSwitch that include (i) a coding sequence which, when transcribed, produces an ampliSwitch in an expression system, such as for example a host cell, and (ii) one or more transcriptional regulatory sequences that regulate transcription of the coding sequence for the ampliSwitch in an expression system containing the expression construct. An expression construct may include an expression vector. Examples of expression vectors include, for example, episomal expression vectors, integrative expression vectors, and viral expression vectors.

The subject ampliSwitch constructs can be derived from various nucleotides and nucleotide analogs, as well as utilizing various linkage chemistries. For example, the ampliSwitch can include one or more non-naturally occurring nucleoside analogs and/or one or more non-naturally occurring backbone linkers between nucleoside residues. Such analogs and linkers can be used to alter the stability, nuclease susceptibility (or resistance) and/or bioavailability (such as cell permeability) relative to a corresponding nucleic acid of naturally occurring nucleosides and phosphate backbone linkers.

In certain embodiments, a subject ampliSwitch nucleic acid comprises 30-500 nucleotides, more preferably 40-400 nucleotides, more preferably 50-300 nucleotides, and more preferably 100-200 nucleotides.

The ampliSwitch molecules of the present invention can be applied to detecting a vast number of ligands or analytes of interest with which one or more aptamers can be designed and/or selected to interact.

A ligand or analyte of interest of the present invention can be a nucleic acid, a nucleic acid analog, a peptide, a peptide analog (e.g., a peptidomimetic), a small molecule, a natural product.

In certain embodiments, the ligand is a nucleic acid, such as for example a gene transcript. To illustrate, an ampliSwitch molecule of the invention that includes an aptamer domain capable of interacting with and/or responding to a ligand that is a gene transcript is useful in determining the gene activity, e.g., expressed or not in a cell.

In certain embodiments, the ligand is a natural product. A natural product may include any one of the following: polypeptides (used interchangeably herein with "peptides" or "proteins"), nucleic acids, carbohydrates, fatty acids and lipids, non-peptide hormones (such as steroids), metabolic precursors or products thereof, signal transduction agents, such as second messenger molecules or post-translationally modified proteins. A protein natural product can be a growth factor, a receptor (e.g., a epidermal growth factor (EGF) receptor, or a Her2 receptor), a cytokine, an antigen (e.g., a tumor antigen, or an antigen of an infectious agent such as for example a virus, a bacterium, a fungus, or a prion), or an antibody (e.g., an antibody against an antigen of an infectious agent) to merely illustrate. To further illustrate, an ampliSwitch molecule of the invention that includes an aptamer domain capable of interacting with and/or responding to a ligand that is an antigen of an infectious agent (e.g., a surface antigen of a virus) is useful for detecting the presence and/or determining the amount of the infectious agent in a sample (e.g., a serum sample, a blood sample, or a urine sample). Accordingly, the ampliSwitch molecules can be useful diagnostic tools.

In certain embodiments, the ligand can be an enzyme cofactor, an enzyme substrate or a product of an enzyme-mediated reaction. To illustrate, an ampliSwitch molecule of the invention that includes an aptamer domain capable of interacting with and/or responding to a ligand that is a product of an enzyme-mediated reaction is useful in determining the enzyme's activity.

In certain instances, the ligand is a small molecule having a molecular weight less than 3500 amu. These can be naturally or non-naturally occurring molecules, including peptides, small organic molecules (including drugs and certain metabolites and intermediates, cofactors, etc), and metal ions. To illustrate, an ampliSwitch molecule of the invention that includes an aptamer domain capable of interacting with and/or responding to a small molecule ligand that is a metabolite or intermediate of a drug is useful for pharmacokinetics, bioavailability, and bioequivalence studies of the drug.

Certain embodiments provide methods of designing and selecting aptamers or aptamer domains that are responsive to one or more pre-selected or pre-determined ligands or analytes of interest. AmpliSwitches may also be "tuned" so that their switching behavior is more or less responsive to ligand binding. Similarly, ampliSwitches may be "tuned" so that the binding affinity of the aptamer domain is more or less sensitive to its ligand. For instance, the thermodynamic properties of intramolecular duplex formation and other secondary and tertiary structures in the ampliSwitch may be altered so that the aptamer domain is more or less amenable to ligand binding, i.e., such as may be manifest in the dissociation constant ($K_d$) or other kinetic parameters (such as $k_{on}$ and $k_{off}$ rates). Alternatively, allosteric changes in the priming sequence domain may be more or less responsive to ligand binding upon alterations in hybridization and other intramolecular interactions that may effect secondary and tertiary structures of the ampliSwitch. Forward engineering strategies for altering the thermodynamic properties of nucleic acid structures are well known in the art. For instance, increased complementary nucleic acid pairing may increase the stability of a priming sequence or aptamer domain. It is anticipated that the absolute and relative stabilities of the primer sequence domain stem and the aptamer stem will be important design parameters in tuning the switch behavior of an ampliSwitch.

In certain other embodiments, the aptamer domain of an ampliSwitch is responsive to other environmental changes. Environmental changes include, but are not limited, to changes in pH, temperature, osmolarity, or salt concentration.

In certain embodiments, an ampliSwitch molecule comprises multiple modular components, e.g., one or more aptamer domains and/or one or more priming sequence domains. In other embodiments, an ampliSwitch of the invention interacts with and responds to multiple ligands. For instance, an ampliSwitch molecule may comprise an aptamer domain that responds to multiple ligands, or may comprise two or more aptamer domains that each aptamer domain responds to a ligand. Optionally, one or more priming sequence domains are modulated by the one or more aptamer domains that respond to multiple ligands. In a specific aspect, a cooperative ligand controlled nucleic acid is provided, wherein multiple ligands sequentially bind to multiple aptamer domains to allosterically regulate one or more priming sequence domains. AmpliSwitches comprising multiple modular components are useful for detecting multiple analytes in a sample, either sequentially or simultaneously.

In certain embodiments, an ampliSwitch molecule further comprises a functional group or a functional agent, e.g., an intercalator or an alkylating agent.

Still another aspect of the present invention relates to cells which include one or more ampliSwitches of the present invention, or which have been engineered with one or more expression constructs, such as for example an expression vector comprising a coding sequence corresponding to one or more ampliSwitch nucleic acids, for producing ampliSwitch molecules in the cell.

The subject ampliSwitch nucleic acids have many useful applications, some of which are illustrated above. Generally, the present invention contemplates a method for detecting the presence and/or amount of a ligand or analyte of interest in a sample. The method involves forming a mixture that includes the sample, a target template, and an ampliSwitch nucleic acid comprising, for example, (i) a priming sequence that hybridizes to the target template in the sample to form a primer:template pair, and (ii) an aptamer that binds to a ligand molecule of interest, if the ligand is present or if the ligand is present at a level or concentration greater than a threshold level. Binding of the ligand to the aptamer causes a conformational change in the ampliSwitch nucleic acid that allows the priming sequence to hybridize to the target template. The method may further involve incubating the mixture under conditions that allow the priming sequence to hybridize to the target template, extending the primer sequence to synthesize an extension product that is complementary to the target template, and detecting the extension product. The presence of one or more extension products is indicative of the detection of the ligand of interest. In certain embodiments, the amount of an extension product may correlate with and therefore be used to determine the amount of the ligand in the sample.

Extension of the primer sequence may be performed by any polymerase-mediated primer extension reaction known in the art. For instance, primer extension may be performed by PCR, SDA, RCA, ligase chain reaction, NASBA, transcription-mediated amplification or other amplification methods known in the art. Natural, non-natural or modified nucleotides may be incorporated into the extension products. Non-natural or modified nucleotides include, without limitation, radioactively, fluorescently, or chemically-labeled nucleotides. Furthermore, extension products may comprise one or more fluorophores and/or quencher moieties which alter the fluorescence of the sample. A quencher moiety causes there to be little or no signal from a fluorescent label (e.g., a fluorophore) when placed in proximity to the label. Such methods are useful, for example, in rapid or high-throughput methods. Detection of a labeled extension product may be performed by direct or indirect means (e.g., via a biotin/avidin or a biotin/streptavidin linkage). It is not intended that the present invention be limited to any particular detection system or label.

In certain embodiments, an extension product is detectable using one or more of a variety of detection methods, including, but not limited to, enzyme (e.g., ELISA, as well as enzyme-based histochemical assays), colorimetric, fluorescent, radioactive, chemical, electrical, optical, and luminescent methods. Other examples of detection methods include, without limitation, gel electrophoresis or microarrays including conventional gene or oligonucleotide chips, bead-based array systems (see, e.g., U.S. Pat. No. 6,355,431), and arrays using nucleic acids containing electron transfer moieties (see, e.g., U.S. Pat. No. 6,753,143).

Still other aspects of the invention provide a library of aptamer-regulated nucleic acids, such as libraries having a variegated population of nucleic acids having different aptamers and/or different priming sequence domains. A library of ampliSwitch nucleic acids may have diversity amongst the aptamers with respect to the types of ligands that can be bound (specificity) and/or variation amongst the aptamers with respect to the affinity for the same ligand. Likewise, a library of ampliSwitch nucleic acids may have diversity amongst the priming sequence domains with respect to the thermodynamic stability of the priming sequence domain in the presence or absence of ligand binding and/or may hybridize to unique target template nucleic acids.

In certain embodiments, the invention provides a library of two or more ampliSwitch nucleic acids, wherein each aptamer in the library binds to a different ligand. Each of the two or more ampliSwitch nucleic acids comprises (i) a priming sequence that hybridizes to a target template to form a primer:template pair, and (ii) an aptamer that binds to a ligand. Binding of the ligand to the aptamer causes a conformational change in the nucleic acid that alters the ability of the priming sequence to hybridize to its target template. In certain embodiments, each of the two or more ampliSwitch nucleic acids comprises the same priming sequence(s) that is(are) capable of hybridizing to the same target template(s). In certain embodiments, each of the two or more ampliSwitch nucleic acids comprising a unique priming sequence (which may comprise one or more priming sequence domains), and therefore, each ampliSwitch molecule's priming sequence hybridizes to one or more unique target templates.

In another embodiment, the invention provides a library of two or more ampliSwitch nucleic acids, wherein each aptamer in the library has a different binding affinity for the same ligand. Each of the two or more ampliSwitch nucleic acids comprises (i) a priming sequence that hybridizes to a target template to form a primer:template pair, and (ii) an aptamer that binds to a ligand. Binding of the ligand to the aptamer causes a conformational change in the nucleic acid that alters the ability of the priming sequence to hybridize to its target template. In certain embodiments, each of the two or more ampliSwitch nucleic acids comprises the same priming sequence(s) that is(are) capable of hybridizing to the same target template(s). In certain embodiments, each of the two or more ampliSwitch nucleic acids comprising a unique priming sequence (which may comprise one or more priming sequence domains), (and therefore, each ampliSwitch molecule's priming sequence hybridizes to one or more unique target templates.

In certain other embodiments, the invention provides a library of two or more ampliSwitch nucleic acids, wherein the priming sequence domain in each nucleic acid has a different thermodynamic stability. The different thermodynamic stabilities in the priming sequence domains cause each ampliSwitch nucleic acid to undergo a conformational change in response to different concentrations of ligand. Each of the two or more ampliSwitch nucleic acids comprises (i) a priming sequence that hybridizes to a unique target template to form a primer:template pair, and (ii) an aptamer that binds to a ligand. Binding of the ligand to the aptamer causes a conformational change in the nucleic acid that alters the ability of the priming sequence to hybridize to its target template.

In another aspect, the invention provides an expression library comprising one or more expression constructs. Each of the expression constructs includes a nucleic acid sequence that encodes an ampliSwitch molecule of the invention.

In a further aspect, the invention provides methods employing one or more of the libraries of ampliSwitch nucleic acids herein. To illustrate, the present invention contemplates a method for detecting the concentration of a ligand in a sample, such as for example, a medical sample, a food sample, a cosmetic sample, or an environmental sample. A medical sample may include, but are not limited to, blood, serum, urine, saliva, or biopsy sample from an animal including a human patient. A food sample may include, but are not limited to, a piece of food, or a swipe of a food processing object (e.g., blender, knife, processor, kitchen counter). An environmental sample may include, but are not limited to, a water sample from a natural body of water or another source of interest (e.g., tap water, water storage container), an air sample, or a geological sample. A sample may be processed and prepared to be analyzed using a method of the present invention.

In one embodiment, the method involves forming a mixture that comprises the sample, two or more unique target templates, and a library of two or more ampliSwitch nucleic acids as described herein. Each aptamer in the library has a different binding affinity for the same ligand. Each of the unique target templates is associated with a nucleic acid that binds to the ligand when the ligand is present in a specific concentration (or greater than the specific concentration). The method further involves incubating the mixture under conditions that allow a priming sequence to hybridize to its target template, extending the primer sequence to synthesize an extension product that is complementary to the target template, and detecting the extension product. The identity of the extension product can be associated with the concentration of the ligand.

In another embodiment, the present invention contemplates a method for detecting the concentration of a ligand in a sample using a library of two or more ampliSwitch nucleic acids, wherein the priming sequence domain in each nucleic acid has a different thermodynamic stability. The method involves forming a mixture that comprises the sample, two or more unique target templates, and said library. Each of the unique target templates is associated with a nucleic acid that comprises a priming sequence domain that undergoes a conformational change dependent on the concentration of the ligand that is present. The method further involves incubating the mixture under conditions that allow the priming sequence to hybridize to its target template, extending the primer sequence to synthesize an extension product that is complementary to the target template, and detecting the extension product. In certain embodiments, an extension product may be amplified by nucleic acid amplification prior to detection. Any method for nucleic acid amplification, such as PCR, may be used in the invention. The identity of the extension product can be associated with the concentration of the ligand.

The present invention also contemplates a method for detecting two or more different ligands in a sample. The method involves forming a mixture that comprises the sample, two or more unique target templates, and a library of two or more ampliSwitch nucleic acids as described herein. Each aptamer in the library binds to a different ligand. Each of the unique target templates is associated with a nucleic acid that binds to a unique ligand. The method further involves incubating the mixture under conditions that allow a priming sequence to hybridize to its target template, extending the primer sequence to synthesize an extension product that is complementary to the target template, and detecting the extension product. The identity of the extension product can be associated with the ligand of interest to determine if the ligand is present in the sample.

In certain embodiments, the present invention provides a package or kit for detecting a ligand of interest in a sample. A package or kit may comprise, for example, (i) at least one container means having disposed therein one or more ampliSwitch nucleic acid molecules as described herein; and (ii) a label and/or instructions for performing a method for detecting the ligand of interest. Any method described herein for detecting a ligand of interest may be used.

The embodiments and practices of the present invention, other embodiments, and their features and characteristics, will be apparent from the description, figures and claims that

BRIEF DESCRIPTION OF THE DRAWINGS

FIG. 1A is a schematic of an ampliSwitch nanosensor. The conformation of this sensor is illustrated in the nonligand-bound state. The locations of the priming stem, aptamer domain, and switching aptamer stem are indicated. FIG. 1B is a schematic of the mechanism by which an ampliSwitch sensor switches between two different conformations induced by ligand binding to the ampliSwitch. In the unbound state the ampliSwitch is not bound to the template or the ligand. In the bound state the ampliSwitch is bound to ligand which induces a conformational shift in the ampliSwitch structure such that the priming stem binds to the template and the switching aptamer stem binds to a complementary region within the ampliSwitch. Primer sequence is shown in red. Switching aptamer stem sequence is shown in blue. Target template sequence is shown in green.

FIG. 3A shows the conformational change that is induced in ampliSwitch molecules in response to ligand binding. FIG. 3B shows the hybridization of an ampliSwitch primer sequence to a target template in the presence of ligand. The primer:template pair trigger primer extension and a PCR amplification reaction to generate a plurality of amplified primer extension products that are detected by standard methods of detecting nucleic acid products, such as direct measurement of fluorescence by qRT-PCR, on an agarose gel, or by hybridization to an oligonucleotide microarray.

Figure 7:
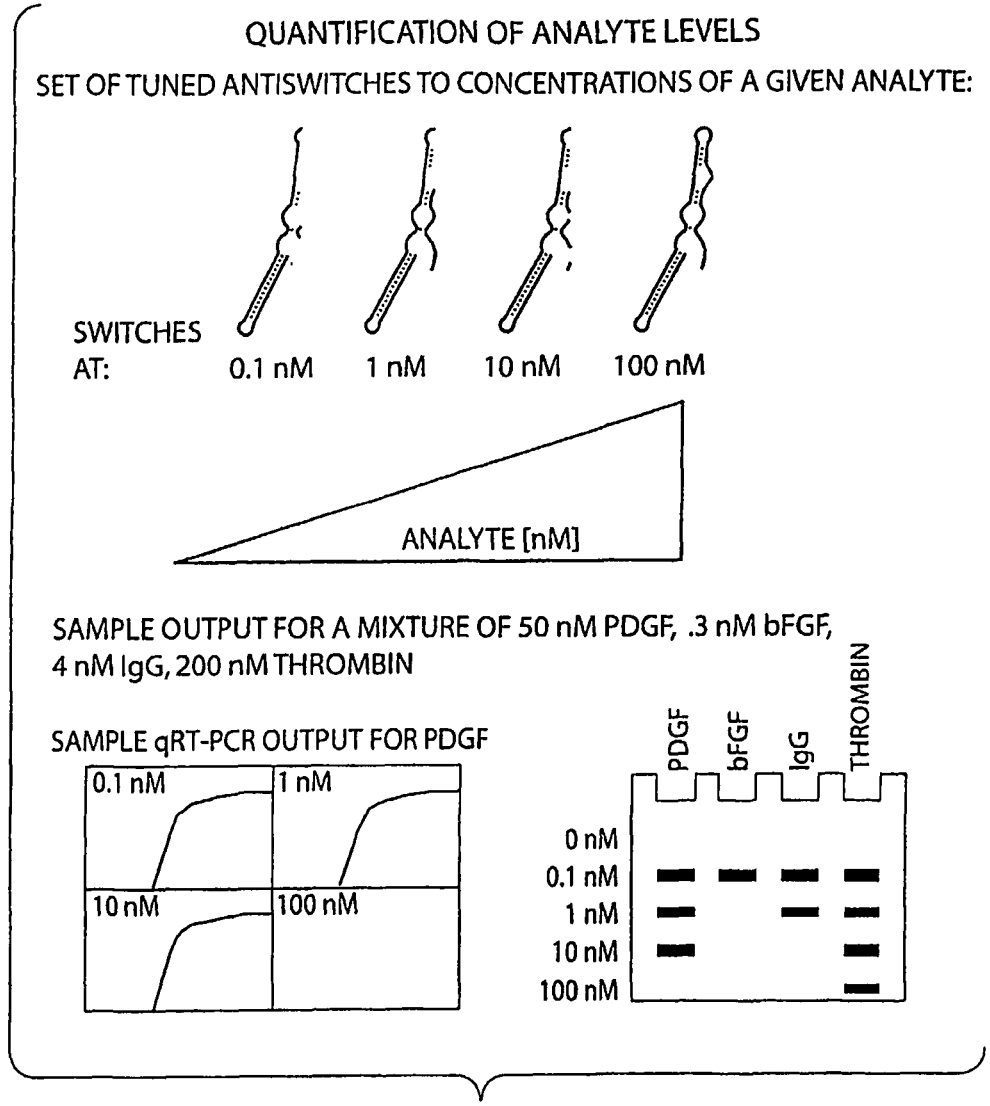

to FIG. 7 is a diagram that shows the use of sets of ampliSwitches to detect the concentration of multiple ligands in a sample. Each analyte will be quantified with a set of ampliSwitch sensors that each bind to a different ligand (e.g., PDGF, bFGF, IgG, and thrombin) and are tuned to switch at different concentration set points. The output from the triggered PCR reaction will be detected, for example, as different sized templates on a gel or different fluorescent channel amplification signals through qRT-PCR.

Figure 8A:
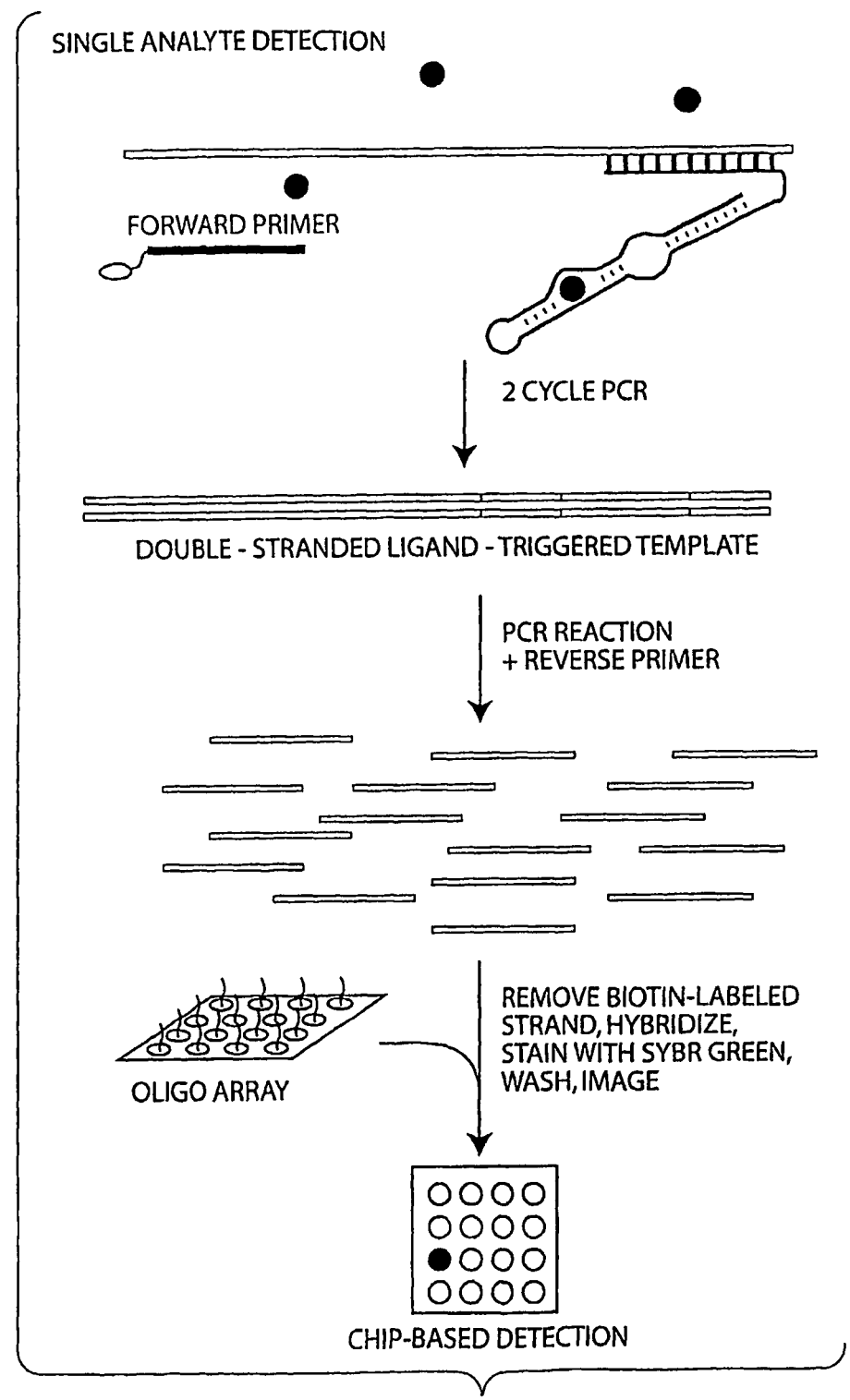
Figure 8B:
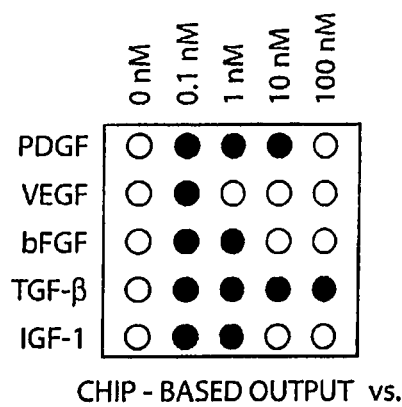
Figure 8C:
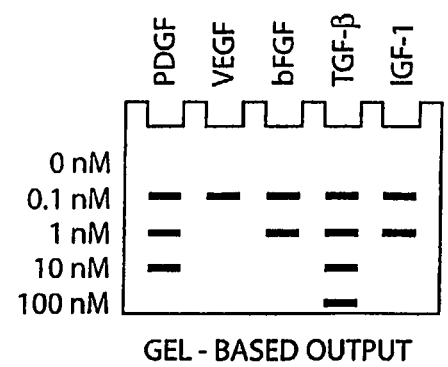

FIGS. 8A-8C show oligonucleotide microarray-based detection using ampliSwitch sensors and triggered PCR output. The template output from each ampliSwitch-triggered PCR detection event will hybridize to a unique location on an oligonucleotide microarray as illustrated for a single analyte in FIG. 8A. This format will allow multiplex detection of both analyte sets and concentration sets. The microarray-based output from a multiplex detection and quantification scheme is illustrated in FIG. 8B, next to the corresponding gel output in FIG. 8C.

Figure 9:
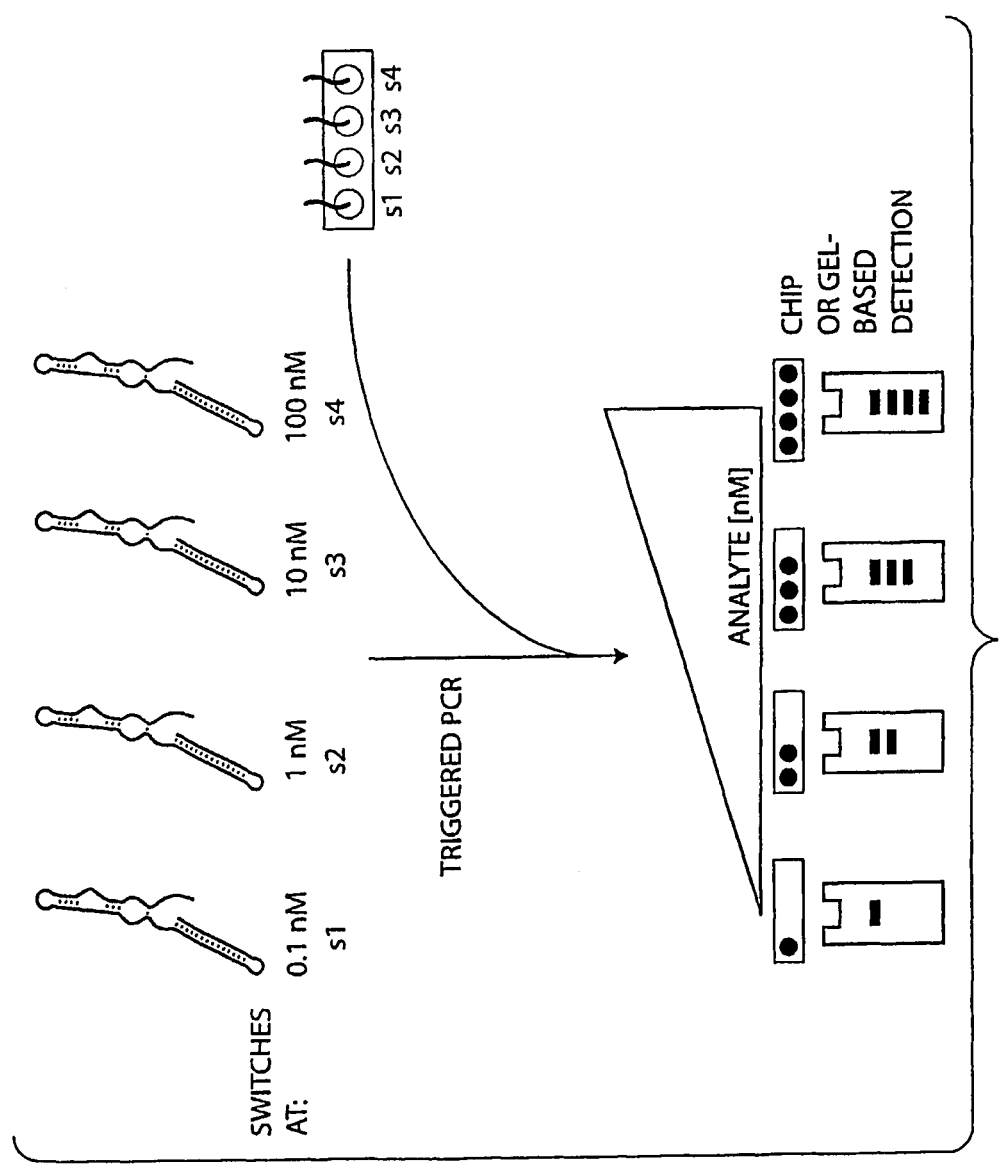

FIG. 9 is a diagram that illustrates the quantification of ligand analyte levels using a library of ampliSwitch molecules. A set of ampliSwitches are 'tuned' so that they undergo a conformational change in response to specific analyte concentrations. AmpliSwitches are tuned by modifying the dissociation constant of the aptamer and ligand or the thermodynamic stability of the primer sequence stem or the aptamer stem. The set of ampliSwitches is used simultaneously to detect the concentration of a ligand in a sample. Illustrated are two methods of detecting the amplified product, spotted oligonucleotides (e.g., on a microarray or nitrocellulose filter) and agarose-gel detection.

FIG. 10 is a diagram that illustrates the use of ampliSwitch technology for quantification of analyte ligand levels. Analyte concentrations can be detected by designed sets of 'tuned' ampliSwitches to each analyte using forward engineering techniques. These ampliSwitches can then be used simultaneously (e.g., in a library of two or more ampliSwitches) with their primer:template pairs to detect concentrations of different analytes in a complex mixture as illustrated. Examples of output detection using two different methods, microarray-based and agarose gel-based, are illustrated.

Figure 11A:
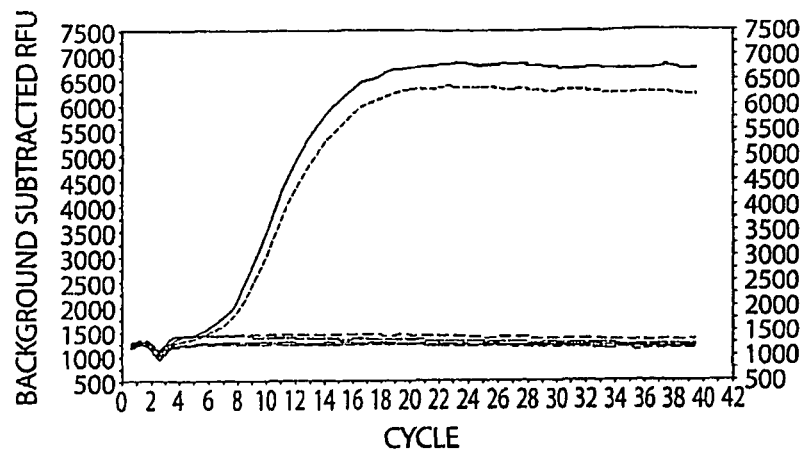
Figure 11B:
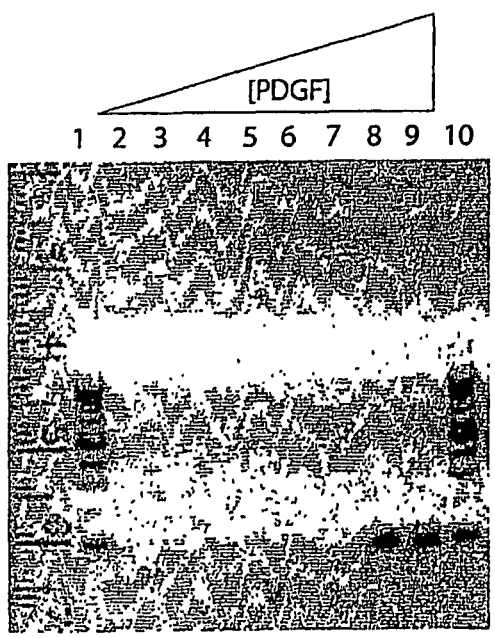

FIGS. 11A and 11B show ampliSwitches as nanosensors for digital, amplification-based analyte quantification. FIG. 11A is a graph showing qRT-PCR data from a PDGF ampliSwitch (sPDGF1). Positive signals are detected in triggered PCR reactions run at 400 and 200 nM PDGF. No amplification signals are detected at concentrations of 100 nM and lower. FIG. 11B is a photograph of agarose gel output from triggered PCR reactions. Lanes 1 and 10, 100-bp ladder; lanes 2-9, varying concentrations of PDGF; lane 2-0 nM; lane 3-1.25 nM; lane 4-12.5 nM; lane 5-25 nM; lane 6-50 nM; lane 7-100 nM; lane 8-200 nM; lane 9-400 nM. Positive amplification signals are detected in lanes 8 and 9, corresponding to 200 and 400 nM PDGF, respectively.

Figure 12A:
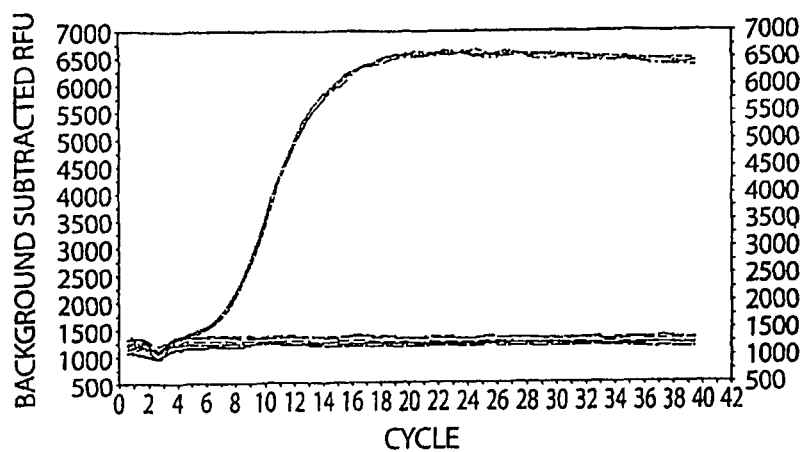
Figure 12B:
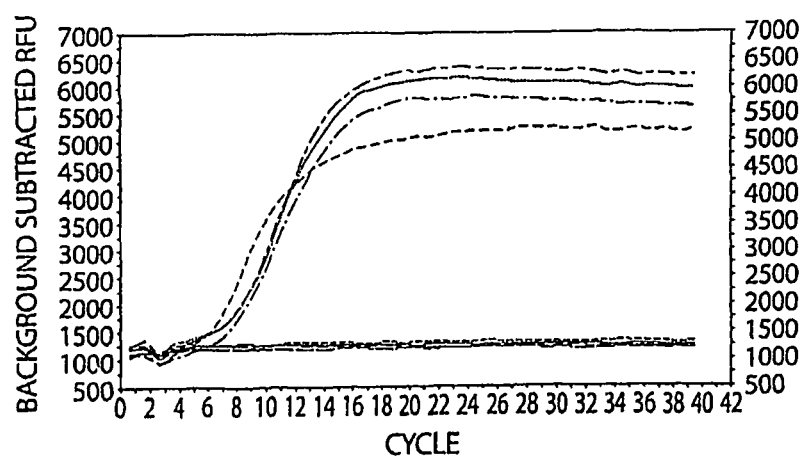
Figure 12C:
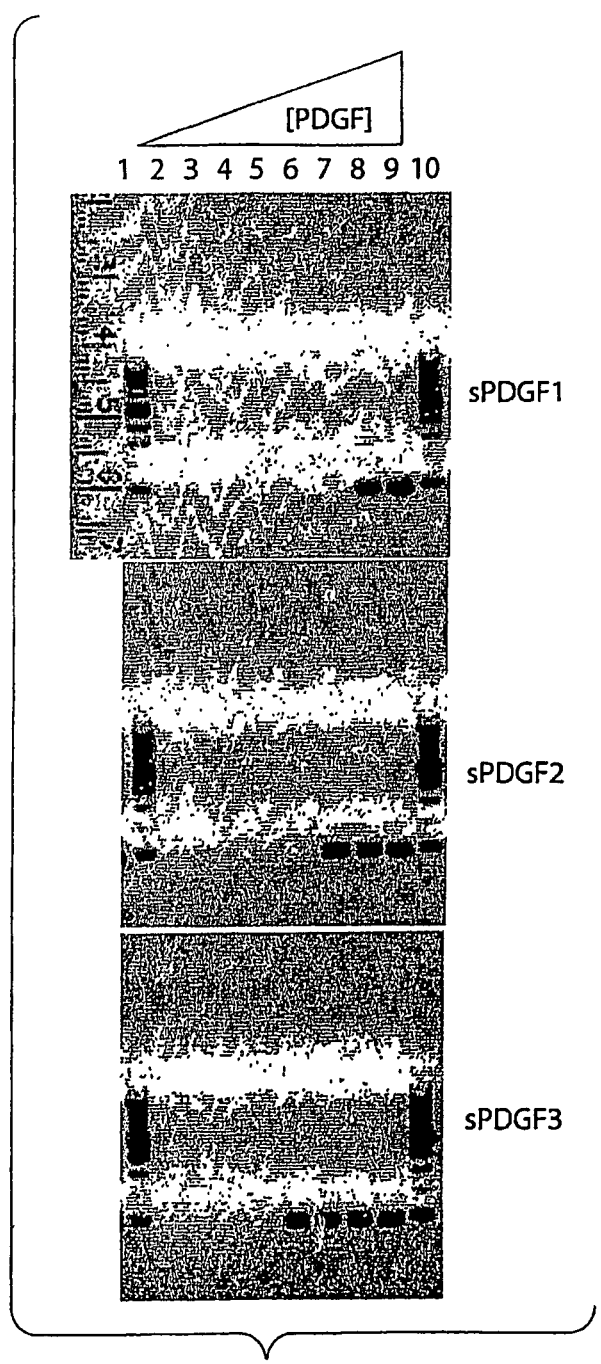

FIGS. 12A-12C show a tuned ampliSwitch concentration response. FIG. 12A is a graph showing qRT-PCR output from sPDGF2. Positive signals are detected at PDGF concentrations between 100-400 nM PDGF. FIG. 12B is a graph showing qRT-PCR output from sPDGF3. Positive signals are detected at PDGF concentrations between 50-400 nM PDGF. FIG. 12C is a series of photographs of agarose gel outputs from tuned ampliSwitch sensors. Lanes 1 and 10, 100-bp ladder; lanes 2-9, varying concentrations of PDGF; lane 2-0 nM; lane 3-1.25 nM; lane 4-12.5 nM; lane 5-25 nM; lane 6-50 nM; lane 7-100 nM; lane 8-200 nM; lane 9-400 nM. Data indicates that sPDGF1 switches conformation at ligand concentrations between 100 and 200 nM, sPDGF2 between 50 and 100 nM, and sPDGF3 between 25 and 50 nM.

Figure 13:
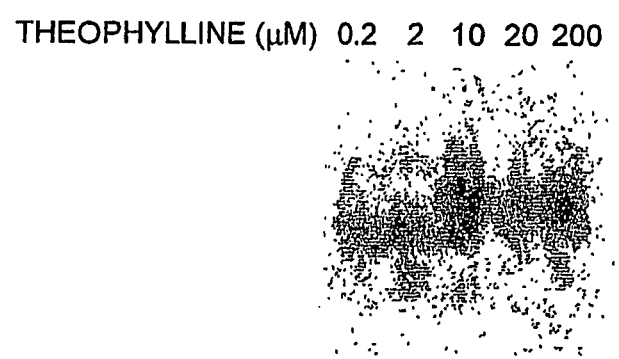

FIG. 13 is a photograph showing a gel shift assay that monitors the formation of an ampliSwitch-template-small molecule ligand complex across different concentrations of theophylline.

Figure 14:
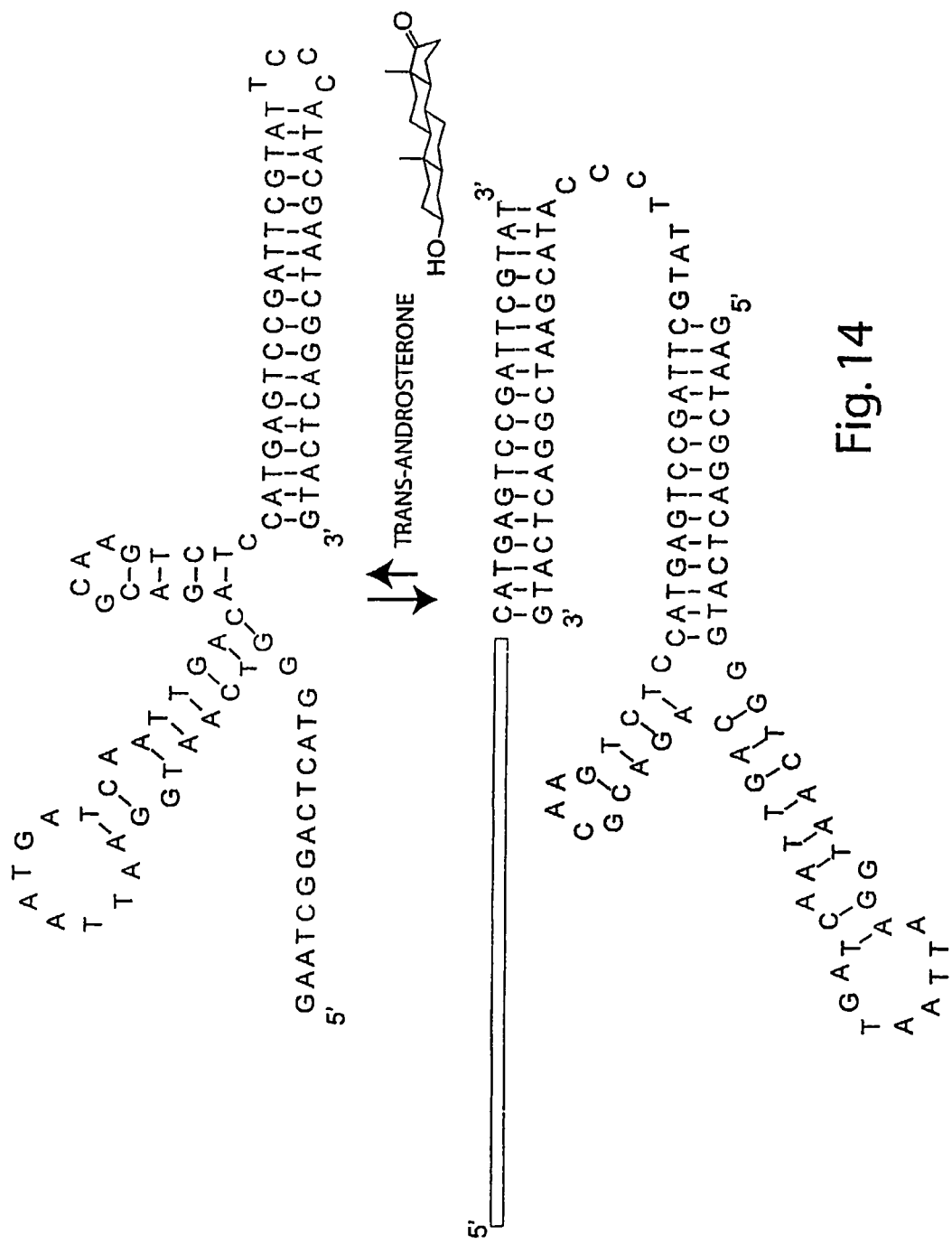

FIG. 14 shows the sequence and predicted structure of an ampliSwitch that binds to the hormone trans-androsterone. Structural switching of the ampliSwitch in the presence or absence of trans-androsterone is shown. In the "on" state, the trans-androsterone responsive switch hybridizes to a target template. Primer sequence is shown in blue. Switching aptamer stem sequence is shown in red. Target template sequence is shown in green. The sequence of the trans-androsterone-binding ampliSwitch is represented by SEQ ID NO: 1. The sequence portion that complements the 3'-portion of the ampliSwitch is represented by SEQ ID NO: 2.

Figure 15:
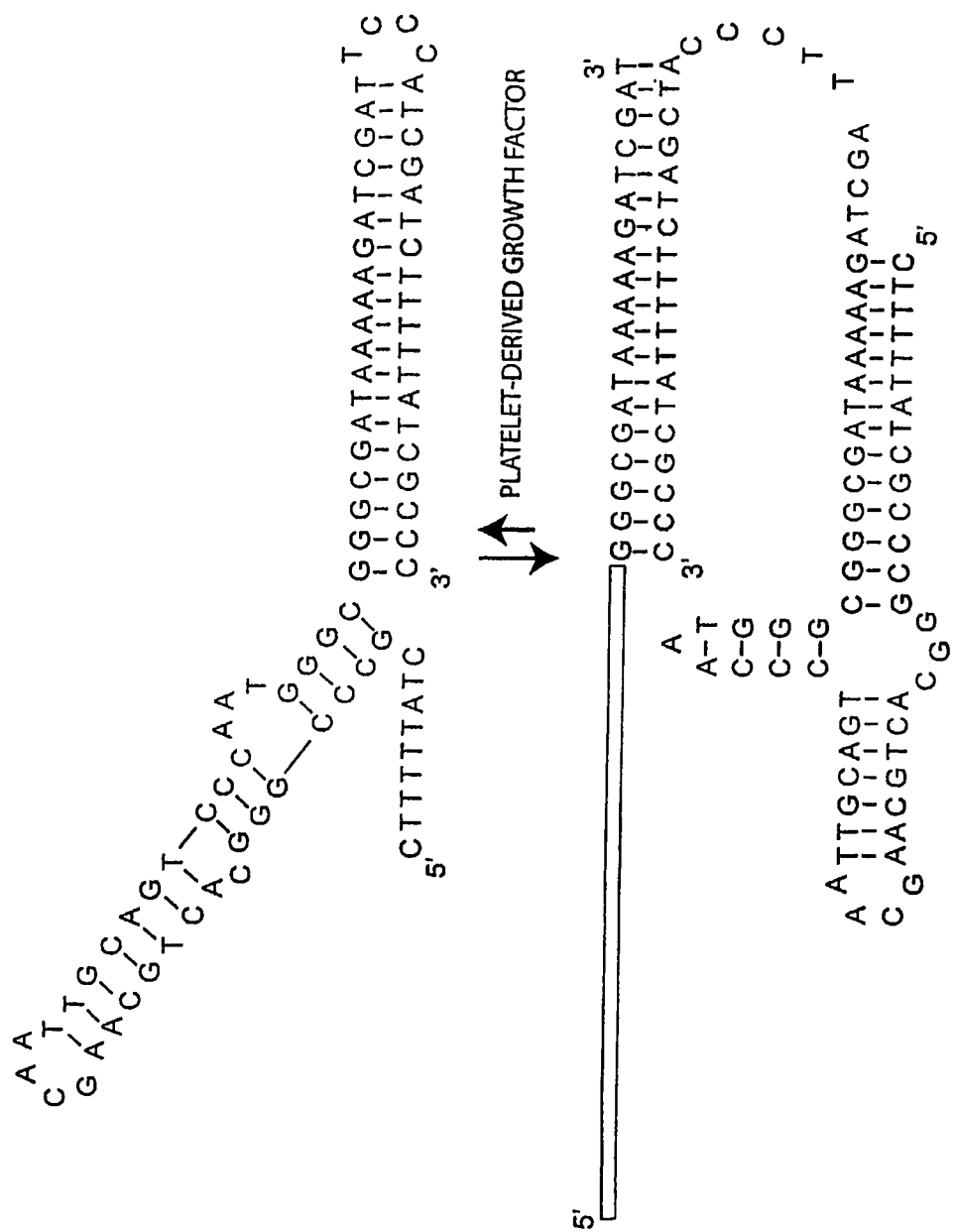

FIG. 15 shows the sequence and predicted structure of an ampliSwitch that binds to the platelet-derived growth factor (PDGF) protein. Structural switching of the ampliSwitch in the presence or absence of PDGF is shown. In the "on" state, the PDGF-responsive switch hybridizes to a target template. Primer sequence is shown in blue. Switching aptamer stem sequence is shown in red. Target template sequence is shown in green. The sequence of the PDGF-binding ampliSwitch is represented by SEQ ID NO: 3. The sequence portion that complements the 3'-portion of the ampliSwitch is represented by SEQ ID NO: 4.

FIGS. 16A and 16B show a tuned ampliSwitch concentration response. FIG. 16A is a photograph of an agarose gel output from an ampliSwitch sensor that is tuned to respond to PDGF at concentrations from 100-200 nM (or greater) PDGF. The gel indicates that primer extension products were generated when PDGF was present at 200 nM and 400 nM. FIG. 16B is a photograph of an agarose gel output from an ampliSwitch sensor that is tuned to respond to trans-androsterone at concentrations from 4-40 µM (or greater) trans-androsterone. The gel indicates that primer extension products were generated when trans-androsterone was present at 40 µM and 400 µM.

Figure 17A:
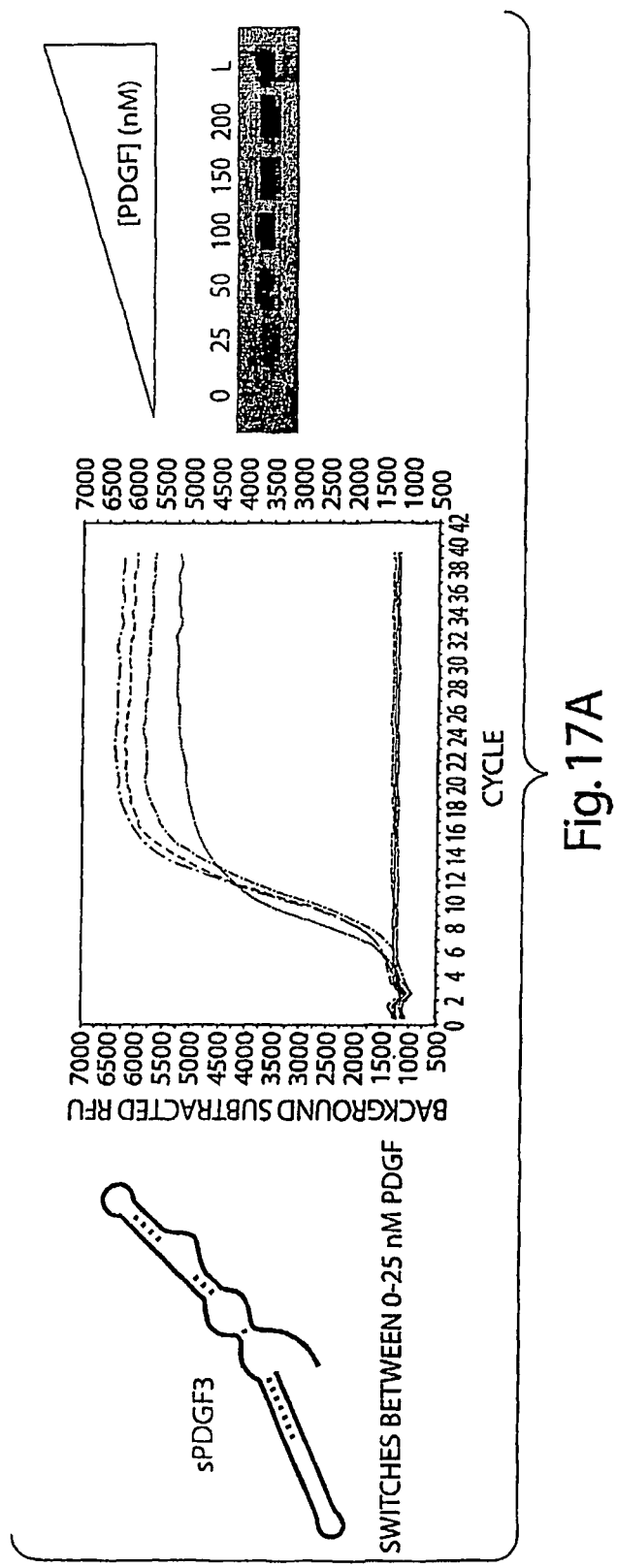
Figure 17B:
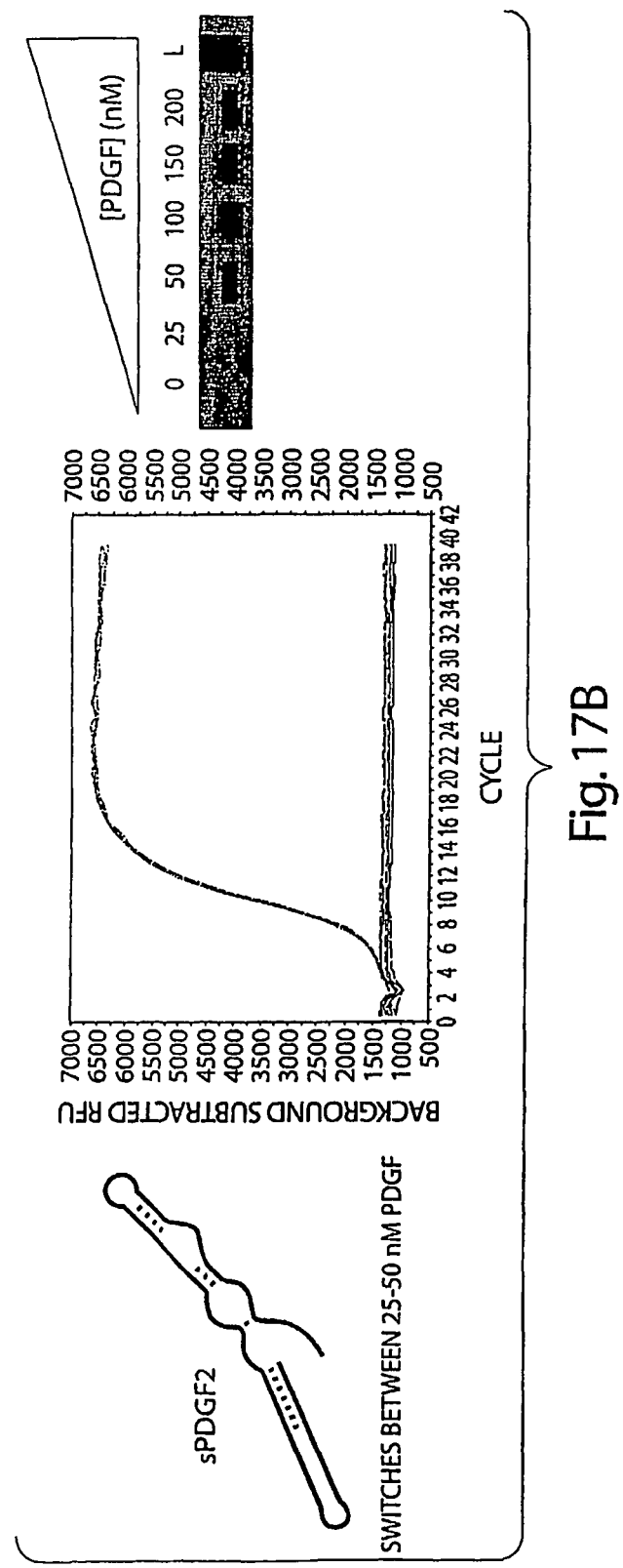
Figure 17C:
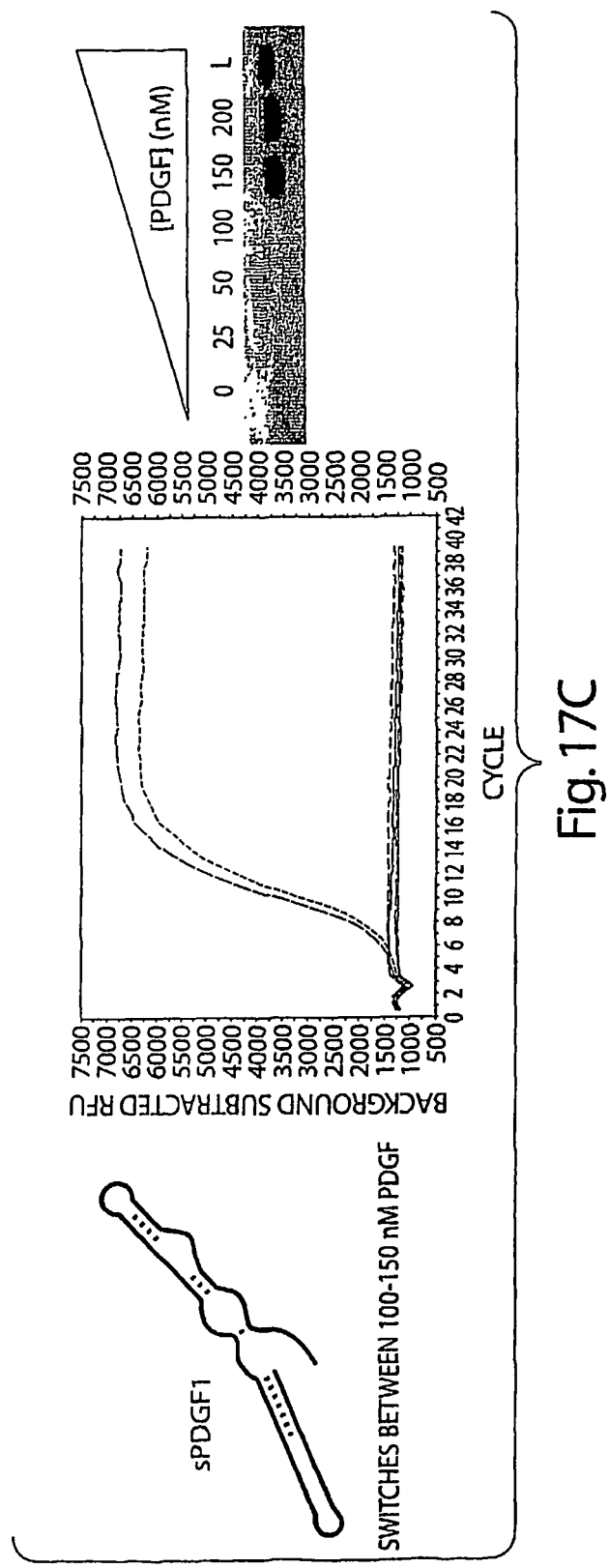

FIGS. 17A-17C show a tuned ampliSwitch concentration response for PDGF-responsive switches sPDGF1, sPDGF2, and sPDGF3. sPDGF1 switches conformation between 0 and 25 nM PDGF; sPDGF2 switches conformation between 25 and 50 nM PDGF; and sPDGF3 switches conformation between 100 and 150 nM PDGF. FIG. 17A is a qRT-PCR graph and agarose-gel showing output from the tuned ampliSwitches. The agarose-gel output indicates that extension products are detectable at PDGF concentrations of 25 nM and higher with the sPDGF3 switch. FIG. 17B is a qRT-PCR graph and agarose-gel showing output from tuned ampliSwitches. The agarose-gel output indicates that extension products are detectable at PDGF concentrations of 50 nM and higher with the sPDGF2 switch. FIG. 17C is a qRT-PCR graph and agarose-gel showing output from tuned ampliSwitches. The agarose-gel output indicates that extension products are detectable at PDGF concentrations of 150 nM and higher with the sPDGF1 switch.

DETAILED DESCRIPTION OF THE INVENTION

1. Overview

The present invention provides aptamer-regulated nucleic acids, or "ampliSwitches," that respond to binding to a ligand or analyte of interest. One aspect relates to aptamer-regulated nucleic acids and methods that employ ampliSwitches as in vitro sensors to detect the presence, absence, or amount of a molecule in a sample. Another aspect of the invention provides a library of two or more aptamer-regulated nucleic acids, and methods and kits employing such a library for the simultaneous detection of multiple molecules in a sample, or for detecting the concentration of a molecule in a sample.

Thus, one aspect of the present invention provides engineered, aptamer-regulated nucleic acids that are allosteric sensors of analyte ligands. A general design of an aptamer-regulated nucleic acid is based on conformational dynamics of nucleic acid folding to create a dual stem molecule comprised of a primer sequence domain stem and an aptamer stem. These components are preferably designed such that in the absence of ligand, the free energy of the priming sequence stem is lower than that of the aptamer stem. Ligand and target act cooperatively to alter the conformational dynamics of these molecules and stabilize the formation of the aptamer stem and the binding of the priming sequence domain to its target transcript. The aptamer-regulated nucleic acid platform is flexible, enabling both positive and negative regulation. The "on" switch is designed using the same energetics on an altered platform such that in the absence or low levels of ligand the priming sequence domain is free to bind to the target; however ligand binding changes the conformational dynamics of these molecules so that the priming sequence domain is bound in the aptamer stem.

Many detection strategies, such as ELISA, immuno-PCR, and proximity ligation, benefit from amplifying output signals. Accordingly, in certain embodiments of the invention, ampliSwitch sensing events are amplified using triggered PCR. In this method, the ampliSwitch, primer:template pair, and analyte are incubated initially in a buffered solution. In mixtures with levels of analyte sufficient to bind to the ampliSwitch, the ampliSwitch will undergo a conformational change such that the priming strand will bind to its template. Thermostable DNA polymerase and dNTPs are then added to the mixture and cycled through appropriate PCR conditions. In the absence of ampliSwitch binding to the template, no amplifiable template is created. This amplified output can be detected by standard methods for nucleic acid detection. For example, this amplified output can be detected through quantitative real-time PCR, agarose gel detection, or by hybridization to oligonucleotide microarrays or nitrocellulose filters. Due to the unique switching behavior of ampliSwitch nucleic acids, the presence or absence of an analyte ligand is given in a binary 'yes/no' format. Specifically, a given ampliSwitch will prime the same number of templates at all analyte ligand concentrations above a given threshold, and will not prime the template below the same threshold.

The present invention also contemplates other methods for amplifying output signals resulting from hybridization of a primer sequence to a target template. For example, output signals, or extension products, may be generated by polymerase chain reaction, strand displacement amplification, rolling circle amplification, nucleic acid sequence based amplification, ligase chain reaction, transcription-mediated amplification, Q-beta replicase, Invader™ technology, or other amplification methods known in the art. Accordingly, in addition to a target template, a solution comprising an ampliSwitch of the invention may further comprise any necessary enzymes, polymerases, nucleases, ligases, nucleic acids, or other components required for any of the methods described herein. For instance, depending on the method of primer extension that is utilized, a sample may further comprise an additional nucleic acid primer. The design and use of such additional components are well known to the skilled artisan.

The switching dynamics of aptamer-regulated nucleic acids are amenable to tuning by forward engineering design strategies based on thermodynamic properties of nucleic acids. Altering the free energy of the primer domain alters the conformational dynamics of these molecules in a predictable fashion. Specifically, decreasing the stability of the primer sequence domain stem decreases the ligand concentration necessary to induce a conformational change in an aptamer-regulated nucleic acid and increasing the stability of the primer sequence domain stem increases the ligand concentration necessary to induce the conformational change.

In addition, the aptamer-regulated nucleic acid platform is fully modular, enabling ligand response and target template specificity to be engineered by swapping domains within the aptamer-regulated nucleic acid. This provides a platform for the construction of tailor-made aptamer-regulated nucleic acids for a variety of different ligands. Ligand binding of the aptamer domain in aptamer-regulated nucleic acids is designed separately from the target template specificity of the primer sequence domain by swapping only the aptamer domain. Likewise, the target template specificity of the primer sequence domain can be designed separately from the ligand binding of the aptamer domain by swapping the primer sequence domain so that a different target template nucleic acid is targeted without affecting the aptamer domain. Aptamer-regulated nucleic acids present a powerful, flexible method of detecting one or more molecules in a sample.

In certain embodiments, aptamer-regulated nucleic acids comprise multiple modular components, e.g., one or more aptamer domains and/or one or more primer sequence domains. In other embodiments, an aptamer-regulated nucleic acid of the invention interacts with and responds to multiple ligands. For instance, aptamer-regulated nucleic acids may comprise an aptamer domain that responds to multiple ligands, or may comprise more than one aptamer domain that each respond to a ligand. Optionally, one or more primer sequence domains are modulated by the one or more aptamer domains that respond to multiple ligands. In a specific aspect, a cooperative ligand controlled nucleic acid is provided, wherein multiple ligands sequentially bind to multiple aptamer domains to allosterically regulate one or more primer sequence domains. Aptamer-regulated nucleic acids comprising multiple modular components are useful for processing multiple ligands and the generation of cooperative aptamer-regulated nucleic acids. For instance, an aptamer-regulated nucleic acid may bind to two or more different ligands. An aptamer-regulated nucleic acid may be configured so that it only hybridizes to a target template in response to the binding of both ligands, or to neither of the two ligands. In aptamer-regulated nucleic acids that bind to two or more ligands, the binding of a first ligand may increase the capacity for the aptamer to bind the second ligand. In certain other embodiments, two or more aptamer-regulated nucleic acid ampliSwitches respond to two or more ligands, but have a single output. For instance, a target template can be hybridized by the primer sequences of ampliSwitches that respond to different ligands.

By "primer" or "priming sequence" herein is meant a nucleic acid that will hybridize to some portion, i.e. a domain, of a target sequence or template. Priming sequences of the present invention are designed to be complementary to a target sequence, such that hybridization of the target sequence and the probes of the present invention occurs through base-pairing. This complementarity need not be perfect; there may be any number of base pair mismatches which will interfere with hybridization between the target sequence and the primers of the present invention. However, if the number of mutations is so great that no hybridization can occur under even the least stringent of hybridization conditions, the sequence is not a complementary target sequence or template.

By "ligand" or "analyte" or grammatical equivalents herein is meant any molecule or compound to be detected and that can interact with an aptamer to be designed and/or selected as described here. Suitable ligands or analytes include, but are not limited to, small chemical molecules such as environmental or clinical chemicals, pollutants or biomolecules, including, but not limited to, pesticides, insecticides, toxins, therapeutic and abused drugs, hormones, antibiotics, antibodies, organic materials, etc. Suitable biomolecules include, but are not limited to, proteins (including enzymes, immunoglobulins and glycoproteins), nucleic acids, lipids, lectins, carbohydrates, hormones, whole cells (including procaryotic (such as pathogenic bacteria) and eukaryotic cells, including mammalian tumor cells), viruses, spores, etc. Illustrative analytes that are proteins include, but are not limited to, enzymes; drugs; cells; antibodies; antigens; cellular membrane antigens and receptors (neural, hormonal, nutrient, and cell surface receptors) or their natural ligands.

Accordingly, the present invention provides compositions and methods for detecting the presence or absence of a ligand or analyte of interest in a sample. As will be appreciated by those in the art, the sample may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples; purified samples, such as purified genomic DNA, RNA, proteins, etc.; raw samples (bacteria, virus, genomic DNA, etc.). As will be appreciated by those in the art, virtually' any experimental manipulation may have been done on the sample, including, but not limited to lysing or rupturing cells in the sample or purifying the sample to remove one or more components.

2. Aptamer-regulated Nucleic Acids

In one embodiment, an aptamer-regulated nucleic acid of the invention comprises an aptamer domain and a primer or priming sequence domain. An aptamer-regulated nucleic acid of the invention may comprise DNA or RNA or chimeric mixtures, derivatives or modified versions thereof, and may be single-stranded or double-stranded. An aptamer-regulated nucleic acid may comprise multiple modular components, e.g., one or more aptamer domains and/or one or more primer domains. Aptamer-regulated nucleic acids may further comprise a functional group or a functional agent, e.g., an intercalator or an alkylating agent. Aptamer-regulated nucleic acids may comprise synthetic or non-natural nucleotides and analogs (e.g., 6-mercaptopurine, 5-fluorouracil, 5-iodo-2'-deoxyuridine and 6-thioguanine) or may include modified nucleic acids. Exemplary modifications include cytosine exocyclic amines, substitution of 5-bromo-uracil, backbone modifications, methylations, and unusual base-pairing combinations. Aptamer-regulated nucleic acids may include labels, such as fluorescent, radioactive, chemical, or enzymatic labels.

AmpliSwitches can be modified at the base moiety, sugar moiety, or phosphate backbone, for example, to improve stability of the molecule, hybridization, etc. AmpliSwitches may include other appended groups such as peptides. To this end, an ampliSwitch may be conjugated to another molecule, e.g., a peptide.

Aptamer-regulated nucleic acids may be modified so that they are resistant to nucleases, e.g. exonucleases and/or endonucleases, and are therefore stable in solution. Exemplary nucleic acid molecules for use in aptamer-regulated nucleic acids are phosphoramidate, phosphothioate and methylphosphonate analogs of DNA (see also U.S. Pat. Nos. 5,176,996; 5,264,564; and 5,256,775).

An ampliSwitch may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4thiouracil, 5-methyluracil, uracil-5-oxyacetic acid methyl ester, uracil-5-oxyacetic acid (v), 5-methyl-2-thiouracil, 3-(3-amino-3-N2-carboxypropyl) uracil, (acp3)w, and 2,6-diaminopurine.

An ampliSwitch may also comprise at least one modified sugar moiety selected from the group including but not limited to arabinose, 2-fluoroarabinose, xylulose, and hexose.

An ampliSwitch can also contain a neutral peptide-like backbone. Such molecules are termed peptide nucleic acid (PNA)-oligomers and are described, e.g., in Perry-O'Keefe et al. (1996) *Proc. Natl. Acad. Sci. USA* 93:14670 and in Eglom et al. (1993) *Nature* 365:566. One advantage of PNA oligomers is their capability to bind to complementary DNA essentially independently from the ionic strength of the medium due to the neutral backbone of the DNA. In yet another embodiment, an ampliSwitch comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Aptamer-regulated nucleic acids of the invention also encompass salts, esters, salts of such esters, or any other salts. In certain embodiments, the salts or esters may be suitable for in vivo use, such as pharmaceutically acceptable salts or esters. In certain embodiments, any salts or esters suitable for in vitro use can be employed. Suitable base addition salts are formed with metals or amines, such as alkali and alkaline earth metals or organic amines. Examples of metals used as cations are sodium potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, an addition salt suitable for in vitro use includes a salt of an acid form of one of the components of the compositions of the invention. These include organic or inorganic acid salts of the amines. Preferred acid salts are the hydrochlorides, acetates, salicylates, nitrates and phosphates. Other salts that are suitable for in vitro use are well known to those skilled in the art and include basic salts of a variety of inorganic and organic acids. Preferred examples of acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pahnitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

In a further embodiment, an ampliSwitch is an -anomeric oligonucleotide. An -anomeric oligonucleotide forms specific double-stranded hybrids with complementary RNA in which, contrary to the usual-units, the strands run parallel to each other (Gautier et al., 1987, *Nucl. Acids Res.* 15:6625-6641). The oligonucleotide is a 2'-O-methylribonucleotide (Inoue et al., 1987, *Nucl. Acids Res.* 15:6131-6148), or a chimeric RNA-DNA analogue (Inoue et al., 1987, *FEBS Lett.* 215:327-330).

An aptamer domain responds to ligand or analyte binding to induce an allosteric change in the priming sequence domain, and alters the ability of the priming sequence domain to interact with its target template. Ligand binding, therefore, switches the primer domain from "off" to "on," or vice versa. Aptamer-regulated nucleic acids, therefore, act as a switch whose activity is turned "off" and "on" in response to ligand binding. The response of the aptamer domain to the ligand may also depend on the ligand identity and/or the amount or concentration of ligand exposed to the aptamer domain. For example, an aptamer may bind small molecules, such as drugs, metabolites, intermediates, cofactors, transition state analogs, ions, metals, nucleic acids, and toxins. Alternatively, an aptamer may bind natural and synthetic polymers, including proteins, peptides, nucleic acids, polysaccharides, glycoproteins, hormones, receptors and cell surfaces such as cell walls and cell membranes. In certain other embodiments, the aptamer domain of a ligand controlled nucleic acid is responsive to environmental changes. Environmental changes include, but are not limited to changes in pH, temperature, osmolarity, or salt concentration.

In preferred embodiments, ligand binding at the aptamer domain mediates a change in the conformational dynamics of these molecules that allows the primer sequence to hybridize to a target nucleic acid template. In certain embodiments, the primer sequence domain of an aptamer-regulated nucleic acid interacts with a target template nucleic acid by nucleic acid hybridization. For instance, an aptamer-regulated nucleic acid may comprise a primer sequence domain that comprises a hybridization sequence that hybridizes to a target template and an aptamer domain that binds to a ligand. The binding of the ligand to the aptamer domain causes a conformational change in the aptamer-regulated nucleic acid that alters the ability (such as availability and/or Tm) of the hybridization sequence of the primer domain to hybridize to a target template.

An aptamer-regulated nucleic acid ampliSwitch of the invention, may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. *Nucl. Acids. Res.* 16:3209 (1988)), methylphosphonate oligonucleotides can be prepared by use of controlled pore glass polymer supports (Sarin et al., *Proc. Natl. Acad. Sci. USA* 85:7448-7451 (1988)), etc.

Another approach for generating ampliSwitch nucleic acids utilizes standard recombinant DNA techniques using a construct in which the ampliSwitch or other aptamer-regulated nucleic acid is placed under the control of a strong pol III or pol II promoter in an expression vector. This construct can be transformed or transfected into a prokaryotic or eukaryotic cell that transcribes the ampliSwitch. Such a vector can remain episomal or become chromosomally integrated, as long as it can be transcribed to produce the desired ampliSwitch. Expression vectors appropriate for producing an aptamer-regulated nucleic acid are well-known in the art. For example, the expression vector is selected from an episomal expression vector, an integrative expression vector, and a viral expression vector. A promoter may be operably linked to the sequence encoding the ampliSwitch. Expression of the sequence encoding the ampliSwitch can be by any promoter known in the art to act in eukaryotic or prokaryotic cells. Such promoters can be inducible or constitutive. Examples of mammalian promoters include, but are not limited to, the SV40 early promoter region (Bernoist and Chambon, *Nature* 290:304-310 (1981)), the promoter contained in the 3' long terminal repeat of Rous sarcoma virus (Yamamoto et al., *Cell* 22:787-797 (1980)), the herpes thymidine kinase promoter (Wagner et al., *Proc. Natl. Acad. Sci. USA* 78:1441-1445 (1981)), the regulatory sequences of the metallothionine gene (Brinster et al, *Nature* 296:3942 (1982)), etc.

In certain embodiments, an aptamer-regulated nucleic acid is in the form of a hairpin or stem-loop structure. Such structures can be synthesized exogenously or can be formed by transcribing from RNA polymerase III promoters in cells suitable for expressing recombinant DNAs. Examples of making and using hairpin structures are described, for example, in Paddison et al., Genes Dev, 2002, 16:948-58; McCaffrey et al., Nature, 2002, 418:38-9; McManus et al., RNA 2002, 8:842-50; Yu et al., Proc Natl Acad Sci USA, 2002, 99:6047-52).

AmpliSwitch nucleic acids can be purified using a number of techniques known to those of skill in the art. For example, gel electrophoresis can be used to purify such molecules. Alternatively, non-denaturing methods, such as non-denaturing column chromatography, can be used to purify the ampliSwitch molecules. In addition, chromatography (e.g., size exclusion chromatography), glycerol gradient centrifugation, and affinity purification with antibodies can be used to purify ampliSwitches.

The invention thus provides a class of in vitro nucleic acid sensors, for example, aptamer-regulated nucleic acids that sense the presence or amount a molecule in a sample through changes in nucleic acid conformation upon ligand binding to the aptamer domain of an aptamer-regulated nucleic acid. For example, a ligand that interacts with the aptamer domain of an aptamer-regulated nucleic acid switches "on" the primer domain of the aptamer-regulated nucleic acid. The activated primer domain then hybridizes to a target template to form a primer:template pair. The primer:template pair may then act as a substrate for an extrinsic enzymatic activity. For example, the primer:template pair may act as a substrate for a DNA polymerase (e.g., taq polymerase or phi29 polymerase) which extends the primer sequence to form a complementary nucleic acid extension product. The presence and amount of the extension product, therefore, correlates with the amount or concentration of the ligand of interest. Any method known in the art can be used to detect the extension product. For example, an extension product can be detected by colorimetric detection, fluorescent detection, chemiluminescence, gel electrophoresis, or oligonucleotide microarray. In certain embodiments, the extension product is comprised of one or more non-natural or modified nucleotides. Non-natural or modified nucleotides include, without limitation, radioactively, fluorescently, or chemically labeled nucleotides. In other embodiments, the extension product is labeled with one or more fluorophores and/or quenchers which alter the fluorescence of said sample.

Aptamers

An "aptamer" may be a nucleic acid molecule, such as RNA or DNA that is capable of binding to a specific molecule with high affinity and specificity (Ellington et al., *Nature* 346, 818-22 (1990); and Tuerk et al., *Science* 249, 505-10 (1990)). Illustrative ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes. The binding of a ligand to an aptamer, which may be DNA or RNA, causes a conformational change in the primer domain and alters its ability to interact with its target template. Therefore, ligand binding affects the primer domain's ability to hybridize to a target template to form a primer:template pair, for example. An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants (Kd) of the aptamer for its ligand as compared to the dissociation constant of the aptamer for other materials in the environment or unrelated molecules in general. A ligand is one which binds to the aptamer with greater affinity than to unrelated material. Typically, the Kd for the aptamer with respect to its ligand will be at least about 10-fold less than the Kd for the aptamer with unrelated material or accompanying material in the environment. Even more preferably, the Kd will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

Aptamers are readily made that bind to a wide variety of molecules. Each of these molecules can be detected using the methods of the invention. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands in vitro aptamer selections (Werstuck and Green, *Science* 282:296-298 (1998)). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok, *Science* 9:324-9 (1999).

The aptamer-regulated nucleic acid of the invention can detect any ligand, insofar as the aptamer can bind to the ligand at a level that is greater than aptamer binding to unrelated material. The binding affinity of the aptamer for the ligand should also be sufficiently strong and the structure formed by the aptamer when bound to its ligand should be significant enough so as to switch an aptamer-regulated nucleic acid of the invention between "on" and "off" states. In some embodiments, the ligand is a polypeptide whose presence in a sample is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand may be a metal ion. In a specific embodiment, the aptamer domain of an aptamer-regulated nucleic acid responds to binding to caffeine. In certain embodiments, the ligand of the aptamer is a cell-permeable, small organic molecule. The ligand may optionally be a drug, including, for example, a steroid. The ligand may also be a metabolite or an intermediate of a drug.

The aptamer-regulated nucleic acid of the invention can be comprised entirely of RNA. In other embodiments of the invention, however, the aptamer-regulated nucleic acid can instead be comprised entirely of DNA, or partially of DNA, or partially of other nucleotide analogs.

Aptamers are typically developed to bind particular ligands by employing known in vivo or in vitro (most typically, in vitro) selection techniques known as SELEX (Ellington et al., *Nature* 346, 818-22 (1990); and Tuerk et al., *Science* 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying RNA or DNA aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool may be in vitro transcribed to produce a pool of RNA transcripts if an RNA aptamer is desired. The pool of RNA or DNA oligonucleotides may then be subjected to affinity chromatography, although any protocol which will allow selection of nucleic acids based on their ability to bind specifically to another molecule (e.g., a protein or any target molecule) may be used. In the case of affinity chromatography, the oligonucleotides are most typically passed through a column or contacted with magnetic beads or the like on which the target ligand has been immobilized. Oligonucleotides in the pool that bind to the ligand are retained on the column or bead, while nonbinding sequences are washed away. The oligonucleotides that bind the ligand are then amplified (after reverse transcription if RNA transcripts were generated) again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the molecules that are capable of acting as aptamers for the target ligand. Once an aptamer sequence has been successfully identified, the aptamer may be further optimized by performing additional rounds of selection starting from a pool of oligonucleotides comprising a mutagenized aptamer sequence. For use in the present invention, the aptamer is preferably selected for ligand binding in the presence of salt concentrations and temperatures which mimic normal physiological conditions.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present invention, the binding affinity of the aptamer for the ligand must be sufficiently strong and the structure formed by the aptamer when bound to its ligand must be significant enough so as to switch an aptamer-regulated nucleic acid of the invention between "on" and "off" states or tune the activity level of an aptamer-regulated nucleic acid.

Primer Sequences and Target Templates

A primer sequence may be a nucleic acid molecule, such as DNA or RNA, that is capable of hybridizing to a specific target nucleic acid template with high affinity and specificity. The primer sequence has a specific binding region that is capable of forming complexes with an intended target template molecule in an environment wherein other substances in the same environment are not complexed to the nucleic acid.

The specificity of the binding may be defined in terms of the comparative melting point of the primer sequence for its target template as compared to the melting point of the priming sequence for other unrelated nucleic acids in the environment. A target template will bind to the primer sequence with greater affinity than to unrelated material.

Hybridization of the primer sequence, or a portion of the primer sequence, to a target nucleic acid template forms a primer:template pair that is capable of acting as a substrate for an extrinsic enzyme. For example, a primer:template pair can serve as a substrate for a DNA polymerase that extends the primer to form an extension product that is complementary to the target template. Formation of the primer:template pair is dependent on ligand binding. For instance, the binding of a ligand to an aptamer causes a conformational change in the primer domain and alters its ability to hybridize to interact with its target template. Therefore, ligand binding affects the primer domain's ability to hybridize to a target template to form a primer:template pair, for example.

Hybridization of the primer sequence to the target template may be by conventional base pair complementarity. The ability to hybridize will depend on the degree of complementarity between the primer sequence and the target template. Generally, the longer the hybridizing portion of the primer sequence, the more base mismatches with a target nucleic acid it may contain and still form a stable duplex (or triplex, as the case may be). One skilled in the art can ascertain a tolerable degree of mismatch by use of standard procedures to determine the melting point of the hybridized complex. The melting point of the hybridized complex is determined according to the hybridization conditions in the assay that will be used. In certain embodiments, the length of the primer sequence of an aptamer-regulated nucleic acid is between about 8 and about 500 nucleotides. In other embodiments, the length of the primer sequence is between about 10 and about 250, about 20 and about 150 nucleotides, or about 20 and about 100 nucleotides. The length of the primer sequence that is complementary to the target template may be all or a portion of the primer sequence domain. For example, the length of a primer sequence that is complementary to a target template may be between about 4 and about 500 nucleotides. In other embodiments, the length of a primer sequence that is complementary to a target template is between about 10 and about 250, about 12 and about 150 nucleotides, or about 12 and about 100 nucleotides.

Under stringent conditions, a primer sequence in an ampliSwitch will hybridize to its target template, but not to an unrelated nucleic acid. Nucleic acid hybridization is affected by such conditions as salt concentration, temperature, organic solvents, base composition, length of the complementary strands, and the number of nucleotide base mismatches between the hybridizing nucleic acids. A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer complementary sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal inciting point (Tm) for the specific sequence at a defined ionic strength and pH. Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. to about 60° C. Stringent conditions may also be achieved with the addition of helix destabilizing agents such as formamide. The hybridization conditions may also vary when a non-ionic backbone, i.e. PNA is used, as is known in the art. In addition, cross-linking agents may be added to covalently attach a primer:template pair. These parameters may also be used to control non-specific binding, as is generally outlined in U.S. Pat. No. 5,681,697. Thus it may be desirable to perform certain steps at higher stringency conditions to reduce non-specific binding.

Sequence identity between the primer sequence and target template may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the primer sequence and the target template is preferred.

A target template may be engineered or it may be a portion of a gene, a regulatory sequence, genomic DNA, cDNA, RNA including mRNA and rRNA, or others. As is outlined herein, the target template may be a target sequence from a sample, or a secondary target such as a product of a reaction. The selection of a target template sequence is dependent on factors such as desired length, complementarity to the primer sequence, and desired length and sequence of the extension product produced upon primer extension of the primer sequence. The target template sequence may also depend on the method used to detect the extension product in a primer extension reaction that uses the primer:template pair as a substrate. The skilled artisan will evaluate these considerations to select the appropriate target template. For instance, the desired length of the extension product may be from about 5 nucleotides to about 5000 nucleotides, from about 10 nucleotides to about 3000 nucleotides, from about 20 nucleotides to about 1500 nucleotides, from about 25 nucleotides to about 750 nucleotides or from about 100 to about 500 nucleotides. Accordingly, the desired length of the target template will correspond to the desired length of the extension product, and therefore, be in a similar range, or about 5, 10, 25, 50, 100, 250, 500, 1000, 1500, 2500, or 5000 nucleotides long. The sequence of the target template can be tailored according to the method used to detect the extension product. For example, if methods such as size, fluorescence, radioactivity, or luminescence are used to detect the extension product, the sequence of the target template may not be critical. However, the sequence of the extension product, and therefore the target template, may be important when sequence specific hybridization of the extension product is used. For example, the extension product may be applied to a nucleic acid microarray or to nucleic acids spotted on a nitrocellulose filter. These detection methods depend on sequence specific hybridization to identify the extension product of interest. In instances where the extension product is detected by agarose-gel based electrophoresis, the exact sequence of the extension product, and therefore the target template, may not be critical, but the length of the product may be important to detecting the extension product.

A nucleic acid target template used in the invention may be synthesized by standard methods known in the art, e.g., by use of an automated DNA synthesizer. A target template may also be generated using standard recombinant DNA methods as described herein. Primer sequences and target templates refer to deoxyribonucleotides or ribonucleotides and polymers thereof in either single- or double-stranded form. Unless specifically limited, they encompass nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

If required, the sample and target template are prepared using known techniques. For example, the sample may be treated to lyse cells in a sample, using known lysis buffers, sonication, electroporation, etc., with purification occurring as needed, as will be appreciated by those in the art. In addition, the reactions outlined herein may be accomplished in a variety of ways, as will be appreciated by those in the art. Components of the reaction may be added simultaneously, or sequentially, in any order. In addition, the reaction may include a variety of other reagents which may be included in the assays. These include reagents such as salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Once the primer:template pair has formed, an enzyme, such as a primer extension enzyme (e.g., DNA polymerase, ligase, etc.), is used to synthesize an extension product. As for all the methods outlined herein, the enzymes may be added at any point during the assay. The identity of the enzyme will depend on the primer extension technique used, as is more fully outlined below.

3. Primer Extension

Extension of the primer sequence in a primer:template pair may be performed by any polymerase-mediated primer extension reaction and/or any nucleic acid amplification techniques. For instance, primer extension may be performed by PCR, SDA, RCA, NASBA, transcription-mediated amplification, ligase chain reaction, or other amplification methods known in the art. Natural, non-natural or modified nucleotides may be incorporated into the extension products. Non-natural or modified nucleotides include, without limitation, radioactively, fluorescently, or chemically-labeled nucleotides. Furthermore, extension products may comprise one or more fluorophores and/or quencher moieties which alter the fluorescence of the sample. A quencher moiety causes there to be little or no signal from a fluorescent label (e.g., a fluorophore) when placed in proximity to the label. Such methods are useful, for example, in rapid or high-throughput methods. Detection of a labeled extension product may be performed by direct or indirect means (e.g., via a biotin/avidin or a biotin/stretpavidin linkage, agarose gel-based methods, fluorescent detection, or sequence specific hybridization on an oligonucleotide microarray or nitrocellulose filter). It is not intended that the present invention be limited to any particular detection system or label.

The present invention is directed to the detection (and optionally quantification) of a ligand analyte in a sample by detecting products of nucleic acid primer extension reactions. Primer extension methods include, but are not limited to, polymerase chain reaction (PCR), rolling circle amplification (RCA), cycling probe technology (CPT), strand displacement assay (SDA), transcription mediated amplification (TMA), nucleic acid sequence based amplification (NASBA), ligation chain reaction (LCR), and invasive cleavage (e.g., Invader™) technology. All of these methods require a primer sequence nucleic acid (including nucleic acid analogs) that is hybridized to a target template to form a primer:template pair, and an enzyme is added to perform primer extension.

The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including, for example, "quantitative competitive PCR" or "QC-PCR", "arbitrarily primed PCR" or "AP-PCR", "immuno-PCR", "Alu-PCR", "PCR single strand conformational polymorphism" or "PCR-SSCP", allelic PCR (see Newton et al. Nucl. Acid Res. 17:2503 91989); "reverse transcriptase PCR" or "RT-PCR", "quantitative real-time PCR" or "RT-PCR", "biotin capture PCR", "vectorette PCR", "panhandle PCR", and "PCR select cDNA subtraction", among others. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

Cycling probe technology (CPT) is a nucleic acid detection system based on signal or probe amplification rather than target amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667, all of which are specifically incorporated herein by reference.

"Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998)

Nuc. Acids Res. 26:5073-5078; Barany, F. (1991) Proc. Natl. Acad. Sci. USA 88:189-193; and Lizardi et al. (1998) Nat. Genet. 19:225-232, all of which are incorporated by reference in their entirety.

In an illustrative embodiment, primer extension is achieved by SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In general, SDA may be described as follows. A single-stranded target template is contacted with an SDA primer, or the primer sequence as used herein. An "SDA primer" generally has a length of 25-100 nucleotides, with SDA primers of approximately 35 nucleotides being preferred. An SDA primer is substantially complementary to a region at the 3' end of the target template, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target template. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is extended to form an extension product, sometimes referred to herein as a "newly synthesized strand." The substituted dNTP is modified such that it will inhibit cleavage in the strand containing the substituted dNTP but will not inhibit cleavage on the other strand. Examples of suitable substituted dNTPs include, but are not limited, 2' deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5' to 3' exonuclease activity. However, if less than all the nucleotides are substituted, the polymerase preferably lacks 5' to 3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindIII, AvaI, Fnu4HI, TthIIII, NcII, BstXI, BamHI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5' to 3', thereby creating another newly synthesized strand. The polymerase chosen should be able to initiate 5' to 3' polymerization at a nick site, should also displace the polymerized strand downstream from the nick, and should lack 5' to 3' exonuclease activity (this may be additionally accomplished by the addition of a blocking agent). Suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified.

In general, SDA does not require thermocycling. The temperature of the reaction is generally set to be high enough to prevent non-specific hybridization but low enough to allow specific hybridization; this is generally from about 37° C. to about 42° C., depending on the enzymes.

Nucleic acid sequence based amplification (NASBA) is generally described in U.S. Pat. No. 5,409,818 and "Profiting from Gene-based Diagnostics", CTB International Publishing Inc., N.J., 1996, both of which are incorporated by reference.

In another embodiment, primer extension is achieved by nucleic acid sequence based amplification (NASBA). NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to TMA. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of reverse transcriptase.

In general, these techniques may be described as follows. A single-stranded target nucleic acid template, which may be a RNA target sequence (sometimes referred to herein as "the first target sequence" or "the first target template"), is contacted with a first primer, generally referred to herein as a "NASBA primer" (although "TMA primer" is also suitable). As used herein, an ampliSwitch primer sequence may serve as a NASBA primer or a TMA primer. These primers generally have a length of 25-100 nucleotides, with NASBA primers of approximately 50-75 nucleotides being preferred. The first primer is preferably a DNA primer that has at its 3' end a sequence that is substantially complementary to the 3' end of the first target template. The first primer also has an RNA polymerase promoter at its 5' end (or its complement (antisense), depending on the configuration of the system). The first primer is then hybridized to the first target template to form a first primer:template pair. The reaction mixture also includes a reverse transcriptase enzyme (a "NASBA reverse transcriptase") and a mixture of the four dNTPs, such that the first NASBA primer is extended to form an extension product, comprising a hybridization complex of RNA (the first target template) and DNA (the newly synthesized strand).

Suitable reverse transcriptase polymerases include, but are not limited to, avian myloblastosis virus reverse transcriptase ("AMV RT") and the Moloney murine leukemia virus RT. When the amplification reaction is TMA, the reverse transcriptase enzyme further comprises a RNA degrading activity as outlined below.

In addition to the components listed above, the NASBA reaction also includes an RNA degrading enzyme, also sometimes referred to herein as a ribonuclease, that will hydrolyze the RNA of an RNA:DNA hybrid without hydrolyzing single- or double-stranded RNA or DNA. Suitable ribonucleases include, but are not limited to, RNase H from *E. coli* and calf thymus.

The ribonuclease activity degrades the first RNA target template in the hybridization complex, resulting in a disassociation of the hybridization complex leaving a first single-stranded newly synthesized DNA strand (extension product), sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilize the antisense promoter and transcription initiation site of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage phiII, *Salmonella* phage sp6, or Pseudomonase phage gh-1.

In some embodiments, TMA and NASBA are used with starting DNA target sequences. In this embodiment, it is necessary to utilize the first primer comprising the RNA polymerase promoter and a DNA polymerase enzyme to generate a double-stranded DNA hybrid with the newly synthesized strand comprising the promoter sequence. The hybrid is then denatured and the second primer added.

Accordingly, the NASBA reaction requires, in no particular order, a first NASBA primer (e.g., an ampliSwitch primer sequence), a second NASBA primer comprising an antisense sequence of an RNA polymerase promoter, an RNA polymerase that recognizes the promoter, a reverse transcriptase, a DNA polymerase, an RNA degrading enzyme, and NTPs and dNTPs.

These components result in a single starting RNA template generating a single DNA duplex; however, since this DNA duplex results in the creation of multiple RNA strands, which can then be used to initiate the reaction again, amplification proceeds rapidly.

Accordingly, the TMA reaction requires, in no particular order, a first TMA primer, a second TMA primer comprising an antisense sequence of an RNA polymerase promoter, an RNA polymerase that recognizes the promoter, a reverse transcriptase with RNA degrading activity, a DNA polymerase, NTPs and dNTPs.

These components result in a single starting RNA template generating a single DNA duplex; however, since this DNA duplex results in the creation of multiple RNA strands, which can then be used to initiate the reaction again, amplification proceeds rapidly.

The ligation chain reaction (LCR) involves the ligation of two smaller probes into a single long probe, using the target sequence as the template for the ligase. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835.

A variation of LCR utilizes a type of "chemical ligation," as is generally outlined in U.S. Pat. Nos. 5,616,464 and 5,767,259. In this embodiment, similar to LCR, a pair of primers are utilized, wherein the first primer is substantially complementary to a first domain of the target and the second primer is substantially complementary to an adjacent second domain of the target (although, as for LCR, if a "gap" exists, a polymerase and dNTPs may be added to "fill in" the gap). Each primer has a portion that acts as a "side chain" that does not bind the target sequence and acts as one half of a stem structure that interacts non-covalently through hydrogen bonding, salt bridges, van der Waal's forces, etc. Certain embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes.

At least one of the side chains of the primers comprises an activatable cross-linking agent, generally covalently attached to the side chain, that upon activation, results in a chemical cross-link or chemical ligation. The activatible group may comprise any moiety that will allow cross-linking of the side chains, and include groups activated chemically, photonically and thermally, with photoactivatable groups being preferred. In some embodiments a single activatable group on one of the side chains is enough to result in cross-linking via interaction to a functional group on the other side chain; in alternate embodiments, activatable groups are required on each side chain.

Once the hybridization complex is formed, and the cross-linking agent has been activated such that the primers have been covalently attached, the reaction is subjected to conditions to allow for the dissociation of the hybridization complex, thus freeing up the target to serve as a template for the next ligation or cross-linking.

Q-beta replicase (QBR) is a mRNA amplification technique, similar to NASBA and TMA, that relies on an RNA-dependent RNA polymerase derived from the bacteriophage Q-beta that can synthesize up to a billion stands of product from a template.

Invader™ technology is based on structure-specific polymerases that cleave nucleic acids in a site-specific manner. Two probes are used: an "invader" probe and a "signaling" probe, that adjacently hybridize to a target sequence with a non-complementary overlap. The enzyme cleaves at the overlap due to its recognition of the "tail" and releases the "tail" with a label. This can then be detected. The Invader™ technology is described in U.S. Pat. Nos. 5,846,717; 5,614,402; 5,719,028; 5,541,311; and 5,843,669.

An extension product will generally contain phosphodiester bonds, although in some cases may have alternate backbones, nucleic acid analogs, peptide nucleic acids (PNAs), or any other structures or modifications outlined for other nucleic acid molecules described herein.

Standard instrumentation known to those skilled in the art are used for the amplification and detection of amplified DNA. For example, a wide variety of instrumentation has been developed for carrying out nucleic acid amplifications, particularly PCR, e.g. Johnson et al, U.S. Pat. No. 5,038,852 (computer-controlled thermal cycler); Wittwer et al, Nucleic Acids Research, 17: 4353-4357 (1989)(capillary tube PCR); Hallsby, U.S. Pat. No. 5,187,084 (air-based temperature control); Gamer et al, Biotechniques, 14: 112-115 (1993) (high-throughput PCR in 864-well plates); Wilding et al, International application No. PCT/US93/04039 (PCR in micro-machined structures); Schnipelsky et al, European patent application No. 90301061.9 (publ. No. 0381501 A2) (disposable, single use PCR device), and the like.

Detection Methods

The extension products generated in the primer extension methods described herein can be detected by any means known in the art for polynucleotide detection. Extension products may comprise labels sufficient for radioactive, fluorescent, or chemical detection. Furthermore, extension products may comprise one or more fluorophores and/or quencher moieties which alter the fluorescence of the sample. A quencher moiety causes there to be little or no signal from a fluorescent label (e.g., a fluorophore) when placed in proximity to the label. For example, a fluorescently labeled nucleotide will produce little or no signal when incorporated in an extension product in proximity to a quenching moiety, which may be a nucleotide linked to a quencher. Fluorescently labeled nucleotides that remain unincorporated, however, may produce a detectable signal.

Detection of a labeled extension product may be performed by direct or indirect means (e.g., via a biotin/avidin or a biotin/streptavidin linkage). It is not intended that the present invention be limited to any particular detection system or label. In one embodiment, an extension product is detected through one of three different methods: agarose gel detection, fluorescent detection, or sequence specific hybridization on a oligonucleotide microarray or nitrocellulose filter. These detection methods are standard in the art.

Conventional methods for detecting and/or identifying nucleic acids include agarose gel electrophoresis following staining (e.g., using ethidium bromide) of the gel and suitable visualization methods. Conventional methods also include northern blots, southern blots, or universal blots, generally involving the use of labeled (e.g., with a radiolabel or a fluorescent label) probe nucleic acids. For example, sensitive fluorescent gel stains are available for nucleic acid detection.

High throughput detection of nucleic acids is also available. For example, the use of multiple fluorescent tags enables discrimination between different classes of molecules in complex mixtures. Fluorescent multiplexing relies on optimal excitation and collection of fluorescent emission from each label. Multi-label analyses require a sensitive detection system capable of resolving multiple fluorescent signals. Typhoon 8600 is a versatile variable mode imager capable of fluorescence storage phosphor and chemiluminescence detection of gels, blots, microplates, or samples in other formats.

Chehab et al., Proc Natl Acad Sci USA. 1989 December; 86(23): 9178-9182, also reported a multiplex color complementation assay that obviates the need for gel electrophoresis and has been applied to the detection of certain genetic events.

Various microarray technologies can also be employed. For example, bead or microsphere-based microarrays are described in U.S. Pat. Nos. 6,942,968; 6,890,741; 6,770,441, and 6,355,431. Nucleic acid detection using microarrays and employing electron transfer moieties is also described in U.S. Pat. Nos. 6,875,619; 6,264,825; and 6,686,150. Oligonucleotide microarray is also provided in U.S. Pat. No. 6,040,138. Various nucleic acid amplification techniques are also described in these references, for example, PCR, LCR, CPT, RCA, and SDA are described in detail in U.S. Pat. No. 6,686, 150.

In a specific embodiment, the amplified DNA is analyzed by determining the length of the amplified DNA by electrophoresis or chromatography. For example, the amplified DNA is analyzed by gel electrophoresis. Methods of gel electrophoresis are well known in the art. See for example, *Current Protocols in Molecular Biology*, eds. Ausubel et al., John Wiley & Sons: 1992. The amplified DNA can be visualized, for example, by fluorescent or radioactive means, or with other dyes or markers that intercalate DNA. The DNA may also be transferred to a solid support such as a nitrocellulose membrane and subjected to Southern Blotting following gel electrophoresis. In one embodiment, the DNA is exposed to ethidium bromide and visualized under ultraviolet light.

In another embodiment, the amplified DNA is labeled, directly or indirectly, with a fluorescent, radioactive, chemical, or luminescent label. Labeled nucleotides may be incorporated directly into the extension product during DNA synthesis, or primers used in the amplification reaction may be labeled. The labeled nucleotides or primers are added to the solution prior or during the assay. When the assay is complete, unincorporated primers or nucleotides are removed (e.g., by chromatography). The amplified products and extension products are then measured for fluorescent, radioactive, chemical or luminescent activity with the appropriate equipment. For instance, a fluorimeter is used to measure the level of fluorescence in a sample.

In other embodiments, sequence specific hybridization is used to detect amplified products and extension products. Oligonucleotides immobilized on a solid support, such as on a microarray or nitrocellulose filter, are designed so that they are complementary to the amplified DNA or extension products from a primer:template pair. The amplified DNA or extension products are labeled (e.g., radioactively or fluorescently) and applied to the microarray or filter. The hybridization signal from each of the array elements is individually distinguishable. The array elements are addressed and their identities known, thus identifying the presence or absence of an amplified product in the reaction. In a preferred embodiment, the array elements comprise polynucleotides, although the present invention could also be used with cDNA or other types of nucleic acid array elements 4. Other applications Aptamer-regulated nucleic acids can also be employed in a multiplex fashion. The modular, tailor-made characteristic of ampliSwitches allows for the assay of complex mixtures of ligand analytes. Large libraries of ampliSwitches can be quickly generated to simultaneously assay and quantify large numbers of analytes by using orthogonal primer:template pairs with ampliSwitches designed to different analytes. In addition, it is possible through the forward engineering methods described herein to create libraries of switches that relate ranges of concentrations of analytes. AmpliSwitches designed to bind specific analytes and/or different concentration ranges of analytes would prime specific target templates. These multiplex assays can be run in a single reaction tube or sets of single reaction tubes depending on the number of analytes detected. Multiplex assays can be analyzed using agarose gels, where different templates are differentiated by different sizes, qRT-PCR, where different templates are differentiated with different fluorescently labeled primer pairs, and hybridization-based platforms, where different templates are designed to be complementary to nucleic acids such as oligonucleotides on microarrays or nitrocellulose filters.

AmpliSwitch technology can also be easily integrated into existing detection interfaces due to the flexibility in the design of primer:template pairs. In scaling this technology up to simultaneously detect concentrations of multiple analytes from a given sample, the readout of large sets of ampliSwitch primer:template pairs can be configured to take advantage of existing oligonucleotide arrays. Specifically, the amplified template for each ampliSwitch can be designed to hybridize existing oligonucleotide microarrays and detected using standard protocols such as SYBR green for detecting double-stranded binding and Cy3/Cy5 for comparative specific product labeling. The identity and concentration of each analyte is then detected according to the user-specified address on the microarray.

Accordingly, methods and compositions including the ampliSwitch molecules herein are useful in any application that involves detection of an analyte of interest. For example, an ampliSwitch molecule may comprise an aptamer domain that is responsive to a ligand or analyte of clinical, diagnostic interest, and such ligand or analyte of interest may be an antigen, an antibody, a cytokine, a metabolite, a drug intermediate, or any other molecule of clinical interest that may be indicative of a disease, a pathological condition, or a physiological condition. An ampliSwitch molecule may comprise an aptamer domain that is responsive to a ligand or analyte of environmental interest, and such ligand or analyte of interest may be a toxic substance (e.g., organic or inorganic toxic substances, protein toxins), an infectious agent (e.g., bacteria, viruses, fungi, prion), or a pollutant; such an ampliSwitch molecule is useful in environmental testing or monitoring, which may be testing of a sample of any origin for the ligand or analyte of environmental interest, or monitoring of a laboratory, any manufacturing plant, any public or private facility, or air space.

EXAMPLES

The invention now being generally described, it will be more readily understood by reference to the following examples, which are included merely for purposes of illustration of certain aspects and embodiments of the present invention, and are not intended to limit the invention.

AmpliSwitch Design

Figure 1A:
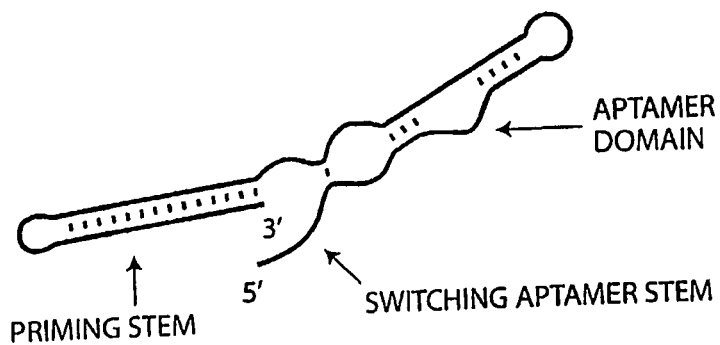
FIGS. 1A and 1B outline the components of an ampliSwitch nucleic acid.
Figure 1B:
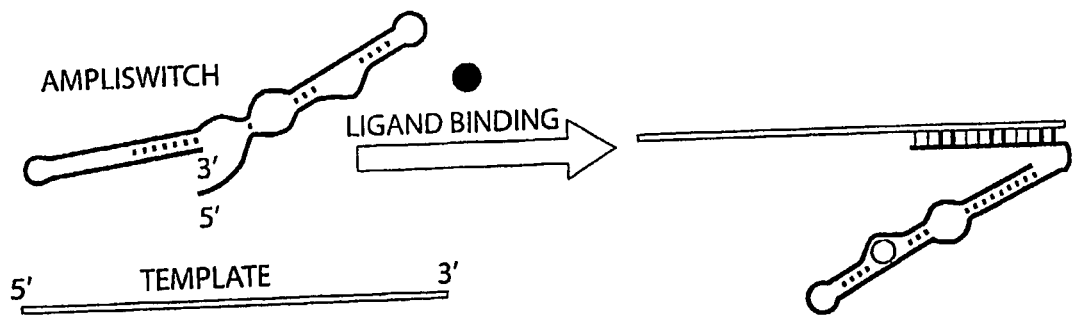
Figure 2:
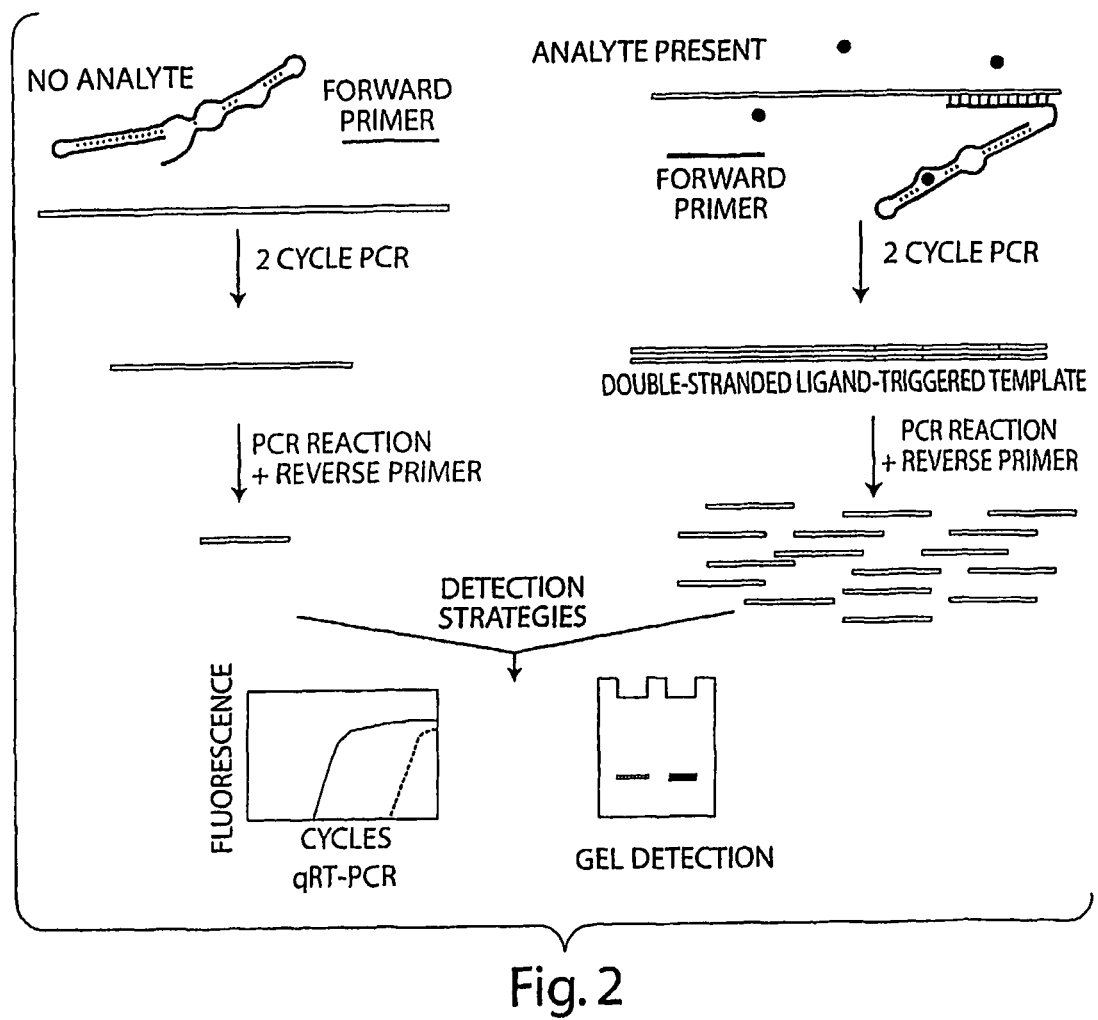
FIG. 2 is a schematic that illustrates the mechanism of ampliSwitch detection of analyte ligands. Analyte binding to an ampliSwitch induces a conformational change that enables ampliSwitch binding of the primer strand to its template. The triggered PCR detection assay converts the conformational change from an ampliSwitch binding event to an easy to detect output signal. The output from the triggered PCR assay is illustrated for both a positive and negative detection event. In the case of a positive detection event an amplified double-stranded DNA template is generated that can be detected, for example, through qRT-PCR or gel imaging. As illustrated, this signal is not generated from a negative detection event. The output is read as a binary, 'yes/no' signal.
Figure 3A:
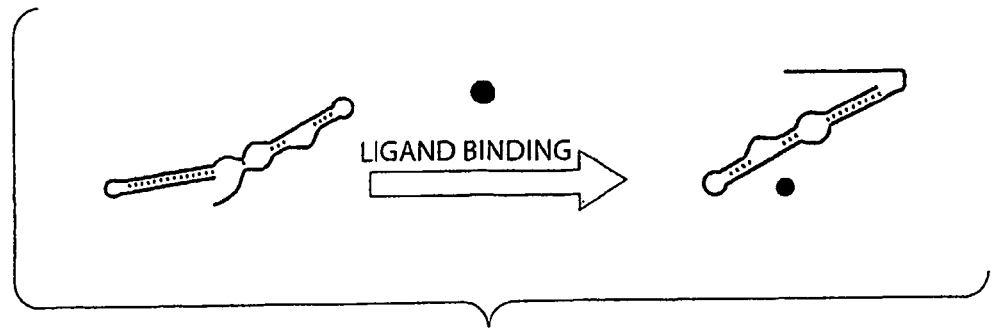
FIGS. 3A and 3B are schematic drawings that illustrate in vitro ligand analyte detection by ampliSwitch nucleic acids.
Figure 3B:
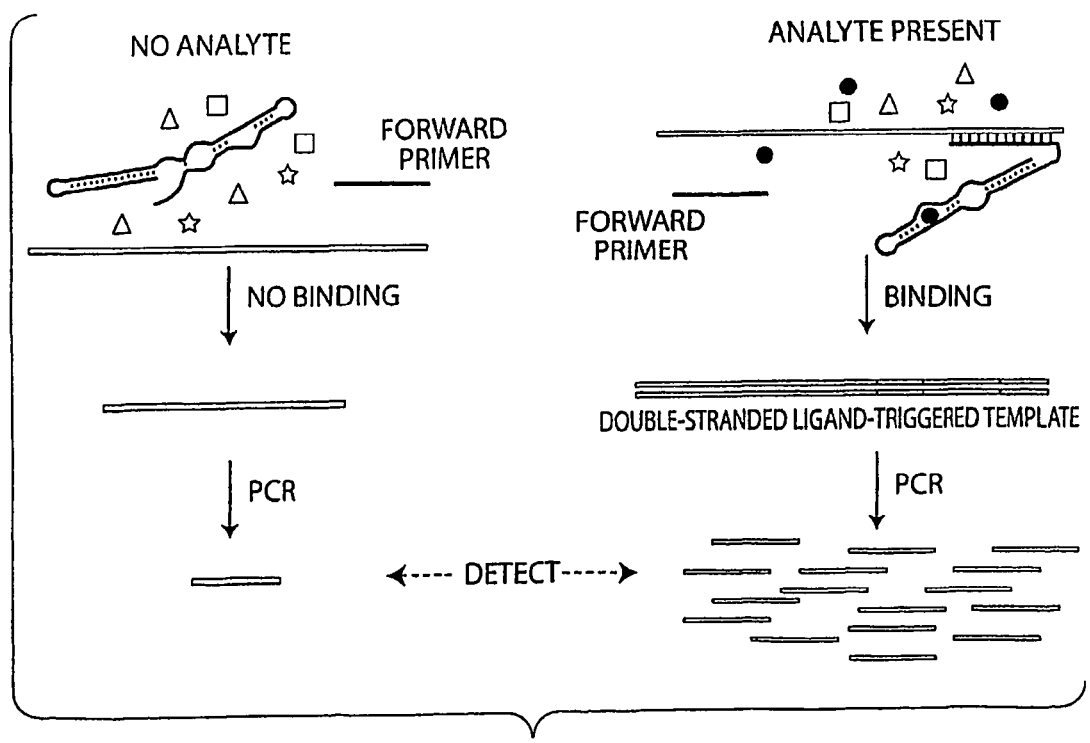
Figure 4:
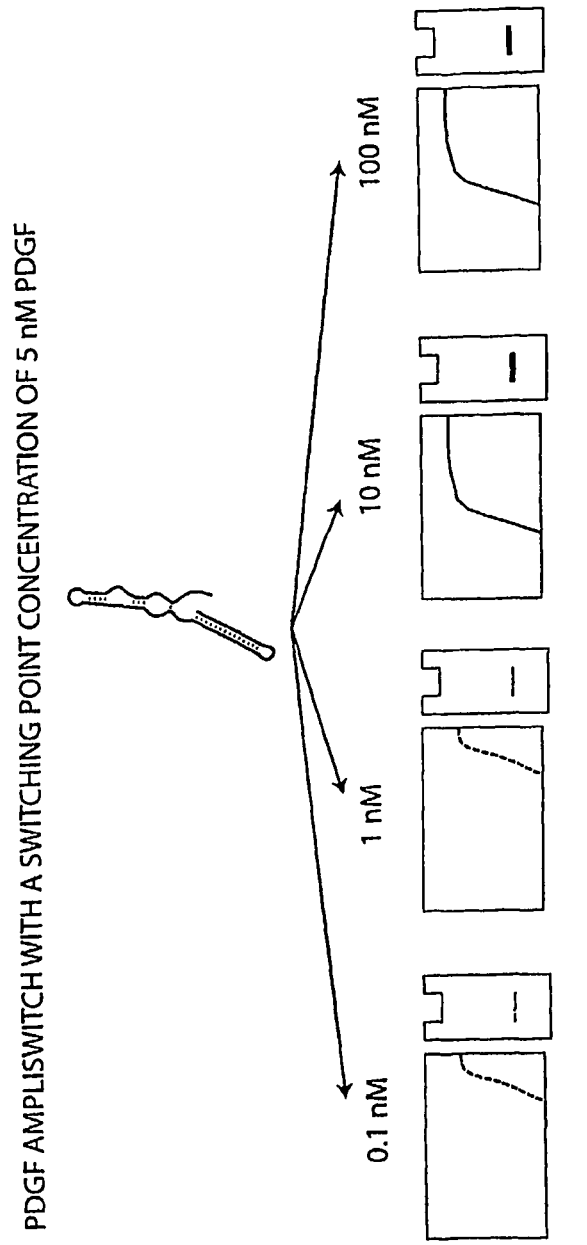
FIG. 4 is a drawing that illustrates the digital output signals generated from a PDGF ampliSwitch that switches its conformation around 5 nM PDGF. As illustrated, in solutions with concentrations lower that 5 nM PDGF the output from the triggered PCR assay will indicate a negative sensing event with background levels of amplification. In concentrations higher than 5 nM PDGF the output will indicate a positive sensing event with identical levels of amplification.
Figure 5:
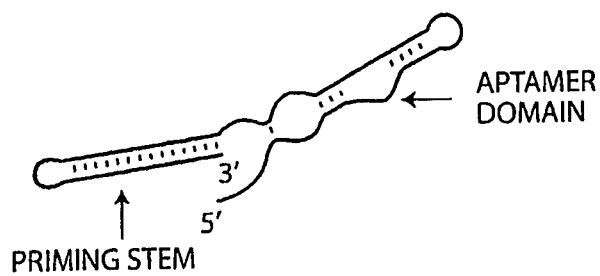
FIG. 5 is a diagram that shows the ampliSwitch sensor regions that will be targeted for tuning ligand response properties. The stability of the priming stem will be altered to affect the concentration switching point of an ampliSwitch using thermodynamic design strategies. In addition, the binding affinity of the aptamer domain for ligand can be changed to affect this switching point by using modular design strategies. Primer sequence is shown in red. Switching aptamer stem sequence is shown in blue
Figure 6:
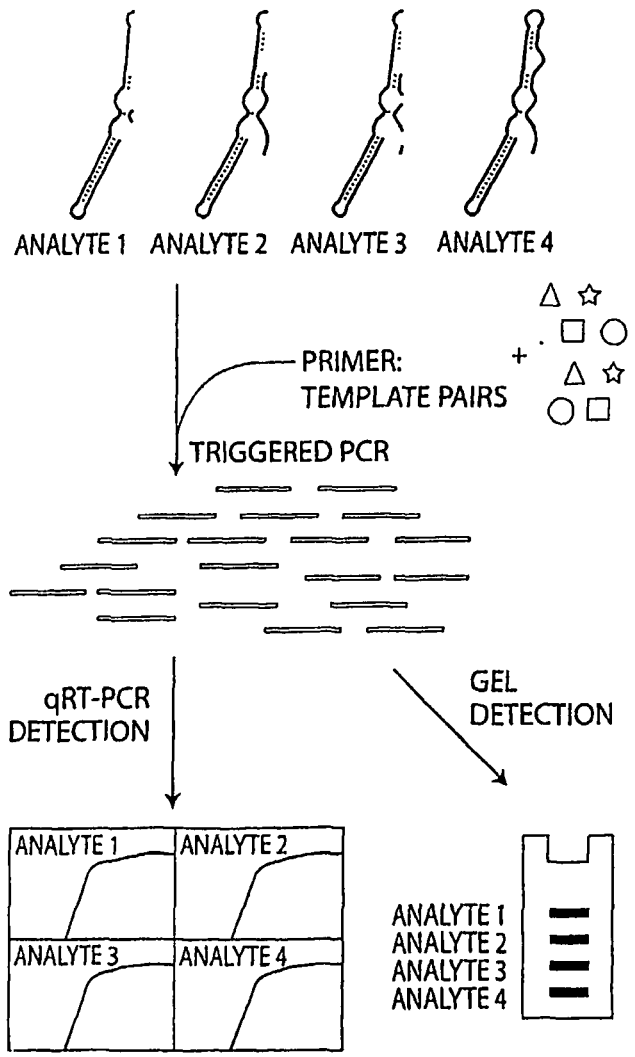
FIG. 6 is a schematic showing the use of a set of ampliSwitches for the simultaneous detection of different analytes using ampliSwitch sensors. Each analyte will be detected with a distinct ampliSwitch sensor and primer:template pair. The output from the triggered PCR reaction will be detected, for example, as different sized templates on a gel or different channel amplification signals through qRT-PCR.

An initial ampliSwitch is constructed using a previously selected aptamer that binds to Platelet Derived Growth Factor (PDGF) with high affinity and specificity. The primer sequence domain is designed to base pair with a 100 nucleotide target template. The stein of the PDGF aptamer is designed so that the primer sequence portion base pairs in a stable stem in the absence of ligand, but so that another overlapping stem forms upon ligand binding, the "aptamer stem," or the "aptamer domain," forcing the primer sequence portion into a more single-stranded state (FIG. 3A). The aptamer stem and primer sequence stem are designed such that the primer sequence stem is slightly more stable than the aptamer stem. It is anticipated that these molecules will function through alterations in conformational dynamics, such that in the absence of ligand and presence of target template, the stem sequestering the primer sequence is more likely to form; whereas in the presence of both ligand and target template, the free energy associated with binding of PDGF, and stabilization in the aptamer structure enables the aptamer stem to form, freeing the primer sequence to bind its target template. Due to the dual-stem design of the ampliSwitch, it is anticipated that the free energies of the aptamer binding to its ligand and the primer sequence binding to its target template will contribute in a cooperative manner to the structural switching of the ampliSwitch molecule.

AmpliSwitches and other oligos are synthesized using standard phosphoramidite chemistry (IDT). DNA is resuspended in water to a concentration of 10 micromolar. For ampliSwitch reactions, 200 nM ampliSwitch and 1 nM target template are incubated with various amounts of analyte (PDGF) in reaction buffer (10 mM Tris pH 8.0, 50 mM NaCl, 5 mM $MgCl_2$). Reactions are incubated at 37° C. for 15 minutes.

Quantitative real-time PCR (qRT-PCR) is performed on the samples (see FIGS. 11 and 12). Sybr Green qPCR master mix (BioRad, Hercules, Calif.) is added and reactions are cycled in an iCycler qPCR machine (BioRad, Hercules, Calif.). Amplification is quantified based on the difference in cycle numbers from the quantitative PCR. PCR extension products are not detected in samples that do not contain PDGF, or in samples where PDGF is not present in a concentration that causes a conformational switch in the PDGF sensor.

AmpliSwitch regulation is then determined by activating the ampliSwitch by the addition of PDGF to samples containing ampliSwitches in the 'off' state. Extension products are observed after several PCR cycles in samples with concentrations of PDGF that are high enough to cause a conformational switch in the PDGF sensor. This data supports that ampliSwitch molecules hybridize to their target templates to induce primer extension in the qRT-PCR reaction in the presence of activating levels of PDGF.

AmpliSwitch ligand affinity is also examined. Gel shift experiments are conducted in the presence of equimolar amounts of a short target template (250 nucleotides), labeled ampliSwitch and varying concentrations of PDGF to examine ampliSwitch ligand affinity. A sharp shift in ampliSwitch mobility is detected between 2 and 10 µM PDGF, presumably due to binding of both PDGF and target template. Nuclease mapping in the presence of ligand alone is also conducted to investigate ampliSwitch conformational changes.

Forward Engineering for Tuning Switching Dynamics

The switching behavior of the ampliSwitch platform is dependent on conformational dynamics of the structures; therefore it is possible to tune switching behavior in a straightforward manner by altering thermodynamic properties of the ampliSwitch. It is anticipated that the absolute and relative stabilities of the primer sequence stem and the aptamer stem will be important design parameters in tuning the switch behavior of an ampliSwitch. To explore the dynamic range of switch behavior, several ampliSwitches can be created with varying primer sequence and aptamer stem stabilities. It is anticipated that these altered ampliSwitches could expand the concentration range over which PDGF detection can be observed.

In general, it will be observed that increasing primer sequence stem stability by the addition of base pairs will create switches that required higher concentrations of PDGF to affect a switch, whereas decreasing stem stabilities will create switches that generate extension products at lower PDGF concentrations. For example, altering a single nucleotide in an ampliSwitch primer sequence will introduce a mismatched pair in the primer sequence stem so that in the absence of ligand, the construct is less thermodynamically stable. The less stable ampliSwitch will exhibit altered switch dynamics, and lower PDGF concentrations will be required to generate an extension product. Alternatively, increasing the stability of the primer sequence stem (e.g., by increasing the number of complementary nucleotides within the stem) creates a switch that requires higher concentrations of PDGF to generate an extension product.

Incorporation by Reference

All references cited herein are hereby incorporated by reference in their entirety.

Equivalents

While the above description contains many specific details of methods in accordance with this invention, these specific details should not be construed as limitations on the scope of the invention, but merely as exemplifications of preferred embodiments thereof. Those skilled in the art will envision many other possible variations that fall within the scope and spirit of the invention as defined by the claims appended hereto.

wherein:
(1) in a first conformation, the 3'-end priming sequence forms a hairpin structure, and the 5'-end switching aptamer stem sequence is single-stranded; and,
(2) in a second conformation, the 5'-end switching aptamer stem sequence hybridizes to a complementary region of the nucleic acid, and the 3'-end priming sequence is available for hybridization to a target template to form a primer:template pair;

The invention claimed is:

1. A nucleic acid comprising:
(i) an aptamer comprising a 5'-end switching aptamer stem sequence; and
(ii) a 3'-end priming sequence;

wherein binding to a ligand by the aptamer induces a conformational change of the nucleic acid to shift between the first conformation and the second conformation, or between the second conformation and the first conformation.

2. The nucleic acid of claim 1, wherein said primer:template pair acts as a substrate for an extrinsic enzymatic activity.

3. The nucleic acid of claim 2, wherein said extrinsic enzymatic activity is a DNA polymerase.

4. The nucleic acid of claim 2, wherein said extrinsic enzymatic activity is a ligase.

5. The nucleic acid of claim 3, wherein said polymerase is phi29 or taq polymerase.

6. The nucleic acid of claim 1, wherein said nucleic acid comprises ribonucleic acid (RNA), deoxyribonucleic acid (DNA), or both.

7. The nucleic acid of claim 1, wherein said conformational change produces or removes an intramolecular double-stranded feature, including said priming sequence, which double-stranded feature alters the availability of said priming sequence to hybridize to said target template.

8. The nucleic acid of claim 1, wherein said ligand is selected from the group consisting of small molecules, metal ions, natural products, polypeptides, peptide analogs. nucleic acids, carbohydrates, fatty acids and lipids, a non-peptide hormone (such as steroids) and metabolic precursors or products thereof, and enzyme co-factors, enzyme substrates and products of enzyme-mediated reactions.

9. An expression construct comprising (i) a coding sequence which, when transcribed, produces the nucleic acid of claim 1, and (ii) one or more transcriptional regulatory sequences that regulate transcription of said nucleic acid in an expression system containing said expression construct.

10. The expression construct of claim 9, wherein the expression system is a cell.

11. A recombinant cell engineered with one or more expression constructs of claim 9.

12. A library comprising two nucleic acids, wherein each nucleic acid comprises the nucleic acid of claim 1, and wherein each aptamer of said two nucleic acids has a different binding affinity for said ligand.

13. A library comprising two nucleic acids, wherein each nucleic acid comprises the nucleic acid of claim 1, and wherein each nucleic acid has a different thermodynamic stability that affects the likelihood that said conformational change will occur in response to binding to said ligand.

14. A library comprising two nucleic acids, wherein each nucleic acid comprises the nucleic acid of claim 1, and wherein each aptamer of said two nucleic acids binds to a different ligand.

15. The nucleic acid of claim 1, which is about 30-500 nucleotides in length.

16. The library of claim 12, wherein each said nucleic acid is about 30-500 nucleotides in length.

17. The library of claim 13, wherein each said nucleic acid is about 30-500 nucleotides in length.

18. The library of claim 14, wherein each said nucleic acid is about 30-500 nucleotides in length.

* * * * *

SEQUENCE LISTING

```
<160> NUMBER OF SEQ ID NOS: 4

<210> SEQ ID NO 1
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaatcggact catgggtcaa tggaattaat gatcaattga cagacgcaag tctccatgag      60
tccgattcgt attcccatac gaatcggact catg                                  94

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
catgagtccg attcgtat                                                    18

<210> SEQ ID NO 3
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 cttttatcg cccgggcact gcaagcaatt gcagtcccaa tgggcgggcg ataaaaagat       60
cgattcccat cgatcttttt atcgccc                                          87

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggcgataaa aagatcgat                                                   19
```